US007541519B2

(12) United States Patent
Debonte et al.

(10) Patent No.: US 7,541,519 B2
(45) Date of Patent: *Jun. 2, 2009

(54) FATTY ACID DESATURASES AND MUTANT SEQUENCES THEREOF

(75) Inventors: Lorin R. Debonte, Ft. Collins, CO (US); Basil S. Shorrosh, Ft. Collins, CO (US)

(73) Assignee: Cargill, Incorporated, Wayzata, MN (US)

( * ) Notice: Subject to any disclaimer, the term of this patent is extended or adjusted under 35 U.S.C. 154(b) by 331 days.

This patent is subject to a terminal disclaimer.

(21) Appl. No.: 11/108,185

(22) Filed: Apr. 18, 2005

(65) Prior Publication Data

US 2005/0262591 A1 Nov. 24, 2005

Related U.S. Application Data

(63) Continuation of application No. 10/757,909, filed on Jan. 15, 2004, now abandoned, which is a continuation of application No. 08/874,109, filed on Jun. 12, 1997, now abandoned, which is a continuation-in-part of application No. PCT/US96/20090, filed on Dec. 13, 1996, which is a continuation-in-part of application No. 08/572,027, filed on Dec. 14, 1995, now Pat. No. 7,135,614.

(51) Int. Cl.
*A01H 5/00* (2006.01)
*A01H 1/00* (2006.01)
(52) U.S. Cl. .................. 800/306; 800/264; 800/270
(58) Field of Classification Search ............... None
See application file for complete search history.

(56) References Cited

U.S. PATENT DOCUMENTS

| 4,627,192 | A | 12/1986 | Fick |
| 4,948,811 | A | 8/1990 | Spinner et al. |
| 5,387,758 | A | 2/1995 | Wong et al. |
| 5,434,283 | A | 7/1995 | Wong et al. |
| 5,545,821 | A | 8/1996 | Wong et al. |
| 5,625,130 | A | 4/1997 | Grant et al. |
| 5,629,193 | A | 5/1997 | Hudson et al. |
| 5,859,350 | A | 1/1999 | DeBonte et al. |
| 5,969,169 | A | 10/1999 | Fan |
| 6,342,658 | B1 * | 1/2002 | DeBonte et al. ............. 800/306 |
| 6,372,965 | B1 | 4/2002 | Lightner et al. |

FOREIGN PATENT DOCUMENTS

| CA | 2180386 | 1/1998 |
| EP | 323 753 | 8/1994 |
| WO | WO 91/15578 | 10/1991 |
| WO | WO 92/03919 | 3/1992 |
| WO | WO 93/11245 | 6/1993 |
| WO | WO 94/11516 | 5/1994 |
| WO | WO 97/21340 | 6/1997 |

OTHER PUBLICATIONS

GenBank Accession No. U50771 dated Apr. 4, 1996, 2 pages.
GenBank Accession No. X91139 dated Dec. 24, 2000, 2 pages.
"www.brassica.info sharing information world-wide for The Multinational Brassica Genome Project," at http://www.brassica.info/information/GenomeSize.htm.
Arondel et al., "Map-Based Cloning of a Gene Controlling Omega-3 Fatty Acid Desaturation in Arabidopsis," *Science*, 1992, 258:1153-1155.
Avelange-Macherel et al., "Site-directed mutagenesis of histidine residues in the Δ12 acyl-lipid desaturase of Synechocystis," *FEBS Letters*, 1995, 361:111-114.
*BRL Catalog and Reference Guide*, "Sequencing Primers," p. 61.
Brunklaus-Jung and Robbelen, "Genetical and Physiological Investigations on Mutants for Polyenoic Fatty Acids in Rapeseed (Brassica napus L.). III. Breeding Behaviour and Performance," *Plant Breeding*, 1987, 98:9-16.
Canvin, "The Effect of Temperature on the Oil Content and Fatty Acid Composition of the Oils from Several Oil Seed Crops," *Can. J. Botany*, 1965, 43:63-69.
Classen, Oral Presentation, GCIRC 8th International Rapeseed Congress, Saskatoon, Saskatchewan, Jul. 9-11, 1991, pp. 390-395.
Conner et al., "The Dietary Prevention and Treatment of Coronary Heart Disease," *Coronary Heart Disease: Prevention, Complications and Treatment*, 1985, pp. 43-64.
Craig, "Varietal and Environmental Effects on Rapeseed. III. Fatty Acid Composition of 1958 Varietal Tests," *Can. J. Plant Sci.*, 1961, 41:204-210.
Downey et al., "Methods of Breeding for Oil Quality in Rape," *Can. J. Plant Sci.*, 1963, 43:271-275.
Doyle et al., *J. Biol. Chem.*, 1986, 261:9228-9238.
Evans et al., "Edible Oil Evaluation by Room Odor Tests: A Preliminary Report," *J. Am. Oil Chem. Soc.*, 1971, 48:711-714.
Fox et al., "Stearoyl-acyl carrier protein Δ9 desaturase from ricinus communis is a diiron-oxo protein," *Proc. Natl. Acad. Sci. USA*, 1993, 90:2486-2490.
Galliard, "Degradation of Acyl Lipids: Hydrolytic and Oxidative Enzymes," *The Biochemistry of Plants*, 1980, 4:85-116.
Garg et al., *New England J. Med.*, 1988, 319:829-834.

(Continued)

*Primary Examiner*—Elizabeth F McElwain

(57) ABSTRACT

Seeds, plants and oils are provided having high oleic acid; low linoleic acid; and low linoleic acid plus linolenic acid; and advantageous functional or nutritional properties. Plants are disclosed that contain a mutation in a delta-12 or delta-15 fatty acid desaturase gene. Preferred plants are rapeseed and sunflower plants. Plants carrying such mutant genes have altered fatty acid composition in seeds. In one embodiment, a plant contains a mutation in a region having the conserved motif His-Xaa-Xaa-Xaa-His, found in delta-12 and delta-15 fatty acid desaturases. A preferred motif has the sequence His-Glu-Cys-Gly-His. A preferred mutation in this motif has the amino acid sequence His-Lys-Cys-Gly-His. Nucleic acid fragments are disclosed that comprise a mutant delta-12 or delta-15 fatty acid desaturase gene sequence.

4 Claims, 14 Drawing Sheets

OTHER PUBLICATIONS

Gaul, "Mutations in Plant Breeding," *Radiation Botany*, 1964, 4:155-232.

Grundy, *New England J. Med.*, 1986, 314:745-748.

Hawrysh, "Stability of Canola Oil," *Canola and Rapeseed Production, Chemistry, Nutrition and Processing Technology*, 1990, Chapter 7, pp. 99-122.

Hitz et al., *Plant Physiol.*, 1994, 103:635-641.

Hoffman et al., "Anther Culture as a Breeding Tool in Rape. II. Progeny Analyses of Androgenetic Lines and Induced Mutants from Haploid Cultures," *Theor. Appl. Genet.*, 1982, 61:225-232.

Jönsson et al., "Quality breeding in rapeseed," *Svalöv 1886-1986 Research and Results in Plant Breeding*, Gösta Olsson (ed.), LTs forlag, Stockholm, pp. 173-184.

Keys (ed.), *Circulation*, vol. XLI, Suppl. I, 1970, pp. I162-I183.

Kirk-Othmer, *Encyclopedia of Chemical Technol.*, 3rd Ed., 1980, 9:795-831.

Kondra et al., "Selection for Oleic, Linoleic and Linolenic Acid Content in F2 Populations of Rapeseed," *Can. J. Plant Sci.*, 1976, 56:961-966.

Koseoglu et al., "Chemistry, Analysis, and Nutritional Effects," "Hydrogenation of Canola Oil," *Canola and Rapeseed: Production, Chemistry, Nutrition, and Processing Technology*, 1990, Van Nostrand Reinhold, NY, Chap. 8, pp. 123-148.

Lim et al., "Expressed sequence tags of Chinese cabbage flower bud cDNA," *Plant Physiol.*, 1996, 111(2):577-588.

Lindqvist et al., *EMBO J.*, 1996, 15(16):4081-4092.

Mattson, "A changing role for dietary monounsaturated fatty acids," *J. Am. Diet. Assoc.*, 1989, 89:387-391.

Mensink et al., "Effect of a Diet Enriched with Monounsaturated or Polyunsaturated Fatty Acids on Levels of Low-Density and High-Density Lipoprotein Cholesterol in Healthy Women and Men," *New England J. Med.*, 1989, 321:436-441.

Mensink et al., "Effect of Dietary Trans Fatty Acids on High-Density and Low-Density Lipoprotein Cholesterol Levels in Healthy Subjects," *New England J. Med.*, 1990, 323:439-445.

Neidleman, "Temperature Effects in the Biosynthesis of Unique Fats and Fatty Acids," *Proc. of the World Conf. On Biotech. Fats Oils Ind.*, 1988.

Newman et al., "Genes Galore: A Summary of Methods for Accessing Results from Large-Scale Partial Sequencing of Anonymous Arabidopsis cDNA Clones ," *Plant Physiol.*, 1994, 106:1241-1255.

Okuley et al., *Plant Cell*, 1994, 6:147-158.

Paul et al., "Inheritance of S-methyl-L-cysteine sulphoxide and thiocyanate contents in forage rape (Brassica napus L.)," *Theor. Appl. Genet.*, 1986, 72:706-709.

Pleines and Friedt, "Breeding for Improved C18-Fatty Acid Composition in Rapeseed (Brassica napus L.)," *Fat Sci. Technol.*, 1988, 90(5):167-171.

Pleines et al., "Recurrent Selection for Modified Polyenoic Fatty Acid Composition in Rapeseed (Brassica napus L.)," Abstract of The Proceedings of the 7th International Rapeseed Congress, Poznan, Poland, May 11-14, 1987.

Pleines et al., Abstract of the 43rd Lecture Meeting of Deutsche Gesellschaft fur Feltwissenschaft in Hamburg, Sep. 30-Oct. 1, 1987.

Rakow and McGregor, "Opportunities and Problems in Modification of Levels of Rapeseed C18 Unsaturated Fatty Acids," *J. Am. Oil Chem. Soc.*, 1973, 50:400-403.

Rakow, "Selection for Linoleic and Linolenic Acid Content in Rape Seed after Mutagenic Treatment," *Z. Pflanzenzüchtg.*, 1973, 69:62-82.

Ram et al., "Biotechnology for Brassica and Helianthus improvement," *Proceedings World Conference on Biotechnology for the Fats and Oils Industry*, Sep. 27-Oct. 2, 1987.

Rennie et al., "Fatty Acid Composition of Oil from Soybean Seeds Grown at Extreme Temperatures," *J. Am. Oil Chem. Soc.*, 1989, 66:1622-1624.

Röbbelen and Nitsch, "Genetical and Physiological Investigations on Mutants for Polyenoic Fatty Acids in Rapeseed, Brassica napus L.," *Z. Pflanzenzüchtg.*, 1975, 75:93-105.

Röbbelen and Rakow, "Selection for Fatty Acids in Rapeseed," *Proceedings of the International Conference on the Scientific, Technology and Marketing of Rapeseed and Rapeseed Products*, Sep. 20-23, 1970.

Röbbelen, "Changes and Limitations of Breeding for Improved Polyenoic Fatty Acids Content in Rapeseed," *Biotechnology for the Oils and Fats Industry*, 1984, American Oil Chemists Society, 97-105.

Roy and Tarr, "IXLIN—an Interspecific Source for High Linoleic and Low Linolenic Acid Content in Rapeseed (Brassica napus L.)," *Z. Pflanzenzüchtg.*, 1985, 95:201-209.

Roy and Tarr, "Prospects for the Development of Rapeseed (B. napus L.) with Improved Linoleic and Linolenic Acid Content," *Plant Breeding*, 1987, 98:89-96.

Scarth et al., "Stellar Low Linolenic—High Linoleic Acid Summer Rape," *Can. J. Plant Sci.*, 1988, 68:509-511.

Shanklin et al., "Eight Histidine Residues Are Catalytically Essential in a Membrane-Associated Iron Enzyme, Stearoyl-CoA Desaturase, and Are Conserved in Alkane Hydroxylase and Xylene Monooxygenase," *Biochemistry*, 1994, 33:12787-12794.

Shpota, "Rape and Mustard Breeding for Oil Quality," *Proceedings of the 7th International Rapeseed Congress*, May 11-14, 1987, 2:560-565.

Slightom et al., *Proc. Natl. Acad. Sci. USA*, 1983, 80:1897-1901.

Stefansson et al., "Tower Summer Rape," *Can. J. Plant Sci.*, 1975, 55:343-344.

Stefansson, "The Development of Improved Rapeseed Cultivars," *High and Low Erucic Acid Rapeseed Oils*, Academic Press Inc., 1983, pp. 143-159.

Tanhuanpää, "Mapping and cloning of FAD2 gene to develop allele-specific PCR for oleic acid in spring turnip rape (Brassica rapa ssp. OleiferaI), *Molecular Breeding*, 1998, 4(6):543-550.

Töpfer et al., "Modification of Plant Lipid Synthesis," *Science*, 1995, 268:681-686.

Tremolieres et al., "Unsaturated Fatty Acids in Maturing Seeds of Sunflower and Rape: Regulation by Temperature and Light Intensity," *Phytochemistry*, 1982, 21(1), 41-45.

Ullrich et al., "Identification of the Most Intense Odor Compounds Formed During Autoxidation of Methyl Linolenate at Room Temperature," *J. Am. Oil Chem. Soc.*, 1988, 65:1313-1317.

Wada et al., "Enhancement of chilling tolerance of a cyanobacterium by genetic manipulation of fatty acid desaturation," *Nature*, 1990, 347:200-203.

Western Canada Canola Rapeseed Recommendations Committee 1990 Cooperative Trial Date.

Williams et al., *J. Am. Med. Assoc.*, 1987, 257:3251-3256.

Yadav et al., *Plant Physiol.*, 1993, 103:467-476.

Heppard et al., "Developmental and Growth Temperature Regulation of Two Different Microsomal ω-6 Desaturase Genes in Soybeans," *Plant Physiol.*, 1996, 110:311-319.

* cited by examiner

Fig. 2A

```
161 CCTACCTCATCTCTGGGACAATCATCATAGCCTTCCTTGCTTCTA      Fad2-D wt
161 CCTACCTCATCTCTGGGACAATCATCATAGCCTTCCTTGCTTCTA      Fad2-D (GA316) IMC 129
161 CCTACCTCATCTCTGGGACAATCATCATAGCCTTCCTTGCTTCTA      Fad2-F wt
161 CCTACCTCATCTCTGGGACAATCATCATAGCCTTCCTTGCTTCTA      Fad2-F (TA515) Q508
161 CCTACCTCATCTCTGGGACAATCATCATAGCCTTCCTTGCTTCTA      Fad2-F (GA908) Q4275
                170         180         190         200

201 CTACGTCGCCACCACCACTTACCTTCCCTCCCCTCACCCT           Fad2-D wt
201 CTACGTCGCCACCACCACTTACCTTCCCTCCCCTCACCCT           Fad2-D (GA316) IMC 129
201 CTACGTCGCCACCACCACTTACCTTCCCTCCCCTCACCCT           Fad2-F wt
201 CTACGTCGCCACCACCACTTACCTTCCCTCCCCTCACCCT           Fad2-F (TA515) Q508
201 CTACGTCGCCACCACCACTTACCTTCCCTCCCCTCACCCT           Fad2-F (GA908) Q4275
                210         220         230         240

241 CTCTCCTACTTTCGCCCTGTCTCTCTCTCCTCACCCTGCCAGG        Fad2-D wt
241 CTCTCCTACTTTCGCCCTGTCTCTCTCTCCTCACCCTGCCAGG        Fad2-D (GA316) IMC 129
241 CTCTCCTACTTTCGCCCCTGGCCCTCTCTCCTCACCCTGCCAAG       Fad2-F wt
241 CTCTCCTACTTTCGCCCCTGGCCCTCTCTCCTCACCCTGCCAAG       Fad2-F (TA515) Q508
241 CTCTCCTACTTTCGCCCCTGGCCCTCTCTCCTCACCCTGCCAAG       Fad2-F (GA908) Q4275
                250         260         270         280

281 GCTGCCTAACCGGCGTCTGGGTCATAGCCCACGAGTG              Fad2-D wt
281 GCTGCCTAACCGGCGTCTGGGTCATAGCCCACGAGTG              Fad2-D (GA316) IMC 129
281 GGTGCCTAACCGGCGTCTGGGTCATAGCCCACGAGTG              Fad2-F wt
281 GGTGCCTAACCGGCGTCTGGGTCATAGCCCACGAAGTG             Fad2-F (TA515) Q508
281 GGTGCCTAACCGGCGTCTGGGTCATAGCCCACGAGTG              Fad2-F (GA908) Q4275
                290         300         310         320
```

Fig. 2B

```
                                330                  340                  350                  360
     |---------+---------+---------+---------+---------+---------+---------+---------|
321  C G G C C A C C A C G C C C T T C A G C G A C T A C C A G T G G C T G G A C G A C  Fad2-D wt
321  C G G C C A C C A C G C C C T T C A G C G A C T A C C A G T G G C T G G A C G A C  Fad2-D (GA316) IMC 129
321  C G G C C A C C A C G C C C T T C A G C G A C T A C C A G T G G C T T G A C G A C  Fad2-F wt
321  C G G C C A C C A C G C C C T T C A G C G A C T A C C A G T G G C T T G A C G A C  Fad2-F (TA515) Q508
321  C G G C C A C C A C G C C C T T C A G C G A C T A C C A G T G G C T T G A C G A C  Fad2-F (GA908) Q4275

370                  380                  390                  400
     |---------+---------+---------+---------+---------+---------+---------+---------|
361  A C C G T C G G C C T C T C C A T C T C T T C C T T C C T C C T C C T C C T C C T T  Fad2-D wt
361  A C C G T C G G C C T C T C C A T C T C T T C C T T C C T C C T C C T C C T C C T T  Fad2-D (GA316) IMC 129
361  A C C G T C G G C C T C T C C A T C T C T T C C T T C C T C C T C C T C C T C C T T  Fad2-F wt
361  A C C G T C G G C C T C T C C A T C T C T T C C T T C C T C C T C C T C C T C C T T  Fad2-F (TA515) Q508
361  A C C G T C G G C C T C T C C A T C T C T T C C T T C C T C C T C C T C C T C C T T  Fad2-F (GA908) Q4275

410                  420                  430                  440
     |---------+---------+---------+---------+---------+---------+---------+---------|
401  A C T T C T C C T G G A A G T A C A G T C A T C G A C G C C A C C A T T C C A A  Fad2-D wt
401  A C T T C T C C T G G A A G T A C A G T C A T C G A C G C C A C C A T T C C A A  Fad2-D (GA316) IMC 129
401  A C T T C T C C T G G A A G T A C A G T C A T C G A C G C C A C C A T T C C A A  Fad2-F wt
401  A C T T C T C C T G G A A G T A C A G T C A T C G A C G C C A C C A T T C C A A  Fad2-F (TA515) Q508
401  A C T T C T C C T G G A A G T A C A G T C A T C G A C G C C A C C A T T C C A A  Fad2-F (GA908) Q4275

450                  460                  470                  480
     |---------+---------+---------+---------+---------+---------+---------+---------|
441  C A C T G G C T C C C C T C G A G A G A C G A A G T G T T T G T C C C C A A G  Fad2-D wt
441  C A C T G G C T C C C C T C G A G A G A C G A A G T G T T T G T C C C C A A G  Fad2-D (GA316) IMC 129
441  C A C T G G C T C C C C T C G A G A G A C G A A G T G T T T G T T C C C C A A G  Fad2-F wt
441  C A C T G G C T C C C C T C G A G A G A C G A A G T G T T T G T T C C C C A A G  Fad2-F (TA515) Q508
441  C A C T G G C T C C C C T C G A G A G A C G A A G T G T T T G T T C C C C A A G  Fad2-F (GA908) Q4275
```

| | | | | | | |
|---|---|---|---|---|---|---|
| 641 | ACGCTCCC | CATCTACA | ACGACCG | TGAGCGT | CTCCAGA | TATA | Fad2-D wt |
| 641 | ACGCTCCC | CATCTACA | ACGACCG | TGAGCGT | CTCCAGA | TATA | Fad2-D (GA316) IMC 129 |
| 641 | ACGCTCCC | CATCTACA | ACGACCG | CGAGCGT | CTCCAGA | TATA | Fad2-F wt |
| 641 | ACGCTCCC | CATCTACA | ACGACCG | CGAGCGT | CTCCAGA | TATA | Fad2-F (TA515) Q508 |
| 641 | ACGCTCCC | CATCTACA | ACGACCG | CGAGCGT | CTCCAGA | TATA | Fad2-F (GA908) Q4275 |

650   660   670   680

| | | | | | | |
|---|---|---|---|---|---|---|
| 681 | CATCTCCC | GACGGCTG | GCTCCTC | CGTCTCT | GGTCTCT | C | Fad2-D wt |
| 681 | CATCTCCC | GACGGCTG | GCTCCTC | CGTCTCT | GGTCTCT | C | Fad2-D (GA316) IMC 129 |
| 681 | CATCTCCC | GACGGCTG | GCTCCTC | CGTCTCT | GGTCTCT | C | Fad2-F wt |
| 681 | CATCTCCC | GACGGCTG | GCTCCTC | CGTCTCT | GGTCTCT | C | Fad2-F (TA515) Q508 |
| 681 | CATCTCCC | GACGGCTG | GCTCCTC | CGTCTCT | GGTCTCT | C | Fad2-F (GA908) Q4275 |

690   700   710   720

| | | | | | | |
|---|---|---|---|---|---|---|
| 721 | TACCGCTA | CGGCTGCT | GTCCAAGG | AGTTGCC | TTCGATG | GTCT | Fad2-D wt |
| 721 | TACCGCTA | CGGCTGCT | GTCCAAGG | AGTTGCC | TTCGATG | GTCT | Fad2-D (GA316) IMC 129 |
| 721 | TTCCGTTA | CGGCTGCT | GCCGGCG | AGTTGGC | TTCGATG | GTCT | Fad2-F wt |
| 721 | TTCCGTTA | CGGCTGCT | GCCGGCG | AGTTGGC | TTCGATG | GTCT | Fad2-F (TA515) Q508 |
| 721 | TTCCGTTA | CGGCTGCT | GCCGGCG | AGTTGGC | TTCGATG | GTCT | Fad2-F (GA908) Q4275 |

730   740   750   760

| | | | | | | |
|---|---|---|---|---|---|---|
| 761 | GCTTCTAC | GGAGTTCC | TCTTCTTC | TGATTGT | CAACGGG | TTCTT | Fad2-D wt |
| 761 | GCTTCTAC | GGAGTTCC | TCTTCTTC | TGATTGT | CAACGGG | TTCTT | Fad2-D (GA316) IMC 129 |
| 761 | GCTTCTAC | GGAGTCC | TCCCCGC | TGATTGT | CAATGGG | TTTCT | Fad2-F wt |
| 761 | GCTTCTAC | GGAGTCC | TCCCCGC | TGATTGT | CAATGGG | TTCCT | Fad2-F (TA515) Q508 |
| 761 | GCTTCTAC | GGAGTCC | TCCCCGC | TGATTGT | CAATGGG | TTCCT | Fad2-F (GA908) Q4275 |

```
     810                820                830                840
801  AGTTTTGATCACTTACTTGCAGCACACGCATCCTTCCCTG  Fad2-D wt
801  AGTTTTGATCACTTACTTGCAGCACACGCATCCTTCCCTG  Fad2-D (GA316) IMC 129
801  CGTTGTTGATCACTTACTTGCAGCACACGCATCCTTCCCTG Fad2-F wt
801  CGTTGTTGATCACTTACTTGCAGCACACGCATCCTTCCCTG Fad2-F (TA515) Q508
801  CGTGTTGATCACTTACTTGCAGCACACGCATCCTTCCCTG  Fad2-F (GA908) Q4275

850                860                870                880
841  CCTCACTATGACTCGTCTGAGTGGGATTGGTTTGAGGGGAG Fad2-D wt
841  CCTCACTATGACTCGTCTGAGTGGGATTGGTTTGAGGGGAG Fad2-D (GA316) IMC 129
841  CCTCACTACGATTCGTCCGAGTGGGATTGGTTTGAGGGGAG Fad2-F wt
841  CCTCACTACGATTCGTCCGAGTGGGATTGGTTTGAGGGGAG Fad2-F (TA515) Q508
841  CCTCACTACGATTCGTCCGAGTGGGATTGGTTTGAGGGGAG Fad2-F (GA908) Q4275

890                900                910                920
881  CTTTTGGCCCACCCGTTTGACAGAGACTACGGAATCTTGAACAA Fad2-D wt
881  CTTTTGGCCCACCCGTTTGACAGAGACTACGGAATCTTGAACAA Fad2-D (GA316) IMC 129
881  CTTTTGGCTACCCGTTTGACAGAGACTACGGAAATCTTGAACAA Fad2-F wt
881  CTTTTGGCTACCCGTTTGACAGAGACTACGGAAATCTTGAACAA Fad2-F (TA515) Q508
881  CTTTTGGCTACCCGTTTGACAGAGACTACGGAAATCTTGAACAA Fad2-F (GA908) Q4275

930                940                950                960
921  GGTCTTTCCACAATATCACGGACACGGCACGGCGGCATCAC Fad2-D wt
921  GGTCTTTCCACAATATCACGGACACGGCACGGCGGCATCAC Fad2-D (GA316) IMC 129
921  GGTCTTTCCACAATATTACCGACACGGCACGGCGGCATCAT Fad2-F wt
921  GGTCTTTCCACAATATTACCGACACGGCACGGCGGCATCAT Fad2-F (TA515) Q508
921  GGTCTTTCCACAATATTACCGACACGGCACGGCGGCATCAT Fad2-F (GA908) Q4275
```

Fig. 2J

```
                                                                    1000
            970            980            990       |
961  CTGTTTCTTCGACCATGCCGCATTATCATGCGAAGCTA           Fad2-D wt
961  CTGTTTCTTCGACCATGCCGCATTATCATGCGAAGCTA           Fad2-D (GA316) IMC 129
961  CTGTTTCTTCCACACGATGCCGCATTATCACGCGAAGCTA          Fad2-F wt
961  CTGTTTCTTCCACATGCCGCATTATCACGCGAAGCTA            Fad2-F (TA515) Q508
961  CTGTTTCTTCCACGATGCCGCATTATCACGCGAAGCTA           Fad2-F (GA908) Q4275

1040
           1010           1020           1030      |
1001 CGAAGGCGATAAAGCCGATACTGGGAGAGTATTATCAGTT         Fad2-D wt
1001 CGAAGGCGATAAAGCCGATACTGGGAGAGTATTATCAGTT         Fad2-D (GA316) IMC 129
1001 CCAAGGCGATAAAGCCCGATACTGGGAGAGTATTATCAGTT        Fad2-F wt
1001 CCAAGGCGATAAAGCCCGATACTGGGAGAGTATTATCAGTT        Fad2-F (TA515) Q508
1001 CCAAGGCGATAAAGCCCGATACTGGGAGAGTATTATCAGTT        Fad2-F (GA908) Q4275

1080
           1050           1060           1070      |
1041 CGATGGGACGCCCGGTGGTTAAGGCGATGTGTGGAGGAGGCG        Fad2-D wt
1041 CGATGGGACGCCCGGTGGTTAAGGCGATGTGTGGAGGAGGCG        Fad2-D (GA316) IMC 129
1041 CGATGGGACGCCCGGTGGTTAAGGCGATGTGTGGAGGAGGCG        Fad2-F wt
1041 CGATGGGACGCCCGGTGGTTAAGGCGATGTGTGGAGGAGGCG        Fad2-F (TA515) Q508
1041 CGATGGGACGCCCGGTGGTTAAGGCGATGTGTGGAGGAGGCG        Fad2-F (GA908) Q4275
```

Fig. 29

|       |       |       | 1090  |       |       | 1100  |       |       | 1110  |       |       | 1120  |              |
|-------|-------|-------|-------|-------|-------|-------|-------|-------|-------|-------|-------|-------|--------------|
| 1081  | A A G G A G T G T A T C T A T G T G G A A C C G G A C A G G C A A A G G T G A G A | Fad2-D wt |
| 1081  | A A G G A G T G T A T C T A T G T G G A A C C G G A C A G G C A A A G G T G A G A | Fad2-D (GA316) IMC 129 |
| 1081  | A A G G A G T G T A T C T A T G T G G A A C C G G A C A G G C A A A G G T G A G A | Fad2-F wt |
| 1081  | A A G G A G T G T A T C T A T G T G G A A C C G G A C A G G C A A A G G T G A G A | Fad2-F (TA515) Q508 |
| 1081  | A A G G A G T G T A T C T A T G T G G A A C C G G A C A G G C A A A G G T G A G A | Fad2-F (GA908) Q4275 |

|       |       |       | 1130  |       |       | 1140  |       |       | 1150  |       |              |
|-------|-------|-------|-------|-------|-------|-------|-------|-------|-------|-------|--------------|
| 1121  | A G A A A G G T G T T C T T G G T A C A A C A A T A A G T T A T G A | Fad2-D wt |
| 1121  | A G A A A G G T G T T C T T G G T A C A A C A A T A A G T T A T G A | Fad2-D (GA316) IMC 129 |
| 1121  | A G A A A G G T G T T C T T G G T A C A A C A A T A A G T T A T G A | Fad2-F wt |
| 1121  | A G A A A G G T G T T C T T G G T A C A A C A A T A A G T T A T G A | Fad2-F (TA515) Q508 |
| 1121  | A G A A A G G T G T T C T T G G T A C A A C A A T A A G T T A T G A | Fad2-F (GA908) Q4275 |

Fig. 2H

|  |  |  |  |  |  |  |  |  |  | 10 |  |  |  |  |  |  |  |  |  | 20 |  |
|---|---|---|---|---|---|---|---|---|---|---|---|---|---|---|---|---|---|---|---|---|---|
| 1 | Met | Gly | Ala | Gly | Gly | Arg | Met | Gln | Val | Ser | Pro | Pro | Ser | Lys | Lys | Ser | Glu | Thr | Asp | Asn | Fad2-D wt |
| 1 | Met | Gly | Ala | Gly | Gly | Arg | Met | Gln | Val | Ser | Pro | Pro | Ser | Lys | Lys | Ser | Glu | Thr | Asp | Asn | Fad2-D (GA316) IMC129 |
| 1 | Met | Gly | Ala | Gly | Gly | Arg | Met | Gln | Val | Ser | Pro | Pro | Ser | Lys | Lys | Ser | Glu | Thr | Asp | Thr | Fad2-F wt |
| 1 | Met | Gly | Ala | Gly | Gly | Arg | Met | Gln | Val | Ser | Pro | Pro | Ser | Lys | Lys | Ser | Glu | Thr | Asp | Thr | Fad2-F (TA515) Q508 |
| 1 | Met | Gly | Ala | Gly | Gly | Arg | Met | Gln | Val | Ser | Pro | Pro | Ser | Lys | Lys | Ser | Glu | Thr | Asp | Thr | Fad2-F (GA908) Q4275 |

|  |  |  |  |  |  |  |  |  |  | 30 |  |  |  |  |  |  |  |  |  | 40 |  |
|---|---|---|---|---|---|---|---|---|---|---|---|---|---|---|---|---|---|---|---|---|---|
| 21 | Ile | Lys | Arg | Val | Pro | Cys | Glu | Thr | Pro | Phe | Thr | Val | Gly | Glu | Leu | Lys | Lys | Ala | Ile | Fad2-D wt |
| 21 | Ile | Lys | Arg | Val | Pro | Cys | Glu | Thr | Pro | Phe | Thr | Val | Gly | Glu | Leu | Lys | Lys | Ala | Ile | Fad2-D (GA316) IMC129 |
| 21 | Ile | Lys | Arg | Val | Pro | Cys | Glu | Thr | Pro | Phe | Thr | Val | Gly | Glu | Leu | Lys | Lys | Ala | Ile | Fad2-F wt |
| 21 | Ile | Lys | Arg | Val | Pro | Cys | Glu | Thr | Pro | Phe | Thr | Val | Gly | Glu | Leu | Lys | Lys | Ala | Ile | Fad2-F (TA515) Q508 |
| 21 | Ile | Lys | Arg | Val | Pro | Cys | Glu | Thr | Pro | Phe | Thr | Val | Gly | Glu | Leu | Lys | Lys | Ala | Ile | Fad2-F (GA908) Q4275 |

|  |  |  |  |  |  |  |  |  |  | 50 |  |  |  |  |  |  |  |  |  | 60 |  |
|---|---|---|---|---|---|---|---|---|---|---|---|---|---|---|---|---|---|---|---|---|---|
| 41 | Pro | Pro | His | Cys | Phe | Lys | Arg | Ser | Ile | Pro | Arg | Ser | Phe | Ser | Tyr | Leu | Ile | Trp | Asp | Ile | Fad2-D wt |
| 41 | Pro | Pro | His | Cys | Phe | Lys | Arg | Ser | Ile | Pro | Arg | Ser | Phe | Ser | Tyr | Leu | Ile | Trp | Asp | Ile | Fad2-D (GA316) IMC129 |
| 41 | Pro | Pro | His | Cys | Phe | Lys | Arg | Ser | Ile | Pro | Arg | Ser | Phe | Ser | Tyr | Leu | Ile | Trp | Asp | Ile | Fad2-F wt |
| 41 | Pro | Pro | His | Cys | Phe | Lys | Arg | Ser | Ile | Pro | Arg | Ser | Phe | Ser | Tyr | Leu | Ile | Trp | Asp | Ile | Fad2-F (TA515) Q508 |
| 41 | Pro | Pro | His | Cys | Phe | Lys | Arg | Ser | Ile | Pro | Arg | Ser | Phe | Ser | Tyr | Leu | Ile | Trp | Asp | Ile | Fad2-F (GA908) Q4275 |

|  |  |  |  |  |  |  |  |  |  | 70 |  |  |  |  |  |  |  |  |  | 80 |  |
|---|---|---|---|---|---|---|---|---|---|---|---|---|---|---|---|---|---|---|---|---|---|
| 61 | Ile | Ile | Ala | Ser | Cys | Phe | Tyr | Tyr | Val | Ala | Thr | Thr | Tyr | Phe | Pro | Leu | Leu | Pro | His | Pro | Fad2-D wt |
| 61 | Ile | Ile | Ala | Ser | Cys | Phe | Tyr | Tyr | Val | Ala | Thr | Thr | Tyr | Phe | Pro | Leu | Leu | Pro | His | Pro | Fad2-D (GA316) IMC129 |
| 61 | Ile | Ile | Ala | Ser | Cys | Phe | Tyr | Tyr | Val | Ala | Thr | Thr | Tyr | Phe | Pro | Leu | Leu | Pro | His | Pro | Fad2-F wt |
| 61 | Ile | Ile | Ala | Ser | Cys | Phe | Tyr | Tyr | Val | Ala | Thr | Thr | Tyr | Phe | Pro | Leu | Leu | Pro | His | Pro | Fad2-F (TA515) Q508 |
| 61 | Ile | Ile | Ala | Ser | Cys | Phe | Tyr | Tyr | Val | Ala | Thr | Thr | Tyr | Phe | Pro | Leu | Leu | Pro | His | Pro | Fad2-F (GA908) Q4275 |

```
                  90                         100
 81 Leu Ser Tyr Phe Ala Trp Pro Leu Tyr Phe Ala Cys Gln Gly Cys Val Leu Thr Gly Val   Fad2-D wt
 81 Leu Ser Tyr Phe Ala Trp Pro Leu Tyr Phe Ala Cys Gln Gly Cys Val Leu Thr Gly Val   Fad2-D (GA316) IMC129
 81 Leu Ser Tyr Phe Ala Trp Pro Leu Tyr Phe Ala Cys Gln Gly Cys Val Leu Thr Gly Val   Fad2-F wt
 81 Leu Ser Tyr Phe Ala Trp Pro Leu Tyr Phe Ala Cys Gln Gly Cys Val Leu Thr Gly Val   Fad2-F (TA515) Q508
 81 Leu Ser Tyr Phe Ala Trp Pro Leu Tyr Phe Ala Cys Gln Gly Cys Val Leu Thr Gly Val   Fad2-F (GA908) Q4275

110                         120
101 Trp Val Ile Ala His Glu Cys Gly His Ala Phe Ser Asp Tyr Gln Trp Leu Asp Asp       Fad2-D wt
101 Trp Val Ile Ala His Lys Cys Gly His Ala Phe Ser Asp Tyr Gln Trp Leu Asp Asp       Fad2-D (GA316) IMC129
101 Trp Val Ile Ala His Glu Cys Gly His Ala Phe Ser Asp Tyr Gln Trp Leu Asp Asp       Fad2-F wt
101 Trp Val Ile Ala His Glu Cys Gly His Ala Phe Ser Asp Tyr Gln Trp Leu Asp Asp       Fad2-F (TA515) Q508
101 Trp Val Ile Ala His Glu Cys Gly His Ala Phe Ser Asp Tyr Gln Trp Leu Asp Asp       Fad2-F (GA908) Q4275

130                         140
121 Thr Val Gly Leu Ile Phe His Ser Phe Leu Leu Val Pro Tyr Phe Ser Trp Lys Tyr Ser   Fad2-D wt
121 Thr Val Gly Leu Ile Phe His Ser Phe Leu Leu Val Pro Tyr Phe Ser Trp Lys Tyr Ser   Fad2-D (GA316) IMC129
121 Thr Val Gly Leu Ile Phe His Ser Phe Leu Leu Val Pro Tyr Phe Ser Trp Lys Tyr Ser   Fad2-F wt
121 Thr Val Gly Leu Ile Phe His Ser Phe Leu Leu Val Pro Tyr Phe Ser Trp Lys Tyr Ser   Fad2-F (TA515) Q508
121 Thr Val Gly Leu Ile Phe His Ser Phe Leu Leu Val Pro Tyr Phe Ser Trp Lys Tyr Ser   Fad2-F (GA908) Q4275

150                         160
141 His Arg Arg His His Ser Asn Thr Gly Ser Leu Glu Arg Asp Glu Val Phe Val Pro Lys   Fad2-D wt
141 His Arg Arg His His Ser Asn Thr Gly Ser Leu Glu Arg Asp Glu Val Phe Val Pro Lys   Fad2-D (GA316) IMC129
141 His Arg Arg His His Ser Asn Thr Gly Ser Leu Glu Arg Asp Glu Val Phe Val Pro Lys   Fad2-F wt
141 His Arg Arg His His Ser Asn Thr Gly Ser Leu Glu Arg Asp Glu Val Phe Val Pro Lys   Fad2-F (TA515) Q508
141 His Arg Arg His His Ser Asn Thr Gly Ser Leu Glu Arg Asp Glu Val Phe Val Pro Lys   Fad2-F (GA908) Q4275
```

Fig. 3B

| | | | | | | | | | | | | |
|---|---|---|---|---|---|---|---|---|---|---|---|---|
| 161 | Lys | Lys | Ser | Asp | Ile | Lys | Trp | Tyr | Gly | Lys | Tyr | Leu | Asn | Asn | Pro | Leu | Gly | Arg | Thr | Val | Fad2-D wt |
| 161 | Lys | Lys | Ser | Asp | Ile | Lys | Trp | Tyr | Gly | Lys | Tyr | Leu | Asn | Asn | Pro | Leu | Gly | Arg | Thr | Val | Fad2-D (GA316) IMC129 |
| 161 | Lys | Lys | Ser | Asp | Ile | Lys | Trp | Tyr | Gly | Lys | Tyr | Leu | Asn | Asn | Pro | Leu | Gly | Arg | Thr | Val | Fad2-F wt |
| 161 | Lys | Lys | Ser | Asp | Ile | Lys | Trp | Tyr | Gly | Lys | Tyr | His | Asn | Asn | Pro | Leu | Gly | Arg | Thr | Val | Fad2-F (TA515) Q508 |
| 161 | Lys | Lys | Ser | Asp | Ile | Lys | Trp | Tyr | Gly | Lys | Tyr | Leu | Asn | Asn | Pro | Leu | Gly | Arg | Thr | Val | Fad2-F (GA908) Q4275 |
| 181 | Met | Leu | Thr | Val | Gln | Phe | Thr | Leu | Gly | Trp | Pro | Leu | Tyr | Leu | Ala | Phe | Asn | Val | Ser | Gly | Fad2-D wt |
| 181 | Met | Leu | Thr | Val | Gln | Phe | Thr | Leu | Gly | Trp | Pro | Leu | Tyr | Leu | Ala | Phe | Asn | Val | Ser | Gly | Fad2-D (GA316) IMC129 |
| 181 | Met | Leu | Thr | Val | Gln | Phe | Thr | Leu | Gly | Trp | Pro | Leu | Tyr | Leu | Ala | Phe | Asn | Val | Ser | Gly | Fad2-F wt |
| 181 | Met | Leu | Thr | Val | Gln | Phe | Thr | Leu | Gly | Trp | Pro | Leu | Tyr | Leu | Ala | Phe | Asn | Val | Ser | Gly | Fad2-F (TA515) Q508 |
| 181 | Met | Leu | Thr | Val | Gln | Phe | Thr | Leu | Gly | Trp | Pro | Leu | Tyr | Leu | Ala | Phe | Asn | Val | Ser | Gly | Fad2-F (GA908) Q4275 |
| 201 | Arg | Pro | Tyr | Asp | Gly | Gly | Phe | Ala | Cys | His | Phe | His | Pro | Asn | Ala | Pro | Ile | Tyr | Asn | Asp | Fad2-D wt |
| 201 | Arg | Pro | Tyr | Asp | Gly | Gly | Phe | Ala | Cys | His | Phe | His | Pro | Asn | Ala | Pro | Ile | Tyr | Asn | Asp | Fad2-D (GA316) IMC129 |
| 201 | Arg | Pro | Tyr | Asp | Gly | Gly | Phe | Ala | Cys | His | Phe | His | Pro | Asn | Ala | Pro | Ile | Tyr | Asn | Asp | Fad2-F wt |
| 201 | Arg | Pro | Tyr | Asp | Gly | Gly | Phe | Ala | Cys | His | Phe | His | Pro | Asn | Ala | Pro | Ile | Tyr | Asn | Asp | Fad2-F (TA515) Q508 |
| 201 | Arg | Pro | Tyr | Asp | Gly | Gly | Phe | Ala | Cys | His | Phe | His | Pro | Asn | Ala | Pro | Ile | Tyr | Asn | Asp | Fad2-F (GA908) Q4275 |
| 221 | Arg | Glu | Arg | Leu | Gln | Ile | Tyr | Ile | Ser | Asp | Ala | Gly | Ile | Leu | Ala | Val | Cys | Tyr | Gly | Leu | Fad2-D wt |
| 221 | Arg | Glu | Arg | Leu | Gln | Ile | Tyr | Ile | Ser | Asp | Ala | Gly | Ile | Leu | Ala | Val | Cys | Tyr | Gly | Leu | Fad2-D (GA316) IMC129 |
| 221 | Arg | Glu | Arg | Leu | Gln | Ile | Tyr | Ile | Ser | Asp | Ala | Gly | Ile | Leu | Ala | Val | Cys | Tyr | Gly | Leu | Fad2-F wt |
| 221 | Arg | Glu | Arg | Leu | Gln | Ile | Tyr | Ile | Ser | Asp | Ala | Gly | Ile | Leu | Ala | Val | Cys | Tyr | Gly | Leu | Fad2-F (TA515) Q508 |
| 221 | Arg | Glu | Arg | Leu | Gln | Ile | Tyr | Ile | Ser | Asp | Ala | Gly | Ile | Leu | Ala | Val | Cys | Tyr | Gly | Leu | Fad2-F (GA908) Q4275 |

Fig. 3C

```
241 Tyr Arg Tyr Ala Ala Val Gln Gly Val Ala Ser Met Val Cys Phe Tyr Gly Val Pro Leu    Fad2-D wt
241 Tyr Arg Tyr Ala Ala Val Gln Gly Val Ala Ser Met Val Cys Phe Tyr Gly Val Pro Leu    Fad2-D (GA316) IMC129
241 Phe Arg Tyr Ala Ala Val Gln Gly Val Ala Ser Met Val Cys Phe Tyr Gly Val Pro Leu    Fad2-F wt
241 Phe Arg Tyr Ala Ala Ala Gln Gly Val Ala Ser Met Val Cys Phe Tyr Gly Val Pro Leu    Fad2-F (TA515) Q508
241 Phe Arg Tyr Ala Ala Ala Gln Gly Val Ala Ser Met Val Cys Phe Tyr Gly Val Pro Leu    Fad2-F (GA908) Q4275
                                        250                                260

261 Leu Ile Val Asn Gly Phe Leu Val Leu Ile Thr Tyr Leu Gln His Thr His Pro Ser Leu    Fad2-D wt
261 Leu Ile Val Asn Gly Phe Leu Val Leu Ile Thr Tyr Leu Gln His Thr His Pro Ser Leu    Fad2-D (GA316) IMC129
261 Leu Ile Val Asn Gly Phe Leu Val Leu Ile Thr Tyr Leu Gln His Thr His Pro Ser Leu    Fad2-F wt
261 Leu Ile Val Asn Gly Phe Leu Val Leu Ile Thr Tyr Leu Gln His Thr His Pro Ser Leu    Fad2-F (TA515) Q508
261 Leu Ile Val Asn Gly Phe Leu Val Leu Ile Thr Tyr Leu Gln His Thr His Pro Ser Leu    Fad2-F (GA908) Q4275
                                        270                                280

281 Pro His Tyr Asp Ser Ser Glu Trp Asp Trp Leu Arg Gly Ala Leu Ala Thr Val Asp Arg    Fad2-D wt
281 Pro His Tyr Asp Ser Ser Glu Trp Asp Trp Leu Arg Gly Ala Leu Ala Thr Val Asp Arg    Fad2-D (GA316) IMC129
281 Pro His Tyr Asp Ser Ser Glu Trp Asp Trp Leu Arg Gly Ala Leu Ala Thr Val Asp Arg    Fad2-F wt
281 Pro His Tyr Asp Ser Ser Glu Trp Asp Trp Leu Arg Gly Ala Leu Ala Thr Val Asp Arg    Fad2-F (TA515) Q508
281 Pro His Tyr Asp Ser Ser Glu Trp Asp Trp Leu Arg Gly Ala Leu Ala Thr Val Asp Arg    Fad2-F (GA908) Q4275
                                        290                                300

301 Asp Tyr Gly Ile Leu Asn Lys Val Phe His Asn Ile Thr Asp Thr His Val Ala His His    Fad2-D wt
301 Asp Tyr Gly Ile Leu Asn Lys Val Phe His Asn Ile Thr Asp Thr His Val Ala His His    Fad2-D (GA316) IMC129
301 Asp Tyr Gly Ile Leu Asn Lys Val Phe His Asn Ile Thr Asp Thr His Val Ala His His    Fad2-F wt
301 Asp Tyr Gly Ile Leu Asn Lys Val Phe His Asn Ile Thr Asp Thr His Val Ala His His    Fad2-F (TA515) Q508
301 Asp Tyr Glu Ile Leu Asn Lys Val Phe His Asn Ile Thr Asp Thr His Val Ala His His    Fad2-F (GA908) Q4275
                                        310                                320
```

Fig. 3D

|     |                                                                         |     |
| --- | ----------------------------------------------------------------------- | --- |
|     | 330                                                                 340 |     |
| 321 | Leu Phe Ser Thr Met Pro His Tyr His Ala Met Glu Ala Thr Lys Ala Ile Lys Pro Ile | Fad2-D wt |
| 321 | Leu Phe Ser Thr Met Pro His Tyr His Ala Met Glu Ala Thr Lys Ala Ile Lys Pro Ile | Fad2-D (GA316) IMC129 |
| 321 | Leu Phe Ser Thr Met Pro His Tyr His Ala Met Glu Ala Thr Lys Ala Ile Lys Pro Ile | Fad2-F wt |
| 321 | Leu Phe Ser Thr Met Pro His Tyr His Ala Met Glu Ala Thr Lys Ala Ile Lys Pro Ile | Fad2-F (TA515) Q508 |
| 321 | Leu Phe Ser Thr Met Pro His Tyr His Ala Met Glu Ala Thr Lys Ala Ile Lys Pro Ile | Fad2-F (GA908) Q4275 |
|     | 350                                                                 360 |     |
| 341 | Leu Gly Glu Tyr Tyr Gln Phe Asp Gly Thr Pro Val Val Lys Ala Met Trp Arg Glu Ala | Fad2-D wt |
| 341 | Leu Gly Glu Tyr Tyr Gln Phe Asp Gly Thr Pro Val Val Lys Ala Met Trp Arg Glu Ala | Fad2-D (GA316) IMC129 |
| 341 | Leu Gly Glu Tyr Tyr Gln Phe Asp Gly Thr Pro Val Val Lys Ala Met Trp Arg Glu Ala | Fad2-F wt |
| 341 | Leu Gly Glu Tyr Tyr Gln Phe Asp Gly Thr Pro Val Val Lys Ala Met Trp Arg Glu Ala | Fad2-F (TA515) Q508 |
| 341 | Leu Gly Glu Tyr Tyr Gln Phe Asp Gly Thr Pro Val Val Lys Ala Met Trp Arg Glu Ala | Fad2-F (GA908) Q4275 |
|     | 370                                                                 380 |     |
| 361 | Lys Glu Cys Ile Tyr Val Glu Pro Asp Arg Gln Gly Glu Lys Lys Gly Val Phe Trp Tyr | Fad2-D wt |
| 361 | Lys Glu Cys Ile Tyr Val Glu Pro Asp Arg Gln Gly Glu Lys Lys Gly Val Phe Trp Tyr | Fad2-D (GA316) IMC129 |
| 361 | Lys Glu Cys Ile Tyr Val Glu Pro Asp Arg Gln Gly Glu Lys Lys Gly Val Phe Trp Tyr | Fad2-F wt |
| 361 | Lys Glu Cys Ile Tyr Val Glu Pro Asp Arg Gln Gly Glu Lys Lys Gly Val Phe Trp Tyr | Fad2-F (TA515) Q508 |
| 361 | Lys Glu Cys Ile Tyr Val Glu Pro Asp Arg Gln Gly Glu Lys Lys Gly Val Phe Trp Tyr | Fad2-F (GA908) Q4275 |
| 381 | Asn Asn Lys Leu ter | Fad2-D wt |
| 381 | Asn Asn Lys Leu ter | Fad2-D (GA316) IMC129 |
| 381 | Asn Asn Lys Leu ter | Fad2-F wt |
| 381 | Asn Asn Lys Leu ter | Fad2-F (TA515) Q508 |
| 381 | Asn Asn Lys Leu ter | Fad2-F (GA908) Q4275 |

Fig. 3E ized. Okuley, et al., Plant Cell 6:147-158 (1994).

SEQUENCE LISTING

```
<160> NUMBER OF SEQ ID NOS: 70

<210> SEQ ID NO 1
<211> LENGTH: 1155
<212> TYPE: DNA
<213> ORGANISM: Brassica napus
<220> FEATURE:
<221> NAME/KEY: CDS
<222> LOCATION: (1)...(1152)
<223> OTHER INFORMATION: Wild type Fad2
<220> FEATURE:
<221> NAME/KEY: misc_feature
<222> LOCATION: 205
<223> OTHER INFORMATION: n = a, g, c, or t/u

<400> SEQUENCE: 1 atg ggt gca ggt gga aga atg caa gtg tct cct ccc tcc aag aag tct        48
Met Gly Ala Gly Gly Arg Met Gln Val Ser Pro Pro Ser Lys Lys Ser
 1               5                  10                  15 gaa acc gac acc atc aag cgc gta ccc tgc gag aca ccg ccc ttc act        96
Glu Thr Asp Thr Ile Lys Arg Val Pro Cys Glu Thr Pro Pro Phe Thr
            20                  25                  30 gtc gga gaa ctc aag aaa gca atc cca ccg cac tgt ttc aaa cgc tcg       144
Val Gly Glu Leu Lys Lys Ala Ile Pro Pro His Cys Phe Lys Arg Ser
        35                  40                  45 atc cct cgc tct ttc tcc tac ctc atc tgg gac atc atc ata gcc tcc       192
Ile Pro Arg Ser Phe Ser Tyr Leu Ile Trp Asp Ile Ile Ile Ala Ser
    50                  55                  60 tgc ttc tac tac ntc gcc acc act tac ttc cct ctc ctc cct cac cct       240
Cys Phe Tyr Tyr Xaa Ala Thr Thr Tyr Phe Pro Leu Leu Pro His Pro
65                  70                  75                  80 ctc tcc tac ttc gcc tgg cct ctc tac tgg gcc tgc caa ggg tgc gtc       288
Leu Ser Tyr Phe Ala Trp Pro Leu Tyr Trp Ala Cys Gln Gly Cys Val
                85                  90                  95 cta acc ggc gtc tgg gtc ata gcc cac gaa tgc ggc cac cac gcc ttc       336
Leu Thr Gly Val Trp Val Ile Ala His Glu Cys Gly His His Ala Phe
            100                 105                 110 agc gac tac cag tgg ctt gac gac acc gtc ggt ctc atc ttc cac tcc       384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cgc agc cac       432
Phe Leu Leu Val Pro Tyr Phe Ser Trp Lys Tyr Ser His Arg Ser His
    130                 135                 140 cat tcc aac act ggc tcc ctc gag aga gac gaa gtg ttt gtc ccc aag       480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg       528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg       576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc cgt       624
Tyr Leu Ala Phe Asn Val Ser Gly Arg Pro Tyr Asp Gly Gly Phe Arg
```

```
                195                 200                 205
tgc cat ttc cac ccc aac gct ccc atc tac aac gac cgc gag cgt ctc    672
Cys His Phe His Pro Asn Ala Pro Ile Tyr Asn Asp Arg Glu Arg Leu
210                 215                 220 cag ata tac atc tcc gac gct ggc atc ctc gcc gtc tgc tac ggt ctc    720
Gln Ile Tyr Ile Ser Asp Ala Gly Ile Leu Ala Val Cys Tyr Gly Leu
225                 230                 235                 240 ttc cgt tac gcc gcc ggc cag gga gtg gcc tcg atg gtc tgc ttc tac    768
Phe Arg Tyr Ala Ala Gly Gln Gly Val Ala Ser Met Val Cys Phe Tyr
                245                 250                 255 gga gtc ccg ctt ctg att gtc aat ggt ttc ctc gtg ttg atc act tac    816
Gly Val Pro Leu Leu Ile Val Asn Gly Phe Leu Val Leu Ile Thr Tyr
                260                 265                 270 ttg cag cac acg cat cct tcc ctg cct cac tac gat tcg tcc gag tgg    864
Leu Gln His Thr His Pro Ser Leu Pro His Tyr Asp Ser Ser Glu Trp
                275                 280                 285 gat tgg ttc agg gga gct ttg gct acc gtt gac aga gac tac gga atc    912
Asp Trp Phe Arg Gly Ala Leu Ala Thr Val Asp Arg Asp Tyr Gly Ile
290                 295                 300 ttg aac aag gtc ttc cac aat att acc gac acg cac gtg gcc cat cat    960
Leu Asn Lys Val Phe His Asn Ile Thr Asp Thr His Val Ala His His
305                 310                 315                 320 ccg ttc tcc acg atg ccg cat tat cac gcg atg gaa gct acc aag gcg   1008
Pro Phe Ser Thr Met Pro His Tyr His Ala Met Glu Ala Thr Lys Ala
                325                 330                 335 ata aag ccg ata ctg gga gag tat tat cag ttc gat ggg acg ccg gtg   1056
Ile Lys Pro Ile Leu Gly Glu Tyr Tyr Gln Phe Asp Gly Thr Pro Val
                340                 345                 350 gtt aag gcg atg tgg agg gag gcg aag gag tgt atc tat gtg gaa ccg   1104
Val Lys Ala Met Trp Arg Glu Ala Lys Glu Cys Ile Tyr Val Glu Pro
                355                 360                 365 gac agg caa ggt gag aag aaa ggt gtg ttc tgg tac aac aat aag tta   1152
Asp Arg Gln Gly Glu Lys Lys Gly Val Phe Trp Tyr Asn Asn Lys Leu
370                 375                 380 tga                                                                1155
```

<210> SEQ ID NO 2
<211> LENGTH: 384
<212> TYPE: PRT
<213> ORGANISM: Brassica napus
<220> FEATURE:
<223> OTHER INFORMATION: Xaa = Phe, Leu, Ile, or Val

<400> SEQUENCE: 2

```
Met Gly Ala Gly Gly Arg Met Gln Val Ser Pro Pro Lys Lys Ser
1               5                   10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Xaa Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110
```

-continued

```
Ser Asp Tyr Gln Trp Leu Asp Thr Val Gly Leu Ile Phe His Ser
        115                 120                 125
Phe Leu Leu Val Pro Tyr Phe Ser Trp Lys Tyr Ser His Arg Ser His
    130                 135                 140
His Ser Asn Thr Gly Ser Leu Glu Arg Asp Glu Val Phe Val Pro Lys
145                 150                 155                 160
Lys Lys Ser Asp Ile Lys Trp Tyr Gly Lys Tyr Leu Asn Asn Pro Leu
                165                 170                 175
Gly Arg Thr Val Met Leu Thr Val Gln Phe Thr Leu Gly Trp Pro Leu
            180                 185                 190
Tyr Leu Ala Phe Asn Val Ser Gly Arg Pro Tyr Asp Gly Phe Arg
        195                 200                 205
Cys His Phe His Pro Asn Ala Pro Ile Tyr Asn Asp Arg Glu Arg Leu
    210                 215                 220
Gln Ile Tyr Ile Ser Asp Ala Gly Ile Leu Ala Val Cys Tyr Gly Leu
225                 230                 235                 240
Phe Arg Tyr Ala Ala Gly Gln Gly Val Ala Ser Met Val Cys Phe Tyr
                245                 250                 255
Gly Val Pro Leu Leu Ile Val Asn Gly Phe Leu Val Leu Ile Thr Tyr
            260                 265                 270
Leu Gln His Thr His Pro Ser Leu Pro His Tyr Asp Ser Ser Glu Trp
        275                 280                 285
Asp Trp Phe Arg Gly Ala Leu Ala Thr Val Asp Arg Asp Tyr Gly Ile
    290                 295                 300
Leu Asn Lys Val Phe His Asn Ile Thr Asp Thr His Val Ala His His
305                 310                 315                 320
Pro Phe Ser Thr Met Pro His Tyr His Ala Met Glu Ala Thr Lys Ala
                325                 330                 335
Ile Lys Pro Ile Leu Gly Glu Tyr Tyr Gln Phe Asp Gly Thr Pro Val
            340                 345                 350
Val Lys Ala Met Trp Arg Glu Ala Lys Glu Cys Ile Tyr Val Glu Pro
        355                 360                 365
Asp Arg Gln Gly Glu Lys Lys Gly Val Phe Trp Tyr Asn Asn Lys Leu
    370                 375                 380
```

<210> SEQ ID NO 3
<211> LENGTH: 1155
<212> TYPE: DNA
<213> ORGANISM: Brassica napus
<220> FEATURE:
<221> NAME/KEY: CDS
<222> LOCATION: (1)...(1152)
<223> OTHER INFORMATION: G to A transversion mutation at nucleotide 316
<220> FEATURE:
<221> NAME/KEY: misc_feature
<222> LOCATION: 205
<223> OTHER INFORMATION: n = a, g, c, or t/u

<400> SEQUENCE: 3

```
atg ggt gca ggt gga aga atg caa gtg tct cct ccc tcc aag aag tct      48
Met Gly Ala Gly Gly Arg Met Gln Val Ser Pro Pro Ser Lys Lys Ser
 1               5                  10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
             20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
         35                  40                  45
```

|  |  |  |  |  |  |  |  |  |  |  |  |  |  |  |  |  |
|---|---|---|---|---|---|---|---|---|---|---|---|---|---|---|---|---|
| atc | cct | cgc | tct | ttc | tcc | tac | ctc | atc | tgg | gac | atc | atc | ata | gcc | tcc | 192 |
| Ile | Pro | Arg | Ser | Phe | Ser | Tyr | Leu | Ile | Trp | Asp | Ile | Ile | Ile | Ala | Ser |  |
|  | 50 |  |  |  | 55 |  |  |  | 60 |  |  |  |  |  |  |  |
| tgc | ttc | tac | tac | ntc | gcc | acc | act | tac | ttc | cct | ctc | ctc | cct | cac | cct | 240 |
| Cys | Phe | Tyr | Tyr | Xaa | Ala | Thr | Thr | Tyr | Phe | Pro | Leu | Leu | Pro | His | Pro |  |
| 65 |  |  |  | 70 |  |  |  |  | 75 |  |  |  |  |  | 80 |  |
| ctc | tcc | tac | ttc | gcc | tgg | cct | ctc | tac | tgg | gcc | tgc | caa | ggg | tgc | gtc | 288 |
| Leu | Ser | Tyr | Phe | Ala | Trp | Pro | Leu | Tyr | Trp | Ala | Cys | Gln | Gly | Cys | Val |  |
|  |  |  |  | 85 |  |  |  |  | 90 |  |  |  |  | 95 |  |  |
| cta | acc | ggc | gtc | tgg | gtc | ata | gcc | cac | aag | tgc | ggc | cac | cac | gcc | ttc | 336 |
| Leu | Thr | Gly | Val | Trp | Val | Ile | Ala | His | Lys | Cys | Gly | His | His | Ala | Phe |  |
|  |  |  | 100 |  |  |  |  | 105 |  |  |  |  | 110 |  |  |  |
| agc | gac | tac | cag | tgg | ctt | gac | gac | acc | gtc | ggt | ctc | atc | ttc | cac | tcc | 384 |
| Ser | Asp | Tyr | Gln | Trp | Leu | Asp | Asp | Thr | Val | Gly | Leu | Ile | Phe | His | Ser |  |
|  |  | 115 |  |  |  |  | 120 |  |  |  |  | 125 |  |  |  |  |
| ttc | ctc | ctc | gtc | cct | tac | ttc | tcc | tgg | aag | tac | agt | cat | cgc | agc | cac | 432 |
| Phe | Leu | Leu | Val | Pro | Tyr | Phe | Ser | Trp | Lys | Tyr | Ser | His | Arg | Ser | His |  |
| 130 |  |  |  |  | 135 |  |  |  |  | 140 |  |  |  |  |  |  |
| cat | tcc | aac | act | ggc | tcc | ctc | gag | aga | gac | gaa | gtg | ttt | gtc | ccc | aag | 480 |
| His | Ser | Asn | Thr | Gly | Ser | Leu | Glu | Arg | Asp | Glu | Val | Phe | Val | Pro | Lys |  |
| 145 |  |  |  |  | 150 |  |  |  |  | 155 |  |  |  |  | 160 |  |
| aag | aag | tca | gac | atc | aag | tgg | tac | ggc | aag | tac | ctc | aac | aac | cct | ttg | 528 |
| Lys | Lys | Ser | Asp | Ile | Lys | Trp | Tyr | Gly | Lys | Tyr | Leu | Asn | Asn | Pro | Leu |  |
|  |  |  |  | 165 |  |  |  |  | 170 |  |  |  |  | 175 |  |  |
| gga | cgc | acc | gtg | atg | tta | acg | gtt | cag | ttc | act | ctc | ggc | tgg | ccg | ttg | 576 |
| Gly | Arg | Thr | Val | Met | Leu | Thr | Val | Gln | Phe | Thr | Leu | Gly | Trp | Pro | Leu |  |
|  |  |  | 180 |  |  |  |  | 185 |  |  |  |  | 190 |  |  |  |
| tac | tta | gcc | ttc | aac | gtc | tcg | gga | aga | cct | tac | gac | ggc | ggc | ttc | cgt | 624 |
| Tyr | Leu | Ala | Phe | Asn | Val | Ser | Gly | Arg | Pro | Tyr | Asp | Gly | Gly | Phe | Arg |  |
|  |  | 195 |  |  |  |  | 200 |  |  |  |  | 205 |  |  |  |  |
| tgc | cat | ttc | cac | ccc | aac | gct | ccc | atc | tac | aac | gac | cgc | gag | cgt | ctc | 672 |
| Cys | His | Phe | His | Pro | Asn | Ala | Pro | Ile | Tyr | Asn | Asp | Arg | Glu | Arg | Leu |  |
| 210 |  |  |  |  | 215 |  |  |  |  | 220 |  |  |  |  |  |  |
| cag | ata | tac | atc | tcc | gac | gct | ggc | atc | ctc | gcc | gtc | tgc | tac | ggt | ctc | 720 |
| Gln | Ile | Tyr | Ile | Ser | Asp | Ala | Gly | Ile | Leu | Ala | Val | Cys | Tyr | Gly | Leu |  |
| 225 |  |  |  |  | 230 |  |  |  |  | 235 |  |  |  |  | 240 |  |
| ttc | cgt | tac | gcc | gcc | ggc | cag | gga | gtg | gcc | tcg | atg | gtc | tgc | ttc | tac | 768 |
| Phe | Arg | Tyr | Ala | Ala | Gly | Gln | Gly | Val | Ala | Ser | Met | Val | Cys | Phe | Tyr |  |
|  |  |  |  | 245 |  |  |  |  | 250 |  |  |  |  | 255 |  |  |
| gga | gtc | ccg | ctt | ctg | att | gtc | aat | ggt | ttc | ctc | gtg | ttg | atc | act | tac | 816 |
| Gly | Val | Pro | Leu | Leu | Ile | Val | Asn | Gly | Phe | Leu | Val | Leu | Ile | Thr | Tyr |  |
|  |  |  | 260 |  |  |  |  | 265 |  |  |  |  | 270 |  |  |  |
| ttg | cag | cac | acg | cat | cct | tcc | ctg | cct | cac | tac | gat | tcg | tcc | gag | tgg | 864 |
| Leu | Gln | His | Thr | His | Pro | Ser | Leu | Pro | His | Tyr | Asp | Ser | Ser | Glu | Trp |  |
|  |  | 275 |  |  |  |  | 280 |  |  |  |  | 285 |  |  |  |  |
| gat | tgg | ttc | agg | gga | gct | ttg | gct | acc | gtt | gac | aga | gac | tac | gga | atc | 912 |
| Asp | Trp | Phe | Arg | Gly | Ala | Leu | Ala | Thr | Val | Asp | Arg | Asp | Tyr | Gly | Ile |  |
| 290 |  |  |  |  | 295 |  |  |  |  | 300 |  |  |  |  |  |  |
| ttg | aac | aag | gtc | ttc | cac | aat | att | acc | gac | acg | cac | gtg | gcc | cat | cat | 960 |
| Leu | Asn | Lys | Val | Phe | His | Asn | Ile | Thr | Asp | Thr | His | Val | Ala | His | His |  |
| 305 |  |  |  |  | 310 |  |  |  |  | 315 |  |  |  |  | 320 |  |
| ccg | ttc | tcc | acg | atg | ccg | cat | tat | cac | gcg | atg | gaa | gct | acc | aag | gcg | 1008 |
| Pro | Phe | Ser | Thr | Met | Pro | His | Tyr | His | Ala | Met | Glu | Ala | Thr | Lys | Ala |  |
|  |  |  |  | 325 |  |  |  |  | 330 |  |  |  |  | 335 |  |  |
| ata | aag | ccg | ata | ctg | gga | gag | tat | tat | cag | ttc | gat | ggg | acg | ccg | gtg | 1056 |
| Ile | Lys | Pro | Ile | Leu | Gly | Glu | Tyr | Tyr | Gln | Phe | Asp | Gly | Thr | Pro | Val |  |
|  |  |  | 340 |  |  |  |  | 345 |  |  |  |  | 350 |  |  |  |
| gtt | aag | gcg | atg | tgg | agg | gag | gcg | aag | gag | tgt | atc | tat | gtg | gaa | ccg | 1104 |
| Val | Lys | Ala | Met | Trp | Arg | Glu | Ala | Lys | Glu | Cys | Ile | Tyr | Val | Glu | Pro |  |
|  |  | 355 |  |  |  |  | 360 |  |  |  |  | 365 |  |  |  |  |

```
gac agg caa ggt gag aag aaa ggt gtg ttc tgg tac aac aat aag tta    1152
Asp Arg Gln Gly Glu Lys Lys Gly Val Phe Trp Tyr Asn Asn Lys Leu
    370                 375                 380 tga                                                                1155
```

<210> SEQ ID NO 4
<211> LENGTH: 384
<212> TYPE: PRT
<213> ORGANISM: Brassica napus
<220> FEATURE:
<223> OTHER INFORMATION: Xaa = Phe, Leu, Ile, or Val

<400> SEQUENCE: 4

```
Met Gly Ala Gly Gly Arg Met Gln Val Ser Pro Pro Ser Lys Lys Ser
  1               5                  10                  15

Glu Thr Asp Thr Ile Lys Arg Val Pro Cys Glu Thr Pro Pro Phe Thr
                 20                  25                  30

Val Gly Glu Leu Lys Lys Ala Ile Pro Pro His Cys Phe Lys Arg Ser
             35                  40                  45

Ile Pro Arg Ser Phe Ser Tyr Leu Ile Trp Asp Ile Ile Ala Ser
     50                  55                  60

Cys Phe Tyr Tyr Xaa Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                 85                  90                  95

Leu Thr Gly Val Trp Val Ile Ala His Lys Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Ser His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Arg
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Gly Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Phe Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Pro Phe Ser Thr Met Pro His Tyr His Ala Met Glu Ala Thr Lys Ala
                325                 330                 335
```

```
Ile Lys Pro Ile Leu Gly Glu Tyr Tyr Gln Phe Asp Gly Thr Pro Val
        340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
        370                 375                 380

<210> SEQ ID NO 5
<211> LENGTH: 1155
<212> TYPE: DNA
<213> ORGANISM: Brassica napus
<220> FEATURE:
<221> NAME/KEY: CDS
<222> LOCATION: (1)...(1152)
<223> OTHER INFORMATION: Wild type Fad2

<400> SEQUENCE: 5
```

| | | | | | | | | | | | | | | | | |
|---|---|---|---|---|---|---|---|---|---|---|---|---|---|---|---|---|
| atg | ggt | gca | ggt | gga | aga | atg | caa | gtg | tct | cct | ccc | tcc | aaa | aag | tct | 48 |
| Met | Gly | Ala | Gly | Gly | Arg | Met | Gln | Val | Ser | Pro | Pro | Ser | Lys | Lys | Ser | |
| 1 | | | | 5 | | | | | 10 | | | | | 15 | | |
| gaa | acc | gac | aac | atc | aag | cgc | gta | ccc | tgc | gag | aca | ccg | ccc | ttc | act | 96 |
| Glu | Thr | Asp | Asn | Ile | Lys | Arg | Val | Pro | Cys | Glu | Thr | Pro | Pro | Phe | Thr | |
| | | | 20 | | | | | 25 | | | | | 30 | | | |
| gtc | gga | gaa | ctc | aag | aaa | gca | atc | cca | ccg | cac | tgt | ttc | aaa | cgc | tcg | 144 |
| Val | Gly | Glu | Leu | Lys | Lys | Ala | Ile | Pro | Pro | His | Cys | Phe | Lys | Arg | Ser | |
| | 35 | | | | | 40 | | | | | 45 | | | | | |
| atc | cct | cgc | tct | ttc | tcc | tac | ctc | atc | tgg | gac | atc | atc | ata | gcc | tcc | 192 |
| Ile | Pro | Arg | Ser | Phe | Ser | Tyr | Leu | Ile | Trp | Asp | Ile | Ile | Ile | Ala | Ser | |
| 50 | | | | | 55 | | | | | 60 | | | | | | |
| tgc | ttc | tac | tac | gtc | gcc | acc | act | tac | ttc | cct | ctc | ctc | cct | cac | cct | 240 |
| Cys | Phe | Tyr | Tyr | Val | Ala | Thr | Thr | Tyr | Phe | Pro | Leu | Leu | Pro | His | Pro | |
| 65 | | | | | 70 | | | | | 75 | | | | | 80 | |
| ctc | tcc | tac | ttc | gcc | tgg | cct | ctc | tac | tgg | gcc | tgc | cag | ggc | tgc | gtc | 288 |
| Leu | Ser | Tyr | Phe | Ala | Trp | Pro | Leu | Tyr | Trp | Ala | Cys | Gln | Gly | Cys | Val | |
| | | | | 85 | | | | | 90 | | | | | 95 | | |
| cta | acc | ggc | gtc | tgg | gtc | ata | gcc | cac | gag | tgc | ggc | cac | cac | gcc | ttc | 336 |
| Leu | Thr | Gly | Val | Trp | Val | Ile | Ala | His | Glu | Cys | Gly | His | His | Ala | Phe | |
| | | | 100 | | | | | 105 | | | | | 110 | | | |
| agc | gac | tac | cag | tgg | ctg | gac | gac | acc | gtc | ggc | ctc | atc | ttc | cac | tcc | 384 |
| Ser | Asp | Tyr | Gln | Trp | Leu | Asp | Asp | Thr | Val | Gly | Leu | Ile | Phe | His | Ser | |
| | 115 | | | | | 120 | | | | | 125 | | | | | |
| ttc | ctc | ctc | gtc | cct | tac | ttc | tcc | tgg | aag | tac | agt | cat | cga | cgc | cac | 432 |
| Phe | Leu | Leu | Val | Pro | Tyr | Phe | Ser | Trp | Lys | Tyr | Ser | His | Arg | Arg | His | |
| 130 | | | | | 135 | | | | | 140 | | | | | | |
| cat | tcc | aac | act | ggc | tcc | ctc | gag | aga | gac | gaa | gtg | ttt | gtc | ccc | aag | 480 |
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |
| aag | aag | tca | gac | atc | aag | tgg | tac | ggc | aag | tac | ctc | aac | aac | cct | ttg | 528 |
| Lys | Lys | Ser | Asp | Ile | Lys | Trp | Tyr | Gly | Lys | Tyr | Leu | Asn | Asn | Pro | Leu | |
| | | | | 165 | | | | | 170 | | | | | 175 | | |
| gga | cgc | acc | gtg | atg | tta | acg | gtt | cag | ttc | act | ctc | ggc | tgg | cct | ttg | 576 |
| Gly | Arg | Thr | Val | Met | Leu | Thr | Val | Gln | Phe | Thr | Leu | Gly | Trp | Pro | Leu | |
| | | | 180 | | | | | 185 | | | | | 190 | | | |
| tac | tta | gcc | ttc | aac | gtc | tcg | ggg | aga | cct | tac | gac | ggc | ggc | ttc | gct | 624 |
| Tyr | Leu | Ala | Phe | Asn | Val | Ser | Gly | Arg | Pro | Tyr | Asp | Gly | Gly | Phe | Ala | |
| | | 195 | | | | | 200 | | | | | 205 | | | | |
| tgc | cat | ttc | cac | ccc | aac | gct | ccc | atc | tac | aac | gac | cgc | gag | cgt | ctc | 672 |
| Cys | His | Phe | His | Pro | Asn | Ala | Pro | Ile | Tyr | Asn | Asp | Arg | Glu | Arg | Leu | |
| | 210 | | | | | 215 | | | | | 220 | | | | | |
| cag | ata | tac | atc | tcc | gac | gct | ggc | atc | ctc | gcc | gtc | tgc | tac | ggt | ctc | 720 |

```
Gln Ile Tyr Ile Ser Asp Ala Gly Ile Leu Ala Val Cys Tyr Gly Leu
225                 230                 235                 240 tac cgc tac gct gct gtc caa gga gtt gcc tcg atg gtc tgc ttc tac    768
Tyr Arg Tyr Ala Ala Val Gln Gly Val Ala Ser Met Val Cys Phe Tyr
                    245                 250                 255 gga gtt ccg ctt ctg att gtc aat ggg tta gtt ttg atc act tac    816
Gly Val Pro Leu Leu Ile Val Asn Gly Phe Leu Val Leu Ile Thr Tyr
            260                 265                 270 ttg cag cac acg cat cct tcc ctg cct cac tat gac tcg tct gag tgg    864
Leu Gln His Thr His Pro Ser Leu Pro His Tyr Asp Ser Ser Glu Trp
        275                 280                 285 gat tgg ttg agg gga gct ttg gcc acc gtt gac aga gac tac gga atc    912
Asp Trp Leu Arg Gly Ala Leu Ala Thr Val Asp Arg Asp Tyr Gly Ile
    290                 295                 300 ttg aac aag gtc ttc cac aat atc acg gac acg cac gtg gcg cat cac    960
Leu Asn Lys Val Phe His Asn Ile Thr Asp Thr His Val Ala His His
305                 310                 315                 320 ctg ttc tcg acc atg ccg cat tat cat gcg atg gaa gct acg aag gcg   1008
Leu Phe Ser Thr Met Pro His Tyr His Ala Met Glu Ala Thr Lys Ala
                325                 330                 335 ata aag ccg ata ctg gga gag tat tat cag ttg cat ggg acg ccg gtg   1056
Ile Lys Pro Ile Leu Gly Glu Tyr Tyr Gln Leu His Gly Thr Pro Val
            340                 345                 350 gtt aag gcg atg tgg agg gag gcg aag gag tgt atc tat gtg gaa ccg   1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta   1152
Asp Arg Gln Gly Glu Lys Lys Gly Val Phe Trp Tyr Asn Asn Lys Leu
    370                 375                 380 tga                                                               1155

<210> SEQ ID NO 6
<211> LENGTH: 384
<212> TYPE: PRT
<213> ORGANISM: Brassica napus

<400> SEQUENCE: 6

Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160
```

```
Lys Lys Ser Asp Ile Lys Trp Tyr Gly Lys Tyr Leu Asn Asn Pro Leu
            165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
            210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
            245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
            325                 330                 335

Ile Lys Pro Ile Leu Gly Glu Tyr Tyr Gln Leu His Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380

<210> SEQ ID NO 7
<211> LENGTH: 1155
<212> TYPE: DNA
<213> ORGANISM: Brassica napus
<220> FEATURE:
<221> NAME/KEY: CDS
<222> LOCATION: (1)...(1152)
<223> OTHER INFORMATION: T to A transversion mutation at nucleotide 515

<400> SEQUENCE: 7 atg ggt gca ggt gga aga atg caa gtg tct cct ccc tcc aaa aag tct    48
Met Gly Ala Gly Gly Arg Met Gln Val Ser Pro Pro Ser Lys Lys Ser
 1               5                  10                  15 gaa acc gac aac atc aag cgc gta ccc tgc gag aca ccg ccc ttc act    96
Glu Thr Asp Asn Ile Lys Arg Val Pro Cys Glu Thr Pro Pro Phe Thr
             20                  25                  30 gtc gga gaa ctc aag aaa gca atc cca ccg cac tgt ttc aaa cgc tcg   144
Val Gly Glu Leu Lys Lys Ala Ile Pro Pro His Cys Phe Lys Arg Ser
         35                  40                  45 atc cct cgc tct ttc tcc tac ctc atc tgg gac atc ata gcc tcc       192
Ile Pro Arg Ser Phe Ser Tyr Leu Ile Trp Asp Ile Ile Ala Ser
     50                  55                  60 tgc ttc tac tac gtc gcc acc act tac ttc cct ctc ctc cct cac cct   240
Cys Phe Tyr Tyr Val Ala Thr Thr Tyr Phe Pro Leu Leu Pro His Pro
 65                  70                  75                  80 ctc tcc tac ttc gcc tgg cct ctc tac tgg gcc tgc cag ggc tgc gtc   288
Leu Ser Tyr Phe Ala Trp Pro Leu Tyr Trp Ala Cys Gln Gly Cys Val
                 85                  90                  95 cta acc ggc gtc tgg gtc ata gcc cac gag tgc ggc cac cac gcc ttc   336
```

-continued

```
                Leu Thr Gly Val Trp Val Ile Ala His Glu Cys Gly His His Ala Phe
                                100                 105                 110 agc gac tac cag tgg ctg gac gac acc gtc ggc ctc atc ttc cac tcc            384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac            432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag            480
His Ser Asn Thr Gly Ser Leu Glu Arg Asp Glu Val Phe Val Pro Lys
145                 150                 155                 160 aag aag tca gac atc aag tgg tac ggc aag tac cac aac aac cct ttg            528
Lys Lys Ser Asp Ile Lys Trp Tyr Gly Lys Tyr His Asn Asn Pro Leu
                165                 170                 175 gga cgc acc gtg atg tta acg gtt cag ttc act ctc ggc tgg cct ttg            576
Gly Arg Thr Val Met Leu Thr Val Gln Phe Thr Leu Gly Trp Pro Leu
            180                 185                 190 tac tta gcc ttc aac gtc tcg ggg aga cct tac gac ggc ggc ttc gct            624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc            672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc            720
Gln Ile Tyr Ile Ser Asp Ala Gly Ile Leu Ala Val Cys Tyr Gly Leu
225                 230                 235                 240 tac cgc tac gct gct gtc caa gga gtt gcc tcg atg gtc tgc ttc tac            768
Tyr Arg Tyr Ala Ala Val Gln Gly Val Ala Ser Met Val Cys Phe Tyr
                245                 250                 255 gga gtt ccg ctt ctg att gtc aat ggg ttc tta gtt ttg atc act tac            816
Gly Val Pro Leu Leu Ile Val Asn Gly Phe Leu Val Leu Ile Thr Tyr
            260                 265                 270 ttg cag cac acg cat cct tcc ctg cct cac tat gac tcg tct gag tgg            864
Leu Gln His Thr His Pro Ser Leu Pro His Tyr Asp Ser Ser Glu Trp
        275                 280                 285 gat tgg ttg agg gga gct ttg gcc acc gtt gac aga gac tac gga atc            912
Asp Trp Leu Arg Gly Ala Leu Ala Thr Val Asp Arg Asp Tyr Gly Ile
    290                 295                 300 ttg aac aag gtc ttc cac aat atc acg gac acg cac gtg gcg cat cac            960
Leu Asn Lys Val Phe His Asn Ile Thr Asp Thr His Val Ala His His
305                 310                 315                 320 ctg ttc tcg acc atg ccg cat tat cat gcg atg gaa gct acg aag gcg           1008
Leu Phe Ser Thr Met Pro His Tyr His Ala Met Glu Ala Thr Lys Ala
                325                 330                 335 ata aag ccg ata ctg gga gag tat tat cag ttg cat ggg acg ccg gtg           1056
Ile Lys Pro Ile Leu Gly Glu Tyr Tyr Gln Leu His Gly Thr Pro Val
            340                 345                 350 gtt aag gcg atg tgg agg gag gcg aag gag tgt atc tat gtg gaa ccg           1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta           1152
Asp Arg Gln Gly Glu Lys Lys Gly Val Phe Trp Tyr Asn Asn Lys Leu
    370                 375                 380 tga                                                                        1155
```

<210> SEQ ID NO 8
<211> LENGTH: 384
<212> TYPE: PRT
<213> ORGANISM: Brassica napus

<400> SEQUENCE: 8

```
Met Gly Ala Gly Gly Arg Met Gln Val Ser Pro Ser Lys Lys Ser
 1               5                  10                  15

Glu Thr Asp Asn Ile Lys Arg Val Pro Cys Glu Thr Pro Pro Phe Thr
                 20                  25                  30

Val Gly Glu Leu Lys Lys Ala Ile Pro Pro His Cys Phe Lys Arg Ser
             35                  40                  45

Ile Pro Arg Ser Phe Ser Tyr Leu Ile Trp Asp Ile Ile Ala Ser
     50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                 85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr His Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
            210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Leu His Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380
```

<210> SEQ ID NO 9
<211> LENGTH: 1155
<212> TYPE: DNA
<213> ORGANISM: Brassica napus

```
<220> FEATURE:
<221> NAME/KEY: CDS
<222> LOCATION: (1)...(1152)

<400> SEQUENCE: 9 atg ggt gca ggt gga aga atg caa gtg tct cct ccc tcc aaa aag tct      48
Met Gly Ala Gly Gly Arg Met Gln Val Ser Pro Pro Ser Lys Lys Ser
 1               5                  10                  15 gaa acc gac aac atc aag cgc gta ccc tgc gag aca ccg ccc ttc act      96
Glu Thr Asp Asn Ile Lys Arg Val Pro Cys Glu Thr Pro Pro Phe Thr
             20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
         35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
     50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
 65                  70                  75                  80 ctc tcc tac ttc gcc tgg cct ctc tac tgg gcc tgc cag ggc tgc gtc     288
Leu Ser Tyr Phe Ala Trp Pro Leu Tyr Trp Ala Cys Gln Gly Cys Val
                 85                  90                  95 cta acc ggc gtc tgg gtc ata gcc cac gag tgc ggc cac cac gcc ttc     336
Leu Thr Gly Val Trp Val Ile Ala His Glu Cys Gly His His Ala Phe
            100                 105                 110 agc gac tac cag tgg ctg gac gac acc gtc ggc ctc atc ttc cac tcc     384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag     480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg     528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg cct ttg     576
Gly Arg Thr Val Met Leu Thr Val Gln Phe Thr Leu Gly Trp Pro Leu
            180                 185                 190 tac tta gcc ttc aac gtc tcg ggg aga cct tac gac ggc ggc ttc gct     624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgt gag cgt ctc     672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc     720
Gln Ile Tyr Ile Ser Asp Ala Gly Ile Leu Ala Val Cys Tyr Gly Leu
225                 230                 235                 240 tac cgc tac gct gct gtc caa gga gtt gcc tcg atg gtc tgc ttc tac     768
Tyr Arg Tyr Ala Ala Val Gln Gly Val Ala Ser Met Val Cys Phe Tyr
                245                 250                 255 gga gtt cct ctt ctg att gtc aac ggg ttc tta gtt ttg atc act tac     816
Gly Val Pro Leu Leu Ile Val Asn Gly Phe Leu Val Leu Ile Thr Tyr
            260                 265                 270 ttg cag cac acg cat cct tcc ctg cct cac tat gac tcg tct gag tgg     864
Leu Gln His Thr His Pro Ser Leu Pro His Tyr Asp Ser Ser Glu Trp
        275                 280                 285 gat tgg ttg agg gga gct ttg gcc acc gtt gac aga gac tac gga atc     912
Asp Trp Leu Arg Gly Ala Leu Ala Thr Val Asp Arg Asp Tyr Gly Ile
```

```
Asp Trp Leu Arg Gly Ala Leu Ala Thr Val Asp Arg Asp Tyr Gly Ile
    290                 295                 300 ttg aac aag gtc ttc cac aat atc acg gac acg cac gtg gcg cat cac      960
Leu Asn Lys Val Phe His Asn Ile Thr Asp Thr His Val Ala His His
305                 310                 315                 320 ctg ttc tcg acc atg ccg cat tat cat gcg atg gaa gct acg aag gcg     1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta     1152
Asp Arg Gln Gly Glu Lys Lys Gly Val Phe Trp Tyr Asn Asn Lys Leu
    370                 375                 380 tga                                                                  1155

<210> SEQ ID NO 10
<211> LENGTH: 384
<212> TYPE: PRT
<213> ORGANISM: Brassica napus

<400> SEQUENCE: 10

Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
```

```
                    245                 250                 255
Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380

<210> SEQ ID NO 11
<211> LENGTH: 1155
<212> TYPE: DNA
<213> ORGANISM: Brassica napus
<220> FEATURE:
<221> NAME/KEY: CDS
<222> LOCATION: (1)...(1152)

<400> SEQUENCE: 11 atg ggt gca ggt gga aga atg caa gtg tct cct ccc tcc aaa aag tct      48
Met Gly Ala Gly Gly Arg Met Gln Val Ser Pro Pro Ser Lys Lys Ser
 1               5                  10                  15 gaa acc gac aac atc aag cgc gta ccc tgc gag aca ccg ccc ttc act      96
Glu Thr Asp Asn Ile Lys Arg Val Pro Cys Glu Thr Pro Pro Phe Thr
            20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
        35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
    50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc cag ggc tgc gtc     288
Leu Ser Tyr Phe Ala Trp Pro Leu Tyr Trp Ala Cys Gln Gly Cys Val
                85                  90                  95 cta acc ggc gtc tgg gtc ata gcc cac aag tgc ggc cac cac gcc ttc     336
Leu Thr Gly Val Trp Val Ile Ala His Lys Cys Gly His His Ala Phe
            100                 105                 110 agc gac tac cag tgg ctg gac gac acc gtc ggc ctc atc ttc cac tcc     384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag     480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg     528
Lys Lys Ser Asp Ile Lys Trp Tyr Gly Lys Tyr Leu Asn Asn Pro Leu
```

-continued

```
                       165                 170                 175
gga cgc acc gtg atg tta acg gtt cag ttc act ctc ggc tgg cct ttg      576
Gly Arg Thr Val Met Leu Thr Val Gln Phe Thr Leu Gly Trp Pro Leu
            180                 185                 190 tac tta gcc ttc aac gtc tcg ggg aga cct tac gac ggc ggc ttc gct      624
Tyr Leu Ala Phe Asn Val Ser Gly Arg Pro Tyr Asp Gly Gly Phe Ala
                195                 200                 205 tgc cat ttc cac ccc aac gct ccc atc tac aac gac cgt gag cgt ctc      672
Cys His Phe His Pro Asn Ala Pro Ile Tyr Asn Asp Arg Glu Arg Leu
        210                 215                 220 cag ata tac atc tcc gac gct ggc atc ctc gcc gtc tgc tac ggt ctc      720
Gln Ile Tyr Ile Ser Asp Ala Gly Ile Leu Ala Val Cys Tyr Gly Leu
225                 230                 235                 240 tac cgc tac gct gct gtc caa gga gtt gcc tcg atg gtc tgc ttc tac      768
Tyr Arg Tyr Ala Ala Val Gln Gly Val Ala Ser Met Val Cys Phe Tyr
                245                 250                 255 gga gtt cct ctt ctg att gtc aac ggg ttc tta gtt ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tat gac tcg tct gag tgg      864
Leu Gln His Thr His Pro Ser Leu Pro His Tyr Asp Ser Ser Glu Trp
        275                 280                 285 gat tgg ttg agg gga gct ttg gcc acc gtt gac aga gac tac gga atc      912
Asp Trp Leu Arg Gly Ala Leu Ala Thr Val Asp Arg Asp Tyr Gly Ile
290                 295                 300 ttg aac aag gtc ttc cac aat atc acg gac acg cac gtg gcg cat cac      960
Leu Asn Lys Val Phe His Asn Ile Thr Asp Thr His Val Ala His His
305                 310                 315                 320 ctg ttc tcg acc atg ccg cat tat cat gcg atg gaa gct acg aag gcg     1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta     1152
Asp Arg Gln Gly Glu Lys Lys Gly Val Phe Trp Tyr Asn Asn Lys Leu
370                 375                 380 tga                                                                 1155
```

<210> SEQ ID NO 12
<211> LENGTH: 384
<212> TYPE: PRT
<213> ORGANISM: Brassica napus

<400> SEQUENCE: 12

```
Met Gly Ala Gly Gly Arg Met Gln Val Ser Pro Ser Lys Lys Ser
 1               5                  10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ile Ala Ser
        50                  55                  60

Cys Phe Tyr Tyr Val Ala Thr Thr Tyr Phe Pro Leu Leu Pro His Pro
65                  70                  75                  80
```

```
Leu Ser Tyr Phe Ala Trp Pro Leu Tyr Trp Ala Cys Gln Gly Cys Val
                85                  90                  95

Leu Thr Gly Val Trp Val Ile Ala His Lys Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
370                 375                 380

<210> SEQ ID NO 13
<211> LENGTH: 1155
<212> TYPE: DNA
<213> ORGANISM: Brassica napus
<220> FEATURE:
<221> NAME/KEY: CDS
<222> LOCATION: (1)...(1152)

<400> SEQUENCE: 13 atg ggt gca ggt gga aga atg caa gtg tct cct ccc tcc aag aag tct      48
Met Gly Ala Gly Gly Arg Met Gln Val Ser Pro Pro Ser Lys Lys Ser
 1               5                  10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
                20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
            35                  40                  45
```

-continued

| | | |
|---|---|---|
| atc cct cgc tct ttc tcc tac ctc atc tgg gac atc atc ata gcc tcc<br>Ile Pro Arg Ser Phe Ser Tyr Leu Ile Trp Asp Ile Ile Ile Ala Ser<br>50                           55                     60 | 192 |
| tgc ttc tac tac gtc gcc acc act tac ttc cct ctc ctc cct cac cct<br>Cys Phe Tyr Tyr Val Ala Thr Thr Tyr Phe Pro Leu Leu Pro His Pro<br>65                         70                      75                     80 | 240 |
| ctc tcc tac ttc gcc tgg cct ctc tac tgg gcc tgc caa ggg tgc gtc<br>Leu Ser Tyr Phe Ala Trp Pro Leu Tyr Trp Ala Cys Gln Gly Cys Val<br>85                     90                   95 | 288 |
| cta acc ggc gtc tgg gtc ata gcc cac gag tgc ggc cac cac gcc ttc<br>Leu Thr Gly Val Trp Val Ile Ala His Glu Cys Gly His His Ala Phe<br>100                        105                     110 | 336 |
| agc gac tac cag tgg ctt gac gac acc gtc ggt ctc atc ttc cac tcc<br>Ser Asp Tyr Gln Trp Leu Asp Asp Thr Val Gly Leu Ile Phe His Ser<br>115                     120                   125 | 384 |
| ttc ctc ctc gtc cct tac ttc tcc tgg aag tac agt cat cga cgc cac<br>Phe Leu Leu Val Pro Tyr Phe Ser Trp Lys Tyr Ser His Arg Arg His<br>130                     135                   140 | 432 |
| cat tcc aac act ggc tcc ctc gag aga gac gaa gtg ttt gtc ccc aag<br>His Ser Asn Thr Gly Ser Leu Glu Arg Asp Glu Val Phe Val Pro Lys<br>145                   150                   155                   160 | 480 |
| aag aag tca gac atc aag tgg tac ggc aag tac ctc aac aac cct ttg<br>Lys Lys Ser Asp Ile Lys Trp Tyr Gly Lys Tyr Leu Asn Asn Pro Leu<br>                   165                   170                   175 | 528 |
| gga cgc acc gtg atg tta acg gtt cag ttc act ctc ggc tgg ccg ttg<br>Gly Arg Thr Val Met Leu Thr Val Gln Phe Thr Leu Gly Trp Pro Leu<br>                   180                   185                   190 | 576 |
| tac tta gcc ttc aac gtc tcg gga aga cct tac gac ggc ggc ttc gct<br>Tyr Leu Ala Phe Asn Val Ser Gly Arg Pro Tyr Asp Gly Gly Phe Ala<br>                   195                   200                   205 | 624 |
| tgc cat ttc cac ccc aac gct ccc atc tac aac gac cgc gag cgt ctc<br>Cys His Phe His Pro Asn Ala Pro Ile Tyr Asn Asp Arg Glu Arg Leu<br>210                     215                   220 | 672 |
| cag ata tac atc tcc gac gct ggc atc ctc gcc gtc tgc tac ggt ctc<br>Gln Ile Tyr Ile Ser Asp Ala Gly Ile Leu Ala Val Cys Tyr Gly Leu<br>225                     230                   235                   240 | 720 |
| ttc cgt tac gcc gcc gcg cag gga gtg gcc tcg atg gtc tgc ttc tac<br>Phe Arg Tyr Ala Ala Ala Gln Gly Val Ala Ser Met Val Cys Phe Tyr<br>                   245                   250                   255 | 768 |
| gga gtc ccg ctt ctg att gtc aat ggt ttc ctc gtg ttg atc act tac<br>Gly Val Pro Leu Leu Ile Val Asn Gly Phe Leu Val Leu Ile Thr Tyr<br>                   260                   265                   270 | 816 |
| ttg cag cac acg cat cct tcc ctg cct cac tac gat tcg tcc gag tgg<br>Leu Gln His Thr His Pro Ser Leu Pro His Tyr Asp Ser Ser Glu Trp<br>                   275                   280                   285 | 864 |
| gat tgg ttg agg gga gct ttg gct acc gtt gac aga gac tac gga atc<br>Asp Trp Leu Arg Gly Ala Leu Ala Thr Val Asp Arg Asp Tyr Gly Ile<br>290                     295                   300 | 912 |
| ttg aac aag gtc ttc cac aat att acc gac acg cac gtg gcg cat cat<br>Leu Asn Lys Val Phe His Asn Ile Thr Asp Thr His Val Ala His His<br>305                     310                   315                   320 | 960 |
| ctg ttc tcc acg atg ccg cat tat cac gcg atg gaa gct acc aag gcg<br>Leu Phe Ser Thr Met Pro His Tyr His Ala Met Glu Ala Thr Lys Ala<br>                   325                   330                   335 | 1008 |
| ata aag ccg ata ctg gga gag tat tat cag ttc gat ggg acg ccg gtg<br>Ile Lys Pro Ile Leu Gly Glu Tyr Tyr Gln Phe Asp Gly Thr Pro Val<br>                   340                   345                   350 | 1056 |
| gtt aag gcg atg tgg agg gag gcg aag gag tgt atc tat gtg gaa ccg<br>Val Lys Ala Met Trp Arg Glu Ala Lys Glu Cys Ile Tyr Val Glu Pro | 1104 |

```
              355                 360                 365
gac agg caa ggt gag aag aaa ggt gtg ttc tgg tac aac aat aag tta    1152
Asp Arg Gln Gly Glu Lys Lys Gly Val Phe Trp Tyr Asn Asn Lys Leu
    370                 375                 380 tga                                                                1155
```

<210> SEQ ID NO 14
<211> LENGTH: 384
<212> TYPE: PRT
<213> ORGANISM: Brassica napus

<400> SEQUENCE: 14

```
Met Gly Ala Gly Gly Arg Met Gln Val Ser Pro Ser Lys Lys Ser
  1               5                  10                  15

Glu Thr Asp Thr Ile Lys Arg Val Pro Cys Glu Thr Pro Phe Thr
                 20                  25                  30

Val Gly Glu Leu Lys Lys Ala Ile Pro Pro His Cys Phe Lys Arg Ser
                 35                  40                  45

Ile Pro Arg Ser Phe Ser Tyr Leu Ile Trp Asp Ile Ile Ala Ser
     50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                 85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
                115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Asp Gly Gly Phe Ala
                195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
                275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335
```

```
Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
        370                 375                 380

<210> SEQ ID NO 15
<211> LENGTH: 1155
<212> TYPE: DNA
<213> ORGANISM: Brassica napus
<220> FEATURE:
<221> NAME/KEY: CDS
<222> LOCATION: (1)...(1152)

<400> SEQUENCE: 15 atg ggt gca ggt gga aga atg caa gtg tct cct ccc tcc aag aag tct      48
Met Gly Ala Gly Gly Arg Met Gln Val Ser Pro Pro Ser Lys Lys Ser
 1               5                  10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
                 20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
             35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
         50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
 65                  70                  75                  80 ctc tcc tac ttc gcc tgg cct ctc tac tgg gcc tgc caa ggg tgc gtc     288
Leu Ser Tyr Phe Ala Trp Pro Leu Tyr Trp Ala Cys Gln Gly Cys Val
                 85                  90                  95 cta acc ggc gtc tgg gtc ata gcc cac gag tgc ggc cac cac gcc ttc     336
Leu Thr Gly Val Trp Val Ile Ala His Glu Cys Gly His His Ala Phe
            100                 105                 110 agc gac tac cag tgg ctt gac gac acc gtc ggt ctc atc ttc cac tcc     384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag     480
His Ser Asn Thr Gly Ser Leu Glu Arg Asp Glu Val Phe Val Pro Lys
145                 150                 155                 160 aag aag tca gac atc aag tgg tac ggc aag tac cac aac aac cct ttg     528
Lys Lys Ser Asp Ile Lys Trp Tyr Gly Lys Tyr His Asn Asn Pro Leu
                165                 170                 175 gga cgc acc gtg atg tta acg gtt cag ttc act ctc ggc tgg ccg ttg     576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc gct     624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc     672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc     720
Gln Ile Tyr Ile Ser Asp Ala Gly Ile Leu Ala Val Cys Tyr Gly Leu
225                 230                 235                 240
```

```
ttc cgt tac gcc gcc gcg cag gga gtg gcc tcg atg gtc tgc ttc tac    768
Phe Arg Tyr Ala Ala Ala Gln Gly Val Ala Ser Met Val Cys Phe Tyr
                245                 250                 255 gga gtc ccg ctt ctg att gtc aat ggt ttc ctc gtg ttg atc act tac    816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg    864
Leu Gln His Thr His Pro Ser Leu Pro His Tyr Asp Ser Ser Glu Trp
        275                 280                 285 gat tgg ttg agg gga gct ttg gct acc gtt gac aga gac tac gga atc    912
Asp Trp Leu Arg Gly Ala Leu Ala Thr Val Asp Arg Asp Tyr Gly Ile
    290                 295                 300 ttg aac aag gtc ttc cac aat att acc gac acg cac gtg gcg cat cat    960
Leu Asn Lys Val Phe His Asn Ile Thr Asp Thr His Val Ala His His
305                 310                 315                 320 ctg ttc tcc acg atg ccg cat tat cac gcg atg gaa gct acc aag gcg   1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg   1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg   1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta   1152
Asp Arg Gln Gly Glu Lys Lys Gly Val Phe Trp Tyr Asn Asn Lys Leu
    370                 375                 380 tga                                                                1155
```

<210> SEQ ID NO 16
<211> LENGTH: 384
<212> TYPE: PRT
<213> ORGANISM: Brassica napus

<400> SEQUENCE: 16

```
Met Gly Ala Gly Gly Arg Met Gln Val Ser Pro Ser Lys Lys Ser
 1               5                  10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr His Asn Asn Pro Leu
                165                 170                 175
```

```
Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
        210                 215                 220

Gln Ile Tyr Ile Ser Asp Ala Gly Ile Leu Ala Val Cys Tyr Gly Leu
225                 230                 235                 240

Phe Arg Tyr Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
                275                 280                 285

Asp Trp Leu Arg Gly Ala Leu Ala Thr Val Asp Arg Asp Tyr Gly Ile
                290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
                370                 375                 380

<210> SEQ ID NO 17
<211> LENGTH: 1155
<212> TYPE: DNA
<213> ORGANISM: Brassica napus
<220> FEATURE:
<221> NAME/KEY: CDS
<222> LOCATION: (1)...(1152)

<400> SEQUENCE: 17 atg ggt gca ggt gga aga atg caa gtg tct cct ccc tcc aag aag tct      48
Met Gly Ala Gly Gly Arg Met Gln Val Ser Pro Pro Ser Lys Lys Ser
 1               5                  10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
                20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
            35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
        50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc caa ggg tgc gtc     288
Leu Ser Tyr Phe Ala Trp Pro Leu Tyr Trp Ala Cys Gln Gly Cys Val
                85                  90                  95 cta acc ggc gtc tgg gtc ata gcc cac gag tgc ggc cac cac gcc ttc     336
Leu Thr Gly Val Trp Val Ile Ala His Glu Cys Gly His His Ala Phe
                100                 105                 110
```

| | | | | | | | | | | | | | | | | |
|---|---|---|---|---|---|---|---|---|---|---|---|---|---|---|---|---|
| agc | gac | tac | cag | tgg | ctt | gac | gac | acc | gtc | ggt | ctc | atc | ttc | cac | tcc | 384 |
| Ser | Asp | Tyr | Gln | Trp | Leu | Asp | Asp | Thr | Val | Gly | Leu | Ile | Phe | His | Ser | |
| | | 115 | | | | 120 | | | | 125 | | | | | | |
| ttc | ctc | ctc | gtc | cct | tac | ttc | tcc | tgg | aag | tac | agt | cat | cga | cgc | cac | 432 |
| Phe | Leu | Leu | Val | Pro | Tyr | Phe | Ser | Trp | Lys | Tyr | Ser | His | Arg | Arg | His | |
| | 130 | | | | | 135 | | | | | 140 | | | | | |
| cat | tcc | aac | act | ggc | tcc | ctc | gag | aga | gac | gaa | gtg | ttt | gtc | ccc | aag | 480 |
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |
| aag | aag | tca | gac | atc | aag | tgg | tac | ggc | aag | tac | ctc | aac | aac | cct | ttg | 528 |
| Lys | Lys | Ser | Asp | Ile | Lys | Trp | Tyr | Gly | Lys | Tyr | Leu | Asn | Asn | Pro | Leu | |
| | | | | 165 | | | | | 170 | | | | | 175 | | |
| gga | cgc | acc | gtg | atg | tta | acg | gtt | cag | ttc | act | ctc | ggc | tgg | ccg | ttg | 576 |
| Gly | Arg | Thr | Val | Met | Leu | Thr | Val | Gln | Phe | Thr | Leu | Gly | Trp | Pro | Leu | |
| | | | | 180 | | | | | 185 | | | | | 190 | | |
| tac | tta | gcc | ttc | aac | gtc | tcg | gga | aga | cct | tac | gac | ggc | ggc | ttc | gct | 624 |
| Tyr | Leu | Ala | Phe | Asn | Val | Ser | Gly | Arg | Pro | Tyr | Asp | Gly | Gly | Phe | Ala | |
| | | | 195 | | | | | 200 | | | | | 205 | | | |
| tgc | cat | ttc | cac | ccc | aac | gct | ccc | atc | tac | aac | gac | cgc | gag | cgt | ctc | 672 |
| Cys | His | Phe | His | Pro | Asn | Ala | Pro | Ile | Tyr | Asn | Asp | Arg | Glu | Arg | Leu | |
| | | 210 | | | | | 215 | | | | | 220 | | | | |
| cag | ata | tac | atc | tcc | gac | gct | ggc | atc | ctc | gcc | gtc | tgc | tac | ggt | ctc | 720 |
| Gln | Ile | Tyr | Ile | Ser | Asp | Ala | Gly | Ile | Leu | Ala | Val | Cys | Tyr | Gly | Leu | |
| 225 | | | | | 230 | | | | | 235 | | | | | 240 | |
| ttc | cgt | tac | gcc | gcc | gcg | cag | gga | gtg | gcc | tcg | atg | gtc | tgc | ttc | tac | 768 |
| Phe | Arg | Tyr | Ala | Ala | Ala | Gln | Gly | Val | Ala | Ser | Met | Val | Cys | Phe | Tyr | |
| | | | | 245 | | | | | 250 | | | | | 255 | | |
| gga | gtc | ccg | ctt | ctg | att | gtc | aat | ggt | ttc | ctc | gtg | ttg | atc | act | tac | 816 |
| Gly | Val | Pro | Leu | Leu | Ile | Val | Asn | Gly | Phe | Leu | Val | Leu | Ile | Thr | Tyr | |
| | | | 260 | | | | | 265 | | | | | 270 | | | |
| ttg | cag | cac | acg | cat | cct | tcc | ctg | cct | cac | tac | gat | tcg | tcc | gag | tgg | 864 |
| Leu | Gln | His | Thr | His | Pro | Ser | Leu | Pro | His | Tyr | Asp | Ser | Ser | Glu | Trp | |
| | | | 275 | | | | | 280 | | | | | 285 | | | |
| gat | tgg | ttg | agg | gga | gct | ttg | gct | acc | gtt | gac | aga | gac | tac | gaa | atc | 912 |
| Asp | Trp | Leu | Arg | Gly | Ala | Leu | Ala | Thr | Val | Asp | Arg | Asp | Tyr | Glu | Ile | |
| | 290 | | | | | 295 | | | | | 300 | | | | | |
| ttg | aac | aag | gtc | ttc | cac | aat | att | acc | gac | acg | cac | gtg | gcg | cat | cat | 960 |
| Leu | Asn | Lys | Val | Phe | His | Asn | Ile | Thr | Asp | Thr | His | Val | Ala | His | His | |
| 305 | | | | | 310 | | | | | 315 | | | | | 320 | |
| ctg | ttc | tcc | acg | atg | ccg | cat | tat | cac | gcg | atg | gaa | gct | acc | aag | gcg | 1008 |
| Leu | Phe | Ser | Thr | Met | Pro | His | Tyr | His | Ala | Met | Glu | Ala | Thr | Lys | Ala | |
| | | | | 325 | | | | | 330 | | | | | 335 | | |
| ata | aag | ccg | ata | ctg | gga | gag | tat | tat | cag | ttc | gat | ggg | acg | ccg | gtg | 1056 |
| Ile | Lys | Pro | Ile | Leu | Gly | Glu | Tyr | Tyr | Gln | Phe | Asp | Gly | Thr | Pro | Val | |
| | | | 340 | | | | | 345 | | | | | 350 | | | |
| gtt | aag | gcg | atg | tgg | agg | gag | gcg | aag | gag | tgt | atc | tat | gtg | gaa | ccg | 1104 |
| Val | Lys | Ala | Met | Trp | Arg | Glu | Ala | Lys | Glu | Cys | Ile | Tyr | Val | Glu | Pro | |
| | | | 355 | | | | | 360 | | | | | 365 | | | |
| gac | agg | caa | ggt | gag | aag | aaa | ggt | gtg | ttc | tgg | tac | aac | aat | aag | tta | 1152 |
| Asp | Arg | Gln | Gly | Glu | Lys | Lys | Gly | Val | Phe | Trp | Tyr | Asn | Asn | Lys | Leu | |
| | 370 | | | | | 375 | | | | | 380 | | | | | |
| tga | | | | | | | | | | | | | | | | 1155 |

<210> SEQ ID NO 18
<211> LENGTH: 384
<212> TYPE: PRT
<213> ORGANISM: Brassica napus

<400> SEQUENCE: 18

Met Gly Ala Gly Gly Arg Met Gln Val Ser Pro Pro Ser Lys Lys Ser

```
            1               5              10              15
Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
                35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
                115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Asp Gly Gly Phe Ala
                195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
                275                 280                 285

Asp Trp Leu Arg Gly Ala Leu Ala Thr Val Asp Arg Asp Tyr Glu Ile
                290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
370                 375                 380

<210> SEQ ID NO 19
<211> LENGTH: 21
<212> TYPE: DNA
<213> ORGANISM: Artificial Sequence
<220> FEATURE:
<223> OTHER INFORMATION: primer
```

-continued

```
<400> SEQUENCE: 19
ggatatgatg atggtgaaag a                                          21

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
tctttcacca tcatcatatc c                                          21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gttatgaagc aaagaagaaa c                                          21

<210> SEQ ID NO 22
<211> LENGTH: 26
<212> TYPE: DNA
<213> ORGANISM: Artificial Sequence
<220> FEATURE:
<223> OTHER INFORMATION: primer

<400> SEQUENCE: 22
gtttcttctt tgctttgctt cataac                                     26

<210> SEQ ID NO 23
<211> LENGTH: 32
<212> TYPE: DNA
<213> ORGANISM: Artificial Sequence
<220> FEATURE:
<223> OTHER INFORMATION: primer

<400> SEQUENCE: 23
caucaucauc aucttcttcg tagggttcat cg                              32

<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24
cuacuacuac uatcatagaa gagaaaggtt cag                             33

<210> SEQ ID NO 25
<211> LENGTH: 32
<212> TYPE: DNA
<213> ORGANISM: Artificial Sequence
<220> FEATURE:
<223> OTHER INFORMATION: primer

<400> SEQUENCE: 25
caucaucauc aucatgggtg cacgtggaag aa                              32

<210> SEQ ID NO 26
<211> LENGTH: 33
```

```
<212> TYPE: DNA
<213> ORGANISM: Artificial Sequence
<220> FEATURE:
<223> OTHER INFORMATION: primer

<400> SEQUENCE: 26
cuacuacuac uatcuuucac catcatcata tcc                                   33

<210> SEQ ID NO 27
<211> LENGTH: 30
<212> TYPE: PRT
<213> ORGANISM: Arabidopsis thaliana

<400> SEQUENCE: 27
```

Ile Trp Val Ile Ala His Glu Cys Gly His His Ala Phe Ser Asp Tyr
 1               5                  10                  15

Gln Trp Leu Asp Asp Thr Val Gly Leu Ile Phe His Ser Phe
            20                  25                  30

```
<210> SEQ ID NO 28
<211> LENGTH: 30
<212> TYPE: PRT
<213> ORGANISM: Glycine max

<400> SEQUENCE: 28
```

Val Trp Val Ile Ala His Glu Cys Gly His His Ala Phe Ser Lys Tyr
 1               5                  10                  15

Gln Trp Val Asp Asp Val Val Gly Leu Thr Leu His Ser Thr
            20                  25                  30

```
<210> SEQ ID NO 29
<211> LENGTH: 30
<212> TYPE: PRT
<213> ORGANISM: Zea mays

<400> SEQUENCE: 29
```

Val Trp Val Ile Ala His Glu Cys Gly His His Ala Phe Ser Asp Tyr
 1               5                  10                  15

Ser Leu Leu Asp Asp Val Val Gly Leu Val Leu His Ser Ser
            20                  25                  30

```
<210> SEQ ID NO 30
<211> LENGTH: 29
<212> TYPE: PRT
<213> ORGANISM: Ricinus communis

<400> SEQUENCE: 30
```

Trp Val Met Ala His Asp Cys Gly His His Ala Phe Ser Asp Tyr Gln
 1               5                  10                  15

Leu Leu Asp Asp Val Val Gly Leu Ile Leu His Ser Cys
            20                  25

```
<210> SEQ ID NO 31
<211> LENGTH: 29
<212> TYPE: PRT
<213> ORGANISM: Arabidopsis thaliana

<400> SEQUENCE: 31
```

Leu Leu Val Pro Tyr Phe Ser Trp Lys Tyr Ser His Arg Arg His His
 1               5                  10                  15

Ser Asn Thr Gly Ser Leu Glu Arg Asp Glu Val Phe Val
            20                  25

```
<210> SEQ ID NO 32
<211> LENGTH: 29
<212> TYPE: PRT
<213> ORGANISM: Glycine max

<400> SEQUENCE: 32

Leu Leu Val Pro Tyr Phe Ser Trp Lys Ile Ser His Arg His His
 1               5                  10                  15

Ser Asn Thr Gly Ser Leu Asp Arg Asp Glu Val Phe Val
            20                  25

<210> SEQ ID NO 33
<211> LENGTH: 29
<212> TYPE: PRT
<213> ORGANISM: Zea mays

<400> SEQUENCE: 33

Leu Met Val Pro Tyr Phe Ser Trp Lys Tyr Ser His Arg His His
 1               5                  10                  15

Ser Asn Thr Gly Ser Leu Glu Arg Asp Glu Val Phe Val
            20                  25

<210> SEQ ID NO 34
<211> LENGTH: 29
<212> TYPE: PRT
<213> ORGANISM: Ricinus communis

<400> SEQUENCE: 34

Leu Leu Val Pro Tyr Phe Ser Trp Lys His Ser His Arg His His
 1               5                  10                  15

Ser Asn Thr Gly Ser Leu Glu Arg Asp Glu Val Phe Val
            20                  25

<210> SEQ ID NO 35
<211> LENGTH: 36
<212> TYPE: PRT
<213> ORGANISM: Arabidopsis thaliana

<400> SEQUENCE: 35

Asp Arg Asp Tyr Gly Ile Leu Asn Lys Val Phe His Asn Ile Thr Asp
 1               5                  10                  15

Thr His Val Ala His His Leu Phe Ser Thr Met Pro His Tyr Asn Ala
            20                  25                  30

Met Glu Ala Thr
        35

<210> SEQ ID NO 36
<211> LENGTH: 36
<212> TYPE: PRT
<213> ORGANISM: Glycine max

<400> SEQUENCE: 36

Asp Arg Asp Tyr Gly Ile Leu Asn Lys Val Phe His His Ile Thr Asp
 1               5                  10                  15

Thr His Val Ala His His Leu Phe Ser Thr Met Pro His Tyr His Ala
            20                  25                  30

Met Glu Ala Thr
        35

<210> SEQ ID NO 37
<211> LENGTH: 36
```

```
<212> TYPE: PRT
<213> ORGANISM: Zea mays

<400> SEQUENCE: 37

Asp Arg Asp Tyr Gly Ile Leu Asn Arg Val Phe His Asn Ile Thr Asp
 1               5                  10                  15
Thr His Val Ala His His Leu Phe Ser Thr Met Pro His Tyr His Ala
            20                  25                  30
Met Glu Ala Thr
        35

<210> SEQ ID NO 38
<211> LENGTH: 27
<212> TYPE: PRT
<213> ORGANISM: Ricinus communis

<400> SEQUENCE: 38

Asp Arg Asp Tyr Gly Ile Leu Asn Lys Val Phe His Asn Ile Thr Asp
 1               5                  10                  15
Thr Gln Val Ala His His Leu Phe Thr Met Pro
            20                  25

<210> SEQ ID NO 39
<211> LENGTH: 16
<212> TYPE: PRT
<213> ORGANISM: Arabidopsis thaliana

<400> SEQUENCE: 39

Ile Lys Trp Tyr Gly Lys Tyr Leu Asn Asn Pro Leu Gly Arg Ile Met
 1               5                  10                  15

<210> SEQ ID NO 40
<211> LENGTH: 16
<212> TYPE: PRT
<213> ORGANISM: Glycine max

<400> SEQUENCE: 40

Val Ala Trp Phe Ser Leu Tyr Leu Asn Asn Pro Leu Gly Arg Ala Val
 1               5                  10                  15

<210> SEQ ID NO 41
<211> LENGTH: 16
<212> TYPE: PRT
<213> ORGANISM: Zea mays

<400> SEQUENCE: 41

Pro Trp Tyr Thr Pro Tyr Val Tyr Asn Asn Pro Val Gly Arg Val Val
 1               5                  10                  15

<210> SEQ ID NO 42
<211> LENGTH: 16
<212> TYPE: PRT
<213> ORGANISM: Ricinus communis

<400> SEQUENCE: 42

Ile Arg Trp Tyr Ser Lys Tyr Leu Asn Asn Pro Pro Gly Arg Ile Met
 1               5                  10                  15

<210> SEQ ID NO 43
<211> LENGTH: 22
<212> TYPE: PRT
<213> ORGANISM: Arabidopsis thaliana

<400> SEQUENCE: 43
```

```
Trp Ala Leu Phe Val Leu Gly His Asp Cys Gly His Gly Ser Phe Ser
 1               5                  10                  15

Asn Asp Pro Lys Leu Asn
             20

<210> SEQ ID NO 44
<211> LENGTH: 22
<212> TYPE: PRT
<213> ORGANISM: Brassica napus

<400> SEQUENCE: 44

Trp Ala Leu Phe Val Leu Gly His Asp Cys Gly His Gly Ser Phe Ser
 1               5                  10                  15

Asn Asp Pro Arg Leu Asn
             20

<210> SEQ ID NO 45
<211> LENGTH: 22
<212> TYPE: PRT
<213> ORGANISM: Glycine max

<400> SEQUENCE: 45

Trp Ala Leu Phe Val Leu Gly His Asp Cys Gly His Gly Ser Phe Ser
 1               5                  10                  15

Asn Asn Ser Lys Leu Asn
             20

<210> SEQ ID NO 46
<211> LENGTH: 22
<212> TYPE: PRT
<213> ORGANISM: Arabidopsis thaliana

<400> SEQUENCE: 46

Trp Ala Ile Phe Val Leu Gly His Asp Cys Gly His Gly Ser Phe Ser
 1               5                  10                  15

Asp Ile Pro Leu Leu Asn
             20

<210> SEQ ID NO 47
<211> LENGTH: 10
<212> TYPE: PRT
<213> ORGANISM: Artificial Sequence
<220> FEATURE:
<223> OTHER INFORMATION: exemplary motif

<400> SEQUENCE: 47

Asp Arg Asp Tyr Gly Ile Leu Asn Lys Val
 1               5                  10

<210> SEQ ID NO 48
<211> LENGTH: 22
<212> TYPE: PRT
<213> ORGANISM: Glycine max

<400> SEQUENCE: 48

Trp Ala Leu Phe Val Leu Gly His Asp Cys Gly His Gly Ser Phe Ser
 1               5                  10                  15

Asp Ser Pro Pro Leu Asn
             20

<210> SEQ ID NO 49
<211> LENGTH: 29
```

```
<212> TYPE: PRT
<213> ORGANISM: Arabidopsis thaliana

<400> SEQUENCE: 49

Ile Leu Val Pro Tyr His Gly Trp Arg Ile Ser His Arg Thr His His
  1               5                  10                  15

Gln Asn His Gly His Val Glu Asn Asp Glu Ser Trp His
             20                  25

<210> SEQ ID NO 50
<211> LENGTH: 10
<212> TYPE: PRT
<213> ORGANISM: Artificial Sequence
<220> FEATURE:
<223> OTHER INFORMATION: exemplary motif

<400> SEQUENCE: 50

Asp Arg Asp Tyr Glu Ile Leu Asn Lys Val
  1               5                  10

<210> SEQ ID NO 51
<211> LENGTH: 29
<212> TYPE: PRT
<213> ORGANISM: Glycine max

<400> SEQUENCE: 51

Ile Leu Val Pro Tyr His Gly Trp Arg Ile Ser His Arg Thr His His
  1               5                  10                  15

Gln His His Gly His Ala Glu Asn Asp Glu Ser Trp His
             20                  25

<210> SEQ ID NO 52
<211> LENGTH: 29
<212> TYPE: PRT
<213> ORGANISM: Arabidopsis thaliana

<400> SEQUENCE: 52

Ile Leu Val Pro Tyr His Gly Trp Arg Ile Ser His Arg Thr His His
  1               5                  10                  15

Gln Asn His Gly His Val Glu Asn Asp Glu Ser Trp Val
             20                  25

<210> SEQ ID NO 53
<211> LENGTH: 6
<212> TYPE: PRT
<213> ORGANISM: Artificial Sequence
<220> FEATURE:
<223> OTHER INFORMATION: exemplary motif

<400> SEQUENCE: 53

Lys Tyr His Asn Asn Pro
  1               5

<210> SEQ ID NO 54
<211> LENGTH: 29
<212> TYPE: PRT
<213> ORGANISM: Glycine max

<400> SEQUENCE: 54

Ile Leu Val Pro Tyr His Gly Trp Arg Ile Ser His Arg Thr His His
  1               5                  10                  15

Gln Asn His Gly His Ile Glu Lys Asp Glu Ser Trp Val
             20                  25
```

```
<210> SEQ ID NO 55
<211> LENGTH: 6
<212> TYPE: PRT
<213> ORGANISM: Brassica napus

<400> SEQUENCE: 55

Gly His Asp Cys Ala His
  1               5

<210> SEQ ID NO 56
<211> LENGTH: 6
<212> TYPE: PRT
<213> ORGANISM: Brassica napus

<400> SEQUENCE: 56

Gly His Lys Cys Gly His
  1               5

<210> SEQ ID NO 57
<211> LENGTH: 6
<212> TYPE: PRT
<213> ORGANISM: Brassica napus
<220> FEATURE:
<221> NAME/KEY: VARIANT
<223> OTHER INFORMATION: amino acid residues 94-99 of Canola-Fad3

<400> SEQUENCE: 57

Gly His Asp Cys Gly His
  1               5

<210> SEQ ID NO 58
<211> LENGTH: 5
<212> TYPE: PRT
<213> ORGANISM: Artificial Sequence
<220> FEATURE:
<223> OTHER INFORMATION: exemplary motif

<400> SEQUENCE: 58

His Lys Cys Gly His
  1               5

<210> SEQ ID NO 59
<211> LENGTH: 12
<212> TYPE: DNA
<213> ORGANISM: Phaseolus vulgaris

<400> SEQUENCE: 59
tggtcttttg gt                                                          12

<210> SEQ ID NO 60
<211> LENGTH: 5
<212> TYPE: PRT
<213> ORGANISM: Artificial Sequence
<220> FEATURE:
<223> OTHER INFORMATION: exemplary motif

<400> SEQUENCE: 60

His Glu Cys Gly His
  1               5

<210> SEQ ID NO 61
<211> LENGTH: 5
<212> TYPE: PRT
<213> ORGANISM: Artificial Sequence
<220> FEATURE:
<223> OTHER INFORMATION: exemplary motif
```

```
<400> SEQUENCE: 61

His Arg Arg His His
1               5

<210> SEQ ID NO 62
<211> LENGTH: 5
<212> TYPE: PRT
<213> ORGANISM: Artificial Sequence
<220> FEATURE:
<223> OTHER INFORMATION: exemplary motif

<400> SEQUENCE: 62

His Arg Thr His His
1               5

<210> SEQ ID NO 63
<211> LENGTH: 5
<212> TYPE: PRT
<213> ORGANISM: Artificial Sequence
<220> FEATURE:
<223> OTHER INFORMATION: exemplary motif

<400> SEQUENCE: 63

His Val Ala His His
1               5

<210> SEQ ID NO 64
<211> LENGTH: 6
<212> TYPE: PRT
<213> ORGANISM: Artificial Sequence
<220> FEATURE:
<223> OTHER INFORMATION: exemplary motif

<400> SEQUENCE: 64

Lys Tyr Leu Asn Asn Pro
1               5

<210> SEQ ID NO 65
<211> LENGTH: 29
<212> TYPE: PRT
<213> ORGANISM: Brassica napus

<400> SEQUENCE: 65

Val Trp Val Ile Ala His Glu Cys Gly His His Ala Phe Ser Asp Tyr
1               5                   10                  15

Gln Trp Leu Asp Asp Thr Val Gly Leu Ile Phe His Ser
            20                  25

<210> SEQ ID NO 66
<211> LENGTH: 36
<212> TYPE: PRT
<213> ORGANISM: Brassica napus

<400> SEQUENCE: 66

Asp Arg Asp Tyr Gly Ile Leu Asn Lys Val Phe His Asn Ile Thr Asp
1               5                   10                  15

Thr His Val Ala His His Leu Phe Ser Thr Met Pro His Tyr His Ala
            20                  25                  30

Met Glu Ala Thr
        35

<210> SEQ ID NO 67
<211> LENGTH: 16
```

```
<212> TYPE: PRT
<213> ORGANISM: Brassica napus

<400> SEQUENCE: 67

Ile Lys Trp Tyr Gly Lys Tyr Leu Asn Asn Pro Leu Gly Arg Thr Val
 1               5                  10                  15

<210> SEQ ID NO 68
<211> LENGTH: 6
<212> TYPE: PRT
<213> ORGANISM: Artificial Sequence
<220> FEATURE:
<223> OTHER INFORMATION: exemplary motif

<400> SEQUENCE: 68

Ala His Lys Cys Gly His
 1               5

<210> SEQ ID NO 69
<211> LENGTH: 6
<212> TYPE: PRT
<213> ORGANISM: Artificial Sequence
<220> FEATURE:
<223> OTHER INFORMATION: exemplary motif

<400> SEQUENCE: 69

Ala His Glu Cys Gly His
 1               5

<210> SEQ ID NO 70
<211> LENGTH: 5
<212> TYPE: PRT
<213> ORGANISM: Artificial Sequence
<220> FEATURE:
<223> OTHER INFORMATION: exemplary motif

<400> SEQUENCE: 70

His Asp Cys Gly His
 1               5
```

FATTY ACID DESATURASES AND MUTANT SEQUENCES THEREOF

CROSS-REFERENCE TO RELATED APPLICATION

This application is a continuation of U.S. application Ser. No. 10/757,909, filed Jan. 15, 2004, now abandoned, which is a continuation of U.S. application Ser. No. 08/874,109, filed Jun. 12, 1997, now abandoned, which is a continuation-in-part of PCT Application No. PCT/US96/20090, filed Dec. 13, 1996, which is a continuation-in-part of U.S. application Ser. No. 08/572,027, filed Dec. 14, 1995, now U.S. Pat. No. 7,135,614, all of which are incorporated by reference in their entirety.

TECHNICAL FIELD

This invention relates to fatty acid desaturases and nucleic acids encoding desaturase proteins. More particularly, the invention relates to nucleic acids encoding delta-12 and delta-15 fatty acid desaturase proteins that affect fatty acid composition in plants, polypeptides produced from such nucleic acids and plants expressing such nucleic acids.

BACKGROUND OF THE INVENTION

Many breeding studies have been conducted to improve the fatty acid profile of *Brassica* varieties. Pleines and Freidt, Fat Sci. Technol., 90(5), 167-171 (1988) describe plant lines with reduced $C_{18:3}$ levels (2.5-5.8%) combined with high oleic content (73-79%). Rakow and McGregor, J. Amer. Oil Chem. Soc., 50, 400-403 (Oct. 1973) discuss problems associated with selecting mutants for linoleic and linolenic acids. In Can. J. Plant Sci., 68, 509-511 (Apr. 1988) Stellar summer rape producing seed oil with 3% linolenic acid and 28% linoleic acid is disclosed. Roy and Tarr, Z. Pflanzenzuchtg, 95 (3), 201-209 (1985) teaches transfer of genes through an interspecific cross from *Brassica juncea* into *Brassica napus* resulting in a reconstituted line combining high linoleic with low linolenic acid content. Roy and Tarr, Plant Breeding, 98, 89-96 (1987) discuss prospects for development of *B. napus L.* having improved linoleic and linolenic acid content. European Patent application 323,753 published Jul. 12, 1989 discloses seeds and oils having greater than 79% oleic acid combined with less than 3.5% linolenic acid. Canvin, Can. J. Botany, 43, 63-69 (1965) discusses the effect of temperature on the fatty acid composition of oils from several seed crops including rapeseed.

Mutations typically are induced with extremely high doses of radiation and/or chemical mutagens (Gaul, H. Radiation Botany (1964) 4:155-232). High dose levels which exceed LD50, and typically reach LD90, led to maximum achievable mutation rates. In mutation breeding of *Brassica* varieties high levels of chemical mutagens alone or combined with radiation have induced a limited number of fatty acid mutations (Rakow, G. Z. Pflanzenzuchtg (1973) 69:62-82). The low α-linolenic acid mutation derived from the Rakow mutation breeding program did not have direct commercial application because of low seed yield. The first commercial cultivar using the low α-linolenic acid mutation derived in 1973 was released in 1988 as the variety Stellar (Scarth, R. et al., Can. J. Plant Sci. (1988) 68:509-511). Stellar was 20% lower yielding than commercial cultivars at the time of its release.

Alterations in fatty acid composition of vegetable oils is desirable for meeting specific food and industrial uses. For example, *Brassica* varieties with increased monounsaturate levels (oleic acid) in the seed oil, and products derived from such oil, would improve lipid nutrition. Canola lines which are low in polyunsaturated fatty acids and high in oleic acid tend to have higher oxidative stability, which is a useful trait for the retail food industry.

Delta-12 fatty acid desaturase (also known as oleic desaturase) is involved in the enzymatic conversion of oleic acid to linoleic acid. Delta-15 fatty acid desaturase (also known as linoleic desaturase) is involved in the enzymatic conversion of linoleic acid to α-linolenic acid. A microsomal delta-12 desaturase has been cloned and characterized using T-DNA tagging. Okuley, et al., Plant Cell 6:147-158 (1994). The nucleotide sequences of higher plant genes encoding microsomal delta-12 fatty acid desaturase are described in Lightner et al., WO94/11516. Sequences of higher plant genes encoding microsomal and plastid delta-15 fatty acid desaturases are disclosed in Yadav, N., et al., Plant Physiol., 103:467-476 (1993), WO 93/11245 and Arondel, V. et al., Science, 258:1353-1355 (1992). However, there are no teachings that disclose mutations in delta-12 or delta-15 fatty acid desaturase coding sequences from plants. There is a need in the art for more efficient methods to develop plant lines that contain delta-12 or delta-15 fatty acid desaturase gene sequence mutations effective for altering the fatty acid composition of seeds.

SUMMARY OF THE INVENTION

The invention comprises *Brassicaceae* or *Helianthus* seeds, plants and plant lines having at least one mutation that controls the levels of unsaturated fatty acids in plants. One embodiment of the invention is an isolated nucleic acid fragment comprising a nucleotide sequence encoding a mutation from a mutant delta-12 fatty acid desaturase conferring altered fatty composition in seeds when the fragment is present in a plant. A preferred sequence comprises a mutant sequence as shown in FIG. 2. Another embodiment of the invention is an isolated nucleic acid fragment comprising a nucleotide sequence encoding a mutation from a mutant delta-15 fatty acid desaturase. A plant in this embodiment may be soybean, oilseed *Brassica* species, sunflower, castor bean or corn. The mutant sequence may be derived from, for example, a *Brassica napus, Brassica rapa, Brassica juncea* or *Helianthus* delta-12 or delta-15 desaturase gene.

Another embodiment of the invention involves a method of producing a *Brassicaceae* or *Helianthus* plant line comprising the steps of: (a) inducing mutagenesis in cells of a starting variety of a *Brassicaceae* or *Helianthus* species; (b) obtaining progeny plants from the mutagenized cells; (c) identifying progeny plants that contain a mutation in a delta-12 or delta-15 fatty acid desaturase gene; and (d) producing a plant line by selfing or crossing. The resulting plant line may be subjected to mutagenesis in order to obtain a line having both a delta-12 desaturase mutation and a delta-15 desaturase mutation.

Yet another embodiment of the invention involves a method of producing plant lines containing altered fatty acid composition comprising: (a) crossing a first plant with a second plant having a mutant delta-12 or delta-15 fatty acid desaturase; (b) obtaining seeds from the cross of step (a); (c) growing fertile plants from such seeds; (d) obtaining progeny seed from the plants of step (c); and (e) identifying those seeds among the progeny that have altered fatty acid composition. Suitable plants are soybean, rapeseed, sunflower, safflower, castor bean and corn. Preferred plants are rapeseed and sunflower.

The invention is also embodied in vegetable oil obtained from plants disclosed herein, which vegetable oil has an altered fatty acid composition.

BRIEF DESCRIPTION OF THE SEQUENCE LISTING

SEQ ID NO:1 shows a hypothetical DNA sequence of a Brassica Fad2 gene. SEQ ID NO:2 is the deduced amino acid sequence of SEQ ID NO:1.

SEQ ID NO:3 shows a hypothetical DNA sequence of a Brassica Fad2 gene having a mutation at nucleotide 316. SEQ ID NO:4 is the deduced amino acid sequence of SEQ ID NO:3.

SEQ ID NO:5 shows a hypothetical DNA sequence of a Brassica Fad2 gene. SEQ ID NO:6 is the deduced amino acid sequence of SEQ ID NO:5.

SEQ ID NO:7 shows a hypothetical DNA sequence of a Brassica Fad2 gene having a mutation at nucleotide 515. SEQ ID NO:8 is the deduced amino acid sequence of SEQ ID NO:7.

SEQ ID NO:9 shows the DNA sequence for the coding region of a wild type Brassica Fad2-D gene. SEQ ID NO:10 is the deduced amino acid sequence for SEQ ID NO:9.

SEQ ID NO:11 shows the DNA sequence for the coding region of the IMC 129 mutant Brassica Fad2-D gene. SEQ ID NO:12 is the deduced amino acid sequence for SEQ ID NO:11.

SEQ ID NO:13 shows the DNA sequence for the coding region of a wild type Brassica Fad2-F gene. SEQ ID NO:14 is the deduced amino acid sequence for SEQ ID NO:13.

SEQ ID NO:15 shows the DNA sequence for the coding region of the Q508 mutant Brassica Fad2-F gene. SEQ ID NO:16 is the deduced amino acid sequence for SEQ ID NO:15.

SEQ ID NO:17 shows the DNA sequence for the coding region of the Q4275 mutant Brassica Fad2-F gene. SEQ ID NO:18 is the deduced amino acid sequence for SEQ ID NO:17.

BRIEF DESCRIPTION OF THE FIGURES

FIG. 2 shows the nucleotide sequences for a Brassica Fad2-D wild type gene (Fad2-D wt; SEQ ID NO:9), IMC129 mutant gene (Fad2-D GA316 IMC129; SEQ ID NO:11), Fad2-F wild type gene (Fad2-F wt; SEQ ID NO:13) Q508 mutant gene (Fad2-F TA515 Q508; SEQ ID NO:15) and Q4275 mutant gene (Fad2-F GA908 Q4275; SEQ ID NO:17).

FIG. 3 shows the deduced amino acid sequences ( SEQ ID NOS:10, 12, 14, 16, and 18) for the polynucleotides of FIG. 2.

DESCRIPTION OF THE PREFERRED EMBODIMENTS

Figure 1:
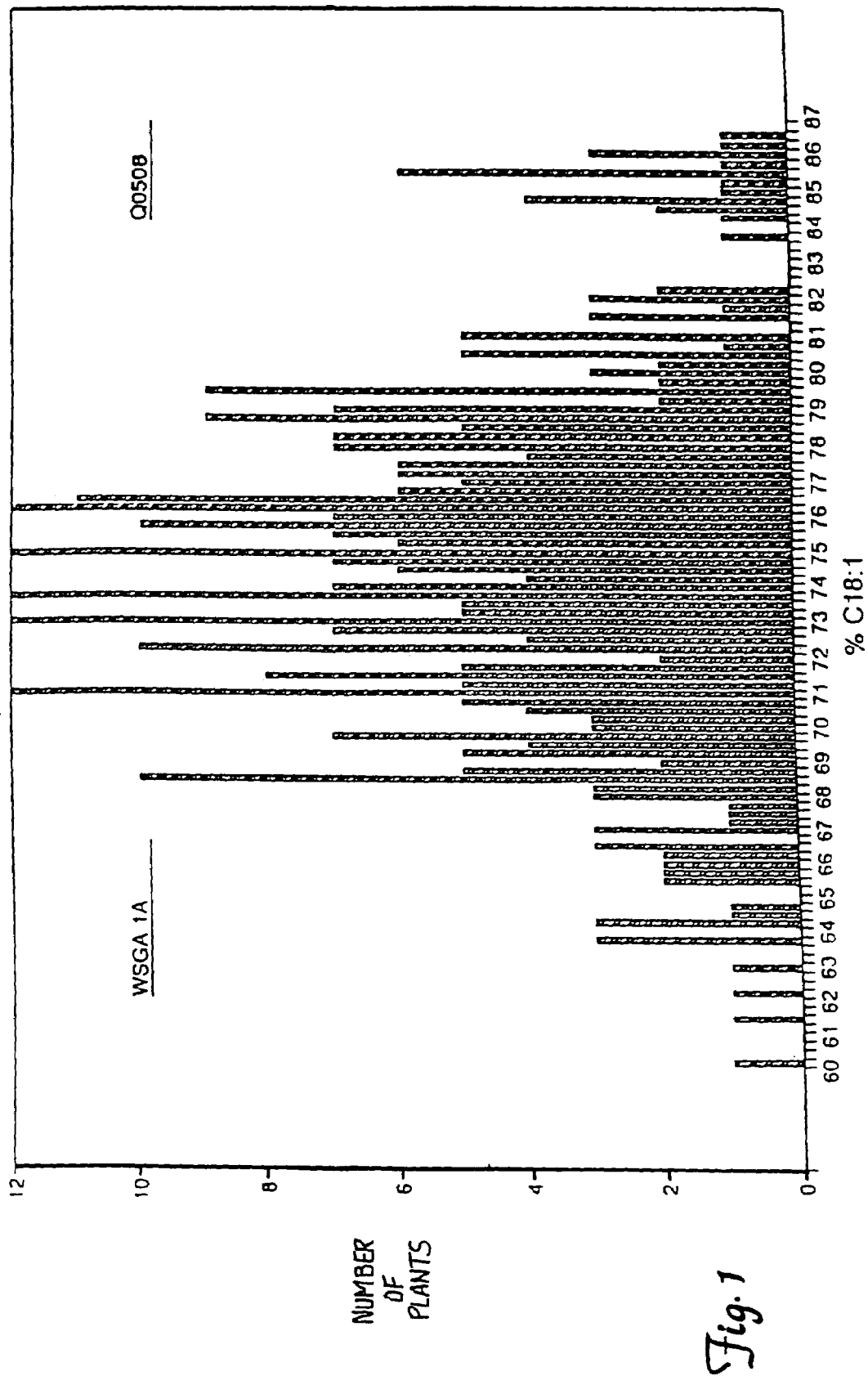
FIG. 1 is a histogram showing the frequency distribution of seed oil oleic acid ($C_{18:1}$) content in a segregating population of a Q508 X Westar cross. The bar labeled WSGA 1A represents the $C_{18:1}$ content of the Westar parent. The bar labeled Q508 represents the $C_{18:1}$ content of the Q508 parent.

All percent fatty acids herein are percent by weight of the oil of which the fatty acid is a component.

As used herein, a "line" is a group of plants that display little or no genetic variation between individuals for at least one trait. Such lines may be created by several generations of self-pollination and selection, or vegetative propagation from a single parent using tissue or cell culture techniques. As used herein, the term "variety" refers to a line which is used for commercial production.

The term "mutagenesis" refers to the use of a mutagenic agent to induce random genetic mutations within a population of individuals. The treated population, or a subsequent generation of that population, is then screened for usable trait(s) that result from the mutations. A "population" is any group of individuals that share a common gene pool. As used herein "$M_0$", is untreated seed. As used herein, "$M_1$" is the seed (and resulting plants) exposed to a mutagenic agent, while "$M_2$" is the progeny (seeds and plants) of self-pollinated $M_1$ plants, "$M_3$" is the progeny of self-pollinated $M_2$ plants, and "$M_4$" is the progeny of self-pollinated $M_3$ plants. "$M_5$" is the progeny of self-pollinated $M_4$ plants. "$M_6$", "$M_7$", etc. are each the progeny of self-pollinated plants of the previous generation. The term "selfed" as used herein means self-pollinated.

"Stability" or "stable" as used herein means that with respect to a given fatty acid component, the component is maintained from generation to generation for at least two generations and preferably at least three generations at substantially the same level, e.g., preferably ±5%. The method of invention is capable of creating lines with improved fatty acid compositions stable up to ±5% from generation to generation. The above stability may be affected by temperature, location, stress and time of planting. Thus, comparison of fatty acid profiles should be made from seeds produced under similar growing conditions. Stability may be measured based on knowledge of prior generation.

Intensive breeding has produced Brassica plants whose seed oil contains less than 2% erucic acid. The same varieties have also been bred so that the defatted meal contains less than 30 μmol glucosinolates/gram. "Canola" as used herein refers to plant variety seed or oil which contains less than 2% erucic acid ($C_{22:1}$), and meal with less than 30 μmol glucosinolates/gram.

Applicants have discovered plants with mutations in a delta-12 fatty acid desaturase gene. Such plants have useful alterations in the fatty acid compositions of the seed oil. Such mutations confer, for example, an elevated oleic acid content, a decreased, stabilized linoleic acid content, or both elevated oleic acid and decreased, stabilized linoleic acid content.

Applicants have further discovered plants with mutations in a delta-15 fatty acid desaturase gene. Such plants have useful alterations in the fatty acid composition of the seed oil, e.g., a decreased, stabilized level of α-linolenic acid.

Applicants have further discovered isolated nucleic acid fragments (polynucleotides) comprising sequences that carry mutations within the coding sequence of delta-12 or delta-15 fatty acid desaturases. The mutations confer desirable alterations ion fatty acid levels in the seed oil of plants carrying such mutations. Delta-12 fatty acid desaturase is also known as omega-6 fatty acid desaturase and is sometimes referred to herein as Fad2 or 12-DES. Delta-15 fatty acid desaturase is also known as omega-3 fatty acid desaturase and is sometimes referred to herein as Fad3 or 15-DES.

A nucleic acid fragment of the invention may be in the form of RNA or in the form of DNA, including cDNA, synthetic DNA or genomic DNA. The DNA may be double-stranded or single-stranded, and if single-stranded, can be either the coding strand or non-coding strand. An RNA analog may be, for example, mRNA or a combination of ribo-and deoxyribonucleotides. Illustrative examples of a nucleic acid fragment of the invention are the mutant sequences shown in FIG. 3.

A nucleic acid fragment of the invention contains a mutation in a microsomal delta-12 fatty acid desaturase coding sequence or a mutation in a microsomal delta-15 fatty acid desaturase coding sequence. Such a mutation renders the resulting desaturase gene product non-functional in plants, relative to the function of the gene product encoded by the wild-type sequence. The non-functionality of the delta-12 desaturase gene product can be inferred from the decreased level of reaction product (linoleic acid) and increased level of substrate (oleic acid) in plant tissues expressing the mutant sequence, compared to the corresponding levels in plant tissues expressing the wild-type sequence. The non-functionality of the delta-15 desaturase gene product can be inferred from the decreased level of reaction product (α-linolenic acid) and the increased level of substrate (linoleic acid) in plant tissues expressing the mutant sequence, compared to the corresponding levels in plant tissues expressing the wild-type sequence.

A nucleic acid fragment of the invention may comprise a portion of the coding sequence, e.g., at least about 10 nucleotides, provided that the fragment contains at least one mutation in the coding sequence. The length of a desired fragment depends upon the purpose for which the fragment will be used, e.g., PCR primer, site-directed mutagenesis and the like. In one embodiment, a nucleic acid fragment of the invention comprises the full length coding sequence of a mutant delta-12 or mutant delta-15 fatty acid desaturase, e.g., the mutant sequences of FIG. 3. In other embodiments, a nucleic acid fragment is about 20 to about 50 nucleotides (or base pairs, bp), or about 50 to about 500 nucleotides, or about 500 to about 1200 nucleotides in length.

A mutation in a nucleic acid fragment of the invention may be in any portion of the coding sequence that renders the resulting gene product non-functional. Suitable types of mutations include, without limitation, insertions of nucleotides, deletions of nucleotides, or transitions and transversions in the wild-type coding sequence. Such mutations result in insertions of one or more amino acids, deletions of one or more amino acids, and non-conservative amino acid substitutions in the corresponding gene product. In some embodiments, the sequence of a nucleic acid fragment may comprise more than one mutation or more than one type of mutation.

Insertion or deletion of amino acids in a coding sequence may, for example, disrupt the conformation of essential alpha-helical or beta-pleated sheet regions of the resulting gene product. Amino acid insertions or deletions may also disrupt binding or catalytic sites important for gene product activity. It is known in the art that the insertion or deletion of a larger number of contiguous amino acids is more likely to render the gene product non-functional, compared to a smaller number of inserted or deleted amino acids.

Non-conservative amino acid substitutions may replace an amino acid of one class with an amino acid of a different class. Non-conservative substitutions may make a substantial change in the charge or hydrophobicity of the gene product. Non-conservative amino acid substitutions may also make a substantial change in the bulk of the residue side chain, e.g., substituting an alanyl residue for a isoleucyl residue.

Examples of non-conservative substitutions include the substitution of a basic amino acid for a non-polar amino acid, or a polar amino acid for an acidic amino acid. Because there are only 20 amino acids encoded in a gene, substitutions that result in a non-functional gene product may be determined by routine experimentation, incorporating amino acids of a different class in the region of the gene product targeted for mutation.

Preferred mutations are in a region of the nucleic acid encoding an amino acid sequence motif that is conserved among delta-12 fatty acid desaturases or delta-15 fatty acid desaturases, such as a His-Xaa-Xaa-Xaa-His motif (Tables 1-3). An example of a suitable region has a conserved HECGH motif (SEQ ID NO:60) that is found, for example, in nucleotides corresponding to amino acids 105 to 109 of the *Arabidopsis* and *Brassica* delta-12 desaturase sequences, in nucleotides corresponding to amino acids 101 to 105 of the soybean delta-12 desaturase sequence and in nucleotides corresponding to amino acids 111 to 115 of the maize delta-12 desaturase sequence. See e.g., WO 94/115116; Okuley et al., Plant Cell 6:147-158 (1994). The one letter amino acid designations used herein are described in Alberts, B. et al., Molecular Biology of the Cell, 3rd edition, Garland Publishing, Previously presented York, 1994. Amino acids flanking this motif are also highly conserved among delta-12 and delta-15 desaturases and are also suitable candidates for mutations in fragments of the invention.

An illustrative embodiment of a mutation in a nucleic acid fragment of the invention is a Glu to Lys substitution in the HECGH (SEQ ID NO:.60) motif of a *Brassica* microsomal delta-12 desaturase sequence, either the D form or the F form. This mutation results in the sequence HECGH (SEQ ID NO:60) being changed to HKCGH (SEQ ID NO:58) as seen by comparing amino acids 105-109 of SEQ ID NO:10 (wild-type D form) to amino acids 105-109 of SEQ ID NO:12 (mutant D form). A similar mutation in other Fad-2 sequences is contemplated to result in a non-functional gene product. (Compare SEQ ID NO:2 to SEQ ID NO:4).

A similar motif may be found at amino acids 101 to 105 of the *Arabidopsis* microsomal delta-15 fatty acid desaturase, as well as in the corresponding rape and soybean desaturases (Table 5). See, e.g., WO 93/11245; Arondel, V. et al., Science, 258:1153-1155 (1992); Yadav, N. et al., Plant Physiol., 103: 467-476 (1993). Plastid delta-15 fatty acids have a similar motif (Table 5).

Among the types of mutations in an HECGH (SEQ ID NO:60)motif that render the resulting gene product non-functional are non-conservative substitutions. An illustrative example of a non-conservative substitution is substitution of a glycine residue for either the first or second histidine. Such a substitution replaces a charged residue (histidine) with a non-polar residue (glycine). Another type of mutation that renders the resulting gene product non-functional is an insertion mutation, e.g., insertion of a glycine between the cysteine and glutamic acid residues in the HECGH (SEQ ID NO:60) motif.

Other regions having suitable conserved amino acid motifs include the HRRHH motif (SEQ ID NO:61) shown in Table 2, the HRTHH motif (SEQ ID NO:62) shown in Table 6 and the HVAHH motif (SEQ ID NO:63)shown in Table 3. See, e.g., WO 94/11516; Hitz, W. et al., Plant Physiol., 105:635-641 (1994); Okuley, J., et al., supra; and Yadav, N. et al., supra. An illustrative example of a mutation in the region shown in Table 3 is a mutation at nucleotides corresponding to the codon for glycine (amino acid 303 of *B. napus*). A non-conservative Gly to Glu substitution results in the amino acid sequence DRDYGILNKV (SEQ ID NO:47, amino acids 299-308 of SEQ ID NO:14) being changed to sequence DRDYEILNKV (SEQ ID NO:50), amino acids 299-308 of SEQ ID NO:18) (compare wild-type F form SEQ ID NO:14 to mutant Q4275 SEQ ID NO:18, FIG. 3).

Another region suitable for a mutation in a delta-12 desaturase sequence contains the motif KYLNNP (SEQ ID NO:64) at nucleotides corresponding to amino acids 170 to 175 of the *Brassica* desaturase sequence. An illustrative example of a mutation in this region is a Leu to His substitution, resulting in the amino acid sequence (Table 4) KYHNN (SEQ ID NO:53), compare wild-type Fad2-F amino acid 170-175 of SEQ ID NO:14 to mutant Fad2-F amino acids 170-175 of SEQ ID NO:16). A similar mutation in other Fad-2 amino acid sequences is contemplated to result in a non-functional gene product. (Compare SEQ ID NO:6 to SEQ ID NO:8).

TABLE 1

Alignment of Amino Acid Sequences from Microsomal Delta-12 Fatty Acid Desaturases

| Species | Position | Amino Acid Sequence | |
|---|---|---|---|
| Arabidopsis thaliana | 100-129 | IWVIAHECGH HAFSDYQWLD DTVGLIFHSF | (SEQ ID NO:27) |
| Glycine max | 96-125 | VWVIAHECGH HAFSKYQWVD DVVGLTLHST | (SEQ ID NO:28) |
| Zea mays | 106-135 | VWVIAHECGH HAFSDYSLLD DVVGLVLHSS | (SEQ ID NO:29) |
| Ricinus communis[a] | 1-29 | WVMAHDCGH HAFSDYQLLD DVVGLILHSC | (SEQ ID NO:30) |
| Brassica napus D | 100-128[b] | VWVIAHECGH HAFSDYQWLD DTVGLIFHS | (SEQ ID NO:65) |
| Brassica napus F | 100-128[c] | VWVIAHECGH HAFSDYQWLD DTVGLIFHS | (SEQ ID NO:65) |

[a]from plasmid pRF2-1C,
[b]positions 100-128 of SEQ ID NO:10;
[c]positions 100-128 of SEQ ID NO:14

TABLE 2

Alignment of Amino Acid Sequences from Microsomal Delta-12 Fatty Acid Desaturases

| Species | Position | Amino Acid Secnience | |
|---|---|---|---|
| Arabidopsis thaliana | 130-158 | LLVPYFSWKY SHRRHHSNTG SLERDEVFV | (SEQ ID NO:31) |
| Glycine max | 126-154 | LLVPYFSWKI SHRRHHSNTG SLDRDEVFV | (SEQ ID NO:32) |
| Zea mays | 136-164 | LMVPYFSWKY SHRRHHSNTG SLERDEVFV | (SEQ ID NO:33) |
| Ricinus communis[a] | 30-58 | LLVPYFSWKH SHRRHHSNTG SLERDEVFV | (SEQ ID NO:34) |
| Brassica napus D | 130-158[b] | LLVPYFSWKY SHRRHHSNTG SLERDEVFV | (SEQ ID NO:31) |
| Brassica napus F | 130-158[c] | LLVPYFSWKY SHRRHHSNTG SLERDEVFV | (SEQ ID NO:31) |

[a]from plasmid pRF2-1C;
[b]positions 130-158 of SEQ ID NO:10;
[c]positions 130-158 of SEQ ID NO:14

TABLE 3

Alignment of Amino Acid Sequences from Microsomal Delta-12 Fatty Acid Desaturases

| Species | Position | Amino Acid Sequence | |
|---|---|---|---|
| Arabidopsis thaliana | 298-333 | DRDYGILNKV FHNITDTHVA HHLFSTMPHY NAMEAT | (SEQ ID NO:35) |
| Glycine max | 294-329 | DRDYGILNKV FHHITDTHVA HHLFSTMPHY HAMEAT | (SEQ ID NO:36) |
| Zea mays | 305-340 | DRDYGILNRV FHNITDTHVA HHLFSTMPHY HAMEAT | (SEQ ID NO:37) |
| Ricinus communis[a] | 198-224 | DRDYGILNKV FHNITDTQVA HHLF TMP | (SEQ ID NO:38) |
| Brassica napus D | 299-334[a] | DRDYGILNKV FHNITDTHVA HHLFSTMPHY HAMEAT | (SEQ ID NO:66) |
| Brassica napus F | 299-334[c] | DRDYGILNKV FHNITDTHVA HHLFSTMPHY HAMEAT | (SEQ ID NO:66) |

[a]from plasmid pRF2-1C;
[b]positions 299-334 of SEQ ID NO:10;
[c]positions 229-334 of SEQ ID NO:14

TABLE 4

Alignment of Conserved Amino Acids from Microsomal Delta-12 Fatty Acid Desaturases

| Species | Position | Amino Acid Sequence | |
|---|---|---|---|
| Arabidopsis thaliana | 165-180 | IKWYGKYLNN PLGRIM | (SEQ ID NO:39) |
| Glycine max | 161-176 | VAWFSLYLNN PLGRAV | (SEQ ID NO:40) |
| Zea mays | 172-187 | PWYTPYVYNN PVGRVV | (SEQ ID NO:41) |
| Ricinus communis[a] | 65-80 | IRWYSKYLNN PPGRIM | (SEQ ID NO:42) |
| Brassica napus D | 165-180[b] | IKWYGKYLNN PLGRTV | (SEQ ID NO:67) |
| Brassica napus F | 165-180[c] | IKWYGKYLNN PLGRTV | (SEQ ID NO:67) |

[a] from plasmid pRF2-1C;
[b] positions 165-180 of SEQ ID NO:10;
[c] positions 165-180 of SEQ ID NO:14

TABLE 5

Alignment of Conserved Amino Acids from Plastid and Microsomal Delta-15 Fatty Acid Desaturases

| Species | Position | Amino Acid Sequence | |
|---|---|---|---|
| Arabidopsis thaliana[a] | 156-177 | WALFVLGHD CGHGSFSNDP KLN | (SEQ ID NO:43) |
| Brassica napus[a] | 114-135 | WALFVLGHD CGHGSFSNDP RLN | (SEQ ID NO:44) |
| Glycine max[a] | 164-185 | WALFVLGHD CGHGSFSNNS KLN | (SEQ ID NO:45) |
| Arabidopsis thaliana | 94-115 | WAIFVLGHD CGHGSFSDIP LLN | (SEQ ID NO:46) |
| Brassica napus | 87-109 | WALFVLGHD CGHGSFSNDP RLN | (SEQ ID NO:44) |
| Glycine max | 93-114 | WALFVLGHD CGHGSFSDSP PLN | (SEQ ID NO:48) |

[a] Plastid sequences

TABLE 6

Alignment of Conserved Amino Acids from Plastid and Microsomal Delta-15 Fatty Acid Desaturases

| Species | Position | Amino Acid Sequence | |
|---|---|---|---|
| A. thaliana[a] | 188-216 | ILVPYHGWRI SHRTHHQNHG HVENDESWH | (SEQ ID NO:49) |
| B. napus[a] | 146-174 | ILVPYHGWRI SHRTHHQNHG HVENDESWH | (SEQ ID NO:49) |
| Glycine max[a] | 196-224 | ILVPYHGWRI SHRTHHQHHG HAENDESWH | (SEQ ID NO:51) |
| A. thaliana | 126-154 | ILVPYHGWRI SHRTHHQNHG HVENDESWV | (SEQ ID NO:52) |
| Brassica napus | 117-145 | ILVPYEGWRI SHRTHHQNHG HVENDESWV | (SEQ ID NO:52) |
| Glycine max | 125-153 | ILVPYHGWRI SHRTHHQNHG HIEKDESWV | (SEQ ID NO:54) |

[a] Plastid sequences

The conservation of amino acid motifs and their relative positions indicates that regions of a delta-12 or delta-15 fatty acid desaturase that can be mutated in one species to generate a non-functional desaturase can be mutated in the corresponding region from other species to generate a non-functional delta-12 desaturase or delta-15 desaturase gene product in that species.

Mutations in any of the regions of Tables 1-6 are specifically included within the scope of the invention and are substantially identical to those mutations exemplified herein, provided that such mutation (or mutations) renders the resulting desaturase gene product non-functional, as discussed hereinabove.

A nucleic acid fragment containing a mutant sequence can be generated by techniques known to the skilled artisan. Such techniques include, without limitation, site-directed mutagenesis of wild-type sequences and direct synthesis using automated DNA synthesizers.

A nucleic acid fragment containing a mutant sequence can also be generated by mutagenesis of plant seeds or regenerable plant tissue by, e.g., ethyl methane sulfonate, X-rays or other mutagens. With mutagenesis, mutant plants having the desired fatty acid phenotype in seeds are identified by known techniques and a nucleic acid fragment containing the desired mutation is isolated from genomic DNA or RNA of the mutant line. The site of the specific mutation is then determined by sequencing the coding region of the delta-12 desaturase or delta-15 desaturase gene. Alternatively, labeled nucleic acid probes that are specific for desired mutational events can be used to rapidly screen a mutagenized population.

The disclosed method may be applied to all oilseed *Brassica* species, and to both Spring and Winter maturing types within each species. Physical mutagens, including but not limited to X-rays, UV rays, and other physical treatments which cause chromosome damage, and other chemical mutagens, including but not limited to ethidium bromide, nitrosoguanidine, diepoxybutane etc. may also be used to induce mutations. The mutagenesis treatment may also be applied to other stages of plant development, including but not limited to cell cultures, embryos, microspores and shoot apices.

"Stable mutations" as used herein are defined as $M_5$ or more advanced lines which maintain a selected altered fatty acid profile for a minimum of three generations, including a minimum of two generations under field conditions, and exceeding established statistical thresholds for a minimum of two generations, as determined by gas chromatographic analysis of a minimum of 10 randomly selected seeds bulked together. Alternatively, stability may be measured in the same way by comparing to subsequent generations. In subsequent generations, stability is defined as having similar fatty acid profiles in the seed as that of the prior or subsequent generation when grown under substantially similar conditions.

Mutation breeding has traditionally produced plants carrying, in addition to the trait of interest, multiple, deleterious traits, e.g., reduced plant vigor and reduced fertility. Such traits may indirectly affect fatty acid composition, producing an unstable mutation; and/or reduce yield, thereby reducing the commercial utility of the invention. To eliminate the occurrence of deleterious mutations and reduce the load of mutations carried by the plant, a low mutagen dose is used in the seed treatments to create an LD30 population. This allows for the rapid selection of single gene mutations for fatty acid traits in agronomic backgrounds which produce acceptable yields.

The seeds of several different fatty acid lines have been deposited with the American Type Culture Collection, 10801 University Blvd., Manassas, Va. 20110-2209, and have the following accession numbers.

| Line | Accession No. | Deposit Date |
| --- | --- | --- |
| A129.5 | 40811 | May 25, 1990 |
| A133.1 | 40812 | May 25, 1990 |
| M3032.1 | 75021 | Jun. 7, 1991 |
| M3062.8 | 75025 | Jun. 7, 1991 |
| M3028.10 | 75026 | Jun. 7, 1991 |
| IMC130 | 75446 | Apr. 16, 1993 |
| Q4275 | 97569 | May 10, 1996 |

Seed designated Q4275 was placed deposited with the American Type Culture Collection (Manassas, Va.) under the Budapest Treaty. All restrictions upon public access to the deposit will be irrevocably removed upon grant of the patent. The deposit will be replaced if the depository cannot dispense viable samples.

In some plant species or varieties more than one form of endogenous microsomal delta-12 desaturase may be found. In amphidiploids, each form may be derived from one of the parent genomes making up the species under consideration. Plants with mutations in both forms have a fatty acid profile that differs from plants with a mutation in only one form. An example of such a plant is *Brassica napus* line Q508, a doubly-mutagenized line containing a mutant D-form of delta-12 desaturase (SEQ ID NO:11) and a mutant F-form of delta-12 desaturase (SEQ ID NO:15). Another example is line Q4275, which contains a mutant D-form of delta-12 desaturase (SEQ ID NO:11) and a mutant F-form of delta-12 desaturase (SEQ ID NO:17). See FIGS. 2-3.

Preferred host or recipient organisms for introduction of a nucleic acid fragment of the invention are the oil-producing species, such as soybean (*Glycine max*), rapeseed (e.g., *Brassica napus, B. rapa* and *B. juncea*), sunflower (*Helianthus annus*), castor bean (*Ricinus communis*), corn (*Zea mays*), and safflower (*Carthamus tinctorius*).

A nucleic acid fragment of the invention may further comprise additional nucleic acids. For example, a nucleic acid encoding a secretory or leader amino acid sequence can be linked to a mutant desaturase nucleic acid fragment such that the secretory or leader sequence is fused in-frame to the amino terminal end of a mutant delta-12 or delta-15 desaturase polypeptide. Other nucleic acid fragments are known in the art that encode amino acid sequences useful for fusing in-frame to the mutant desaturase polypeptides disclosed herein. See, e.g., U.S. Pat. No. 5,629,193 incorporated herein by reference. A nucleic acid fragment may also have one or more regulatory elements operably linked thereto.

The present invention also comprises nucleic acid fragments that selectively hybridize to mutant desaturase sequences. Such a nucleic acid fragment typically is at least 15 nucleotides in length. Hybridization typically involves Southern analysis (Southern blotting), a method by which the presence of DNA sequences in a target nucleic acid mixture are identified by hybridization to a labeled oligonucleotide or DNA fragment probe. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37-9.52 of Sambrook et al., (1989) *Molecular Cloning*, second edition, Cold Spring Harbor Laboratory, Plainview; N.Y.

A nucleic acid fragment can hybridize under moderate stringency conditions or, preferably, under high stringency conditions to a mutant desaturase sequence. High stringency conditions are used to identify nucleic acids that have a high degree of homology to the probe. High stringency conditions can include the use of low ionic strength and high temperature for washing, for example, 0.015 M NaCl/0.0015 M sodium citrate (0.1×SSC); 0.1% sodium lauryl sulfate (SDS) at 50-65° C. Alternatively, a denaturing agent such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

Moderate stringency conditions refers to hybridization conditions used to identify nucleic acids that have a lower degree of identity to the probe than do nucleic acids identified under high stringency conditions. Moderate stringency conditions can include the use of higher ionic strength and/or lower temperatures for washing of the hybridization membrane, compared to the ionic strength and temperatures used for high stringency hybridization. For example, a wash solution comprising 0.060 M NaCl/0.0060 M sodium citrate (4×SSC) and 0.1% sodium lauryl sulfate (SDS) can be used at 50° C., with a last wash in 1×SSC, at 65° C. Alternatively, a hybridization wash in 1×SSC at 37° C. can be used.

Hybridization can also be done by Northern analysis (Northern blotting), a method used to identify RNAs that hybridize to a known probe such as an oligonucleotide, DNA fragment, cDNA or fragment thereof, or RNA fragment. The probe is labeled with a radioisotope such as $^{32}P$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39-7.52 of Sambrook et al., supra.

A polypeptide of the invention comprises an isolated polypeptide having a mutant amino acid sequence, as well as derivatives and analogs thereof. See, e.g., the mutant amino acid sequences of FIG. 3. By "isolated" is meant a polypeptide that is expressed and produced in an environment other than the environment in which the polypeptide is naturally expressed and produced. For example, a plant polypeptide is isolated when expressed and produced in bacteria or fungi. A polypeptide of the invention also comprises variants of the mutant desaturase polypeptides disclosed herein, as discussed above.

In one embodiment of the claimed invention, a plant contains both a delta-12 desaturase mutation and a delta-15 desaturase mutation. Such plants can have a fatty acid composition comprising very high oleic acid and very low alpha-linolenic acid levels. Mutations in delta-12 desaturase and delta-15 desaturase may be combined in a plant by making a genetic cross between delta-12 desaturase and delta-15 desaturase single mutant lines. A plant having a mutation in delta-12 fatty acid desaturase is crossed or mated with a second plant having a mutation in delta-15 fatty acid desaturase. Seeds produced from the cross are planted and the resulting plants are selfed in order to obtain progeny seeds. These progeny seeds are then screened in order to identify those seeds carrying both mutant genes.

Alternatively, a line possessing either a delta-12 desaturase or a delta-15 desaturase mutation can be subjected to mutagenesis to generate a plant or plant line having mutations in both delta-12 desaturase and delta-15 desaturase. For example, the IMC 129 line has a mutation in the coding region ($Glu_{106}$ to $Lys_{106}$) of the D form of the microsomal delta-12 desaturase structural gene. Cells (e.g., seeds) of this line can be mutagenized to induce a mutation in a delta-15 desaturase gene, resulting in a plant or plant line carrying a mutation in a delta-12 fatty acid desaturase gene and a mutation in a delta-15 fatty acid desaturase gene.

Progeny includes descendants of a particular plant or plant line, e.g., seeds developed on an instant plant are descendants. Progeny of an instant plant include seeds formed on $F_1$, $F_2$, $F_3$, and subsequent generation plants, or seeds formed on $BC_1$, $BC_2$, $BC_3$ and subsequent generation plants.

Plants according to the invention preferably contain an altered fatty acid composition. For example, oil obtained from seeds of such plants may have from about 69 to about 90% oleic acid, based on the total fatty acid composition of the seed. Such oil preferably has from about 74 to about 90% oleic acid, more preferably from about 80 to about 90% oleic acid. In some embodiments, oil obtained from seeds produced by plants of the invention may have from about 2.0% to about 5.0% saturated fatty acids, based on total fatty acid composition of the seeds. In some embodiments, oil obtained from seeds of the invention may have from about 1.0% to about 14.0% linoleic acid, or from about 0.5% to about 10.0% α-linolenic acid.

Oil composition typically is analyzed by crushing and extracting fatty acids from bulk seed samples (e.g., 10 seeds). Fatty acid triglycerides in the seed are hydrolyzed and converted to fatty acid methyl esters. Those seeds having an altered fatty acid composition may be identified by techniques known to the skilled artisan, e.g., gas-liquid chromatography (GLC) analysis of a bulked seed sample or of a single half-seed. Half-seed analysis is well known in the art to be useful because the viability of the embryo is maintained and thus those seeds having a desired fatty acid profile may be planted to from the next generation. However, half-seed analysis is also known to be an inaccurate representation of genotype of the seed being analyzed. Bulk seed analysis typically yields a more accurate representation of the fatty acid profile of a given genotype. Fatty-acid composition can also be determined on larger samples, e.g., oil obtained by pilot plant or commercial scale refining, bleaching and deodorizing of endogenous oil in the seeds.

The nucleic acid fragments of the invention can be used as markers in plant genetic mapping and plant breeding programs. Such markers may include restriction fragment length polymorphism (RFLP), random amplification polymorphism detection (RAPD), polymerase chain reaction (PCR) or self-sustained sequence replication (3SR) markers, for example. Marker-assisted breeding techniques may be used to identify and follow a desired fatty acid composition during the breeding process. Marker-assisted breeding techniques may be used in addition to, or as an alternative to, other sorts of identification techniques. An example of marker-assisted breeding is the use of PCR primers that specifically amplify a sequence containing a desired mutation in delta-12 desaturase or delta-15 desaturase.

Methods according to the invention are useful in that the resulting plants and plant lines have desirable seed fatty acid compositions as well as superior agronomic properties compared to known lines having altered seed fatty acid composition. Superior agronomic characteristics include, for example, increased seed germination percentage, increased seedling vigor, increased resistance to seedling fungal diseases (damping off, root rot and the like), increased yield, and improved standability.

While the invention is susceptible to various modifications and alternative forms, certain specific embodiments thereof are described in the general methods and examples set forth below. For example the invention may be applied to all *Brassica* species, including *B. rapa, B. juncea*, and *B. hirta*, to produce substantially similar results. It should be understood, however, that these examples are not intended to limit the invention to the particular forms disclosed but, instead the invention is to cover all modifications, equivalents and alternatives falling within the scope of the invention. This includes the use of somaclonal variation; physical or chemical mutagenesis of plant parts; anther, microspore or ovary culture followed by chromosome doubling; or self- or cross-pollination to transmit the fatty acid trait, alone or in combination with other traits, to develop new *Brassica* lines.

EXAMPLE 1

Mutagenesis

Seeds of Westar, a Canadian (*Brassica napus*) spring canola variety, were subjected to chemical mutagenesis. Westar is a registered Canadian spring variety with canola quality. The fatty acid composition of field-grown Westar, 3.9% $C_{16:0}$, 1.9% $C_{18:0}$, 67.5% $C_{18:1}$, 17.6% $C_{18:2}$, 7.4% $C_{18:3}$<2% $C20:1+C_{22:1}$, has remained stable under commercial production, with <±10% deviation, since 1982.

Prior to mutagenesis, 30,000 seeds of *B. napus* cv. Westar seeds were preimbibed in 300-seed lots for two hours on wet filter paper to soften the seed coat. The preimbibed seeds were placed in 80 mM ethylmethanesulfonate (EMS) for four hours. Following mutagenesis, the seeds were rinsed three times in distilled water. The seeds were sown in 48-well flats containing Pro-Mix. Sixty-eight percent of the mutagenized seed germinated. The plants were maintained at 25° C./15° C., 14/10 hr day/night conditions in the greenhouse. At flowering, each plant was individually self-pollinated.

$M_2$ seed from individual plants were individually catalogued and stored, approximately 15,000 $M_2$ lines was planted in a summer nursery in Carman, Manitoba. The seed from each selfed plant were planted in 3-meter rows with 6-inch row spacing. Westar was planted as the check variety. Selected lines in the field were selfed by bagging the main raceme of each plant. At maturity, the selfed plants were individually harvested and seeds were catalogued and stored to ensure that the source of the seed was known.

Self-pollinated $M_3$ seed and Westar controls were analyzed in 10-seed bulk samples for fatty acid composition via gas chromatography. Statistical thresholds for each fatty acid component were established using a Z-distribution with a stringency level of 1 in 10,000. Mean and standard deviation values were determined from the non-mutagenized Westar control population in the field. The upper and lower statistical thresholds for each fatty acid were determined from the mean value of the population ± the standard deviation, multiplied by the Z-distribution. Based on a population size of 10,000, the confidence interval is 99.99%.

The selected $M_3$ seeds were planted in the greenhouse along with Westar controls. The seed was sown in 4-inch pots containing Pro-Mix soil and the plants were maintained at 25° C./15° C., 14/10 hr day/night cycle in the greenhouse. At flowering, the terminal raceme was self-pollinated by bagging. At maturity, selfed $M_4$ seed was individually harvested from each plant, labelled, and stored to ensure that the source of the seed was known.

The $M_4$ seed was analyzed in 10-seed bulk samples. Statistical thresholds for each fatty acid component were established from 259 control samples using a Z-distribution of 1 in 800. Selected $M_4$ lines were planted in a field trial in Carman, Manitoba in 3-meter rows with 6-inch spacing. Ten $M_4$ plants in each row were bagged for self-pollination. At maturity, the selfed plants were individually harvested and the open pollinated plants in the row were bulk harvested. The $M_5$ seed from single plant selections was analyzed in 10-seed bulk samples and the bulk row harvest in 50-seed bulk samples.

Selected $M_5$ lines were planted in the greenhouse along with Westar controls. The seed was grown as previously described. At flowering the terminal raceme was self-pollinated by bagging. At maturity, selfed $M_6$ seed was individually harvested from each plant and analyzed in 10-seed bulk samples for fatty acid composition.

Selected $M_6$ lines were entered into field trials in Eastern Idaho. The four trial locations were selected for the wide variability in growing conditions. The locations included Burley, Tetonia, Lamont and Shelley (Table 7). The lines were planted in four 3-meter rows with an 8-inch spacing, each plot was replicated four times. The planting design was determined using a Randomized Complete Block Designed. The commercial cultivar Westar was used as a check cultivar. At maturity the plots were harvested to determine yield. Yield of the entries in the trial was determined by taking the statistical average of the four replications. The Least Significant Difference Test was used to rank the entries in the randomized complete block design.

TABLE 7

Trial Locations for Selected Fatty Acid Mutants

| LOCATION | SITE CHARACTERIZATIONS |
|---|---|
| BURLEY | Irrigated. Long season. High temperatures during flowering. |
| TETONIA | Dryland. Short season. Cool temperatures. |
| LAMONT | Dryland. Short season. Cool temperatures. |
| SHELLEY | Irrigated. Medium season. High temperatures during flowering. |

To determine the fatty acid profile of entries, plants in each plot were bagged for self-pollination. The $M_7$ seed from single plants was analyzed for fatty acids in ten-seed bulk samples.

To determine the genetic relationships of the selected fatty acid mutants crosses were made. Flowers of $M_6$ or later generation mutations were used in crossing. $F_1$ seed was harvested and analyzed for fatty acid composition to determine the mode of gene action. The $F_1$ progeny were planted in the greenhouse. The resulting plants were self-pollinated, the $F_2$ seed harvested and analyzed for fatty acid composition for allelism studies. The $F_2$ seed and parent line seed was planted in the greenhouse, individual plants were self-pollinated. The $F_3$ seed of individual plants was tested for fatty acid composition using 10-seed bulk samples as described previously.

In the analysis of some genetic relationships dihaploid populations were made from the microspores of the $F_1$ hybrids. Self-pollinated seed from dihaploid plants were analyzed for fatty acid analysis using methods described previously.

For chemical analysis, 10-seed bulk samples were hand ground with a glass rod in a 15-mL polypropylene tube and extracted in 1.2 mL 0.25 N KOH in 1:1 ether/methanol. The sample was vortexed for 30 sec. and heated for 60 sec. in a 60° C. water bath. Four mL of saturated NaCl and 2.4 mL of iso-octane were added, and the mixture was vortexed again. After phase separation, 600 μL of the upper organic phase were pipetted into individual vials and stored under nitrogen at −5° C. One μL samples were injected into a Supelco SP-2330 fused silica capillary column (0.25 mm ID, 30 M length, 0.20 μm df).

The gas chromatograph was set at 180° C. for 5.5 minutes, then programmed for a 2° C./minute increase to 212° C., and held at this temperature for 1.5 minutes. Total run time was 23 minutes. Chromatography settings were: Column head pressure—15 psi, Column flow (He)—0.7 mL/min., Auxiliary and Column flow—33 mL/min., Hydrogen flow—33 mL/min., Air flow—400 mL/min., Injector temperature—250° C., Detector temperature—300° C., Split vent—1/15.

Table 8 describes the upper and lower statistical thresholds for each fatty acid of interest.

TABLE 8

Statistical Thresholds for Specific Fatty Acids Derived from Control Westar Plantings

| | Percent Fatty Acids | | | | | |
|---|---|---|---|---|---|---|
| Genotype | $C_{16:0}$ | $C_{18:0}$ | $C_{18:1}$ | $C_{18:2}$ | $C_{18:3}$ | Sats* |
| $M_3$ Generation (1 in 10,000 rejection rate) | | | | | | |
| Lower | 3.3 | 1.4 | — | 13.2 | 5.3 | 6.0 |
| Upper | 4.3 | 2.5 | 71.0 | 21.6 | 9.9 | 8.3 |

TABLE 8-continued

Statistical Thresholds for Specific Fatty Acids
Derived from Control Westar Plantings

| | Percent Fatty Acids | | | | | |
|---|---|---|---|---|---|---|
| Genotype | $C_{16:0}$ | $C_{18:0}$ | $C_{18:1}$ | $C_{18:2}$ | $C_{18:3}$ | Sats* |
| $M_4$ Generation (1 in 800 rejection rate) | | | | | | |
| Lower | 3.6 | 0.8 | — | 12.2 | 3.2 | 5.3 |
| Upper | 6.3 | 3.1 | 76.0 | 32.4 | 9.9 | 11.2 |
| $M_5$ Generation (1 in 755 rejection rate) | | | | | | |
| Lower | 2.7 | 0.9 | — | 9.6 | 2.6 | 4.5 |
| Upper | 5.7 | 2.7 | 80.3 | 26.7 | 9.6 | 10.0 |

*Sats = Total Saturate Content

EXAMPLE 2

High Oleic Acid Canola Lines

In the studies of Example 1, at the $M_3$ generation, 31 lines exceeded the upper statistical threshold for oleic acid (≧71.0%). Line W7608.3 had 71.2% oleic acid. At the $M_4$ generation, its selfed progeny (W7608.3.5, since designated A129.5) continued to exceed the upper statistical threshold for $C_{18:1}$ with 78.8% oleic acid. $M_5$ seed of five self-pollinated plants of line A129.5 (ATCC 40811) averaged 75.0% oleic acid. A single plant selection, A129.5.3 had 75.6% oleic acid. The fatty acid composition of this high oleic acid mutant, which was stable under both field and greenhouse conditions to the $M_7$ generation, is summarized in Table 9. This line also stably maintained its mutant fatty acid composition to the $M_7$ generation in field trials in multiple locations. Over all locations the self-pollinated plants (A129) averaged 78.3% oleic acid. The fatty acid composition of the A129 for each Idaho trial location are summarized in Table 10. In multiple location replicated yield trials, A129 was not significantly different in yield from the parent cultivar Westar.

The canola oil of A129, after commercial processing, was found to have superior oxidative stability compared to Westar when measured by the Accelerated Oxygen Method (AOM), American Oil Chemists' Society Official Method Cd 12-57 for fat stability; Active Oxygen Method (revised 1989). The AOM of Westar was 18 AOM hours and for A129 was 30 AOM hours.

TABLE 9

Fatty Acid Composition of a High Oleic Acid
Canola Line Produced by Seed Mutagenesis

| | Percent Fatty Acids | | | | | |
|---|---|---|---|---|---|---|
| Genotype | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 7.0 |
| W7608.3 ($M_3$) | 3.9 | 2.4 | 71.2 | 12.7 | 6.1 | 7.6 |
| W7608.3.5 ($M_4$) | 3.9 | 2.0 | 78.8 | 7.7 | 3.9 | 7.3 |
| A129.5.3 ($M_5$) | 3.8 | 2.3 | 75.6 | 9.5 | 4.9 | 7.6 |

Sats = Total Saturate Content

TABLE 10

Fatty Acid Composition of a Mutant High Oleic Acid
Line at Different Field Locations in Idaho

| | Percent Fatty Acids | | | | | |
|---|---|---|---|---|---|---|
| Location | $C_{16:0}$ | $C_{18:0}$ | $C_{18:1}$ | $C_{18:2}$ | $C_{18:3}$ | Sats |
| Burley | 3.3 | 2.1 | 77.5 | 8.1 | 6.0 | 6.5 |
| Tetonia | 3.5 | 3.4 | 77.8 | 6.5 | 4.7 | 8.5 |
| Lamont | 3.4 | 1.9 | 77.8 | 7.4 | 6.5 | 6.3 |
| Shelley | 3.3 | 2.6 | 80.0 | 5.7 | 4.5 | 7.7 |

Sats = Total Saturate Content

The genetic relationship of the high oleic acid mutation A129 to other oleic desaturases was demonstrated in crosses made to commercial canola cultivars and a low linolenic acid mutation. A129 was crossed to the commercial cultivar Global ($C_{16:0}$-4.5%, $C_{18:0}$-1.5%, $C_{18:1}$-62.9%, $C_{18:2}$ -20.0%, $C_{18:3}$-7.3%). Approximately 200 $F_2$ individuals were analyzed for fatty acid composition. The results are summarized in Table 11. The segregation fit 1:2:1 ratio suggesting a single co-dominant gene controlled the inheritance of the high oleic acid phenotype.

TABLE 11

Genetic Studies of A129 × Global

| | $C_{18:0}$ | Frequency | |
|---|---|---|---|
| Genotype | Content (%) | Observed | Expected |
| od − od − | 77.3 | 43 | 47 |
| od − od + | 71.7 | 106 | 94 |
| od + od + | 66.1 | 49 | 47 |

A cross between A129 and IMC 01, a low linolenic acid variety ($C_{16:0}$-4.1%, $C_{18:0}$-1.9%, $C_{18:1}$-66.4%, $C_{18:2}$-18.1%, $C_{18:3}$-5.7%), was made to determine the inheritance of the oleic acid desaturase and linoleic acid desaturase. In the $F_1$ hybrids both the oleic acid and linoleic acid desaturase genes approached the mid-parent values indicating a co-dominant gene actions. Fatty acid analysis of the $F_2$ individuals confirmed a 1:2:1:2:4:2:1:2:1 segregation of two independent, co-dominant genes (Table 12). A line was selected from the cross of A129 and IMC01 and designated as IMC130 (ATCC deposit no. 75446) as described in U.S. patent application Ser. No. 08/425,108, incorporated herein by reference.

TABLE 12

Genetic Studies of A129 × IMC 01

| | | Frequency | |
|---|---|---|---|
| Genotype | Ratio | Observed | Expected |
| od − od − ld − ld − | 1 | 11 | 12 |
| od − od − ld − ld + | 2 | 30 | 24 |
| od − od − ld + ld + | 1 | 10 | 12 |
| od − od + ld − ld − | 2 | 25 | 24 |
| od − od + ld − ld + | 4 | 54 | 47 |
| od − od + ld + ld + | 2 | 18 | 24 |
| od + od + ld − ld − | 1 | 7 | 12 |
| od + od + ld − ld + | 2 | 25 | 24 |
| od + od + ld + ld + | 1 | 8 | 12 |

An additional high oleic acid line, designated A128.3, was also produced by the disclosed method. A 50-seed bulk analysis of this line showed the following fatty acid composition:

$C_{16:0}$-3.5%, $C_{18:0}$-1.8%, $C_{18:1}$-77.3%, $C_{18:2}$-9.0%, $C_{18:3}$-5.6%, FDA Sats-5.3%, Total Sats-6.4%. This line also stably maintained its mutant fatty acid composition to the $M_7$ generation. In multiple locations replicated yield trials, A128 was not significantly different in yield from the parent cultivar Westar.

A129 was crossed to A128.3 for allelism studies. Fatty acid composition of the $F_2$ seed showed the two lines to be allelic. The mutational events in A129 and A128.3 although different in origin were in the same gene.

An additional high oleic acid line, designated M3028.-10 (ATCC 75026), was also produced by the disclosed method in Example 1. A 10-seed bulk analysis of this line showed the following fatty acid composition: $C_{16:0}$-3.5%, $C_{18:0}$-1.8%, $C_{18:1}$-77.3%, $C_{18:2}$-9.0%, $C_{18:3}$-5.6%, FDA Saturates-5.3%, Total Saturates-6.4%. In a single location replicated yield trial M3028.10 was not significantly different in yield from the parent cultivar Westar.

EXAMPLE 3

Low Linoleic Acid Canola

In the studies of Example 1, at the $M_3$ generation, 80 lines exceeded the lower statistical threshold for linoleic acid ($\leq$13.2%). Line W12638.8 had 9.4% linoleic acid. At the $M_4$ and $M_5$ generations, its selfed progenies [W12638.8, since designated A133.1 (ATCC 40812)] continued to exceed the statistical threshold for low $C_{18:2}$ with linoleic acid levels of 10.2% and 8.4%, respectively. The fatty acid composition of this low linoleic acid mutant, which was stable to the $M_7$ generation under both field and greenhouse conditions, is summarized in Table 13. In multiple location replicated yield trials, A133 was not significantly different in yield from the parent cultivar Westar. An additional low linoleic acid line, designated M3062.8 (ATCC 75025), was also produced by the disclosed method. A 10-seed bulk analysis of this line showed the following fatty acid composition: $C_{16:0}$-3.8%, $C_{18:0}$-2.3%, $C_{18:1}$-77.1%, $C_{18:2}$-8.9%, $C_{18:3}$-4.3%, FDA Sats-6.1%. This line has also stably maintained its mutant fatty acid composition in the field and greenhouse.

TABLE 13

Fatty Acid Composition of a Low Linoleic Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats[b] |
| Westar | 3.9 | 1.9 | 67.5 | 17.6 | 7.4 | 7.0 |
| W12638.8 ($M_3$) | 3.9 | 2.3 | 75.0 | 9.4 | 6.1 | 7.5 |
| W12638.8.1 ($M_4$) | 4.1 | 1.7 | 74.6 | 10.2 | 5.9 | 7.1 |
| A133.1.8 ($M_5$) | 3.8 | 2.0 | 77.7 | 8.4 | 5.0 | 7.0 |

[a] Letter and numbers up to second decimal point indicate the plant line. Number after second decimal point indicates an individual plant.
[b] Sats = Total Saturate Content

EXAMPLE 4

Low Linolenic and Linoleic Acid Canola

In the studies of Example 1, at the $M_3$ generation, 57 lines exceeded the lower statistical threshold for linolenic acid ($\leq$5.3%). Line W14749.8 had 5.3% linolenic acid and 15.0% linoleic acid. At the $M_4$ and $M_5$ generations, its selfed progenies [W14749.8, since designated M3032 (ATCC 75021)] continued to exceed the statistical threshold for low $C_{18:3}$ with linolenic acid levels of 2.7% and 2.3%, respectively, and for a low sum of linolenic and linoleic acids with totals of 11.8% and 12.5% respectively. The fatty acid composition of this low linolenic acid plus linoleic acid mutant, which was stable to the $M_5$ generation under both field and greenhouse conditions, is summarized in Table 14. In a single location replicated yield trial M3032 was not significantly different in yield from the parent cultivar (Westar).

TABLE 14

Fatty Acid Composition of a Low Linolenic Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 7.0 |
| W14749.8 ($M_3$) | 4.0 | 2.5 | 69.4 | 15.0 | 5.3 | 6.5 |
| M3032.8 ($M_4$) | 3.9 | 2.4 | 77.9 | 9.1 | 2.7 | 6.4 |
| M3032.1 ($M_5$) | 3.5 | 2.8 | 80.0 | 10.2 | 2.3 | 6.5 |

Sats = Total Saturate Content

EXAMPLE 5

Canola Lines Q508 and Q4275

Seeds of the *B. napus* line IMC-129 were mutagenized with methyl N-nitrosoguanidine (MNNG). The MNNG treatment consisted of three parts: pre-soak, mutagen application, and wash. A 0.05 M Sorenson's phosphate buffer was used to maintain pre-soak and mutagen treatment pH at 6.1. Two hundred seeds were treated at one time on filter paper (Whatman #3 M) in a petri dish (100 mm×15 mm). The seeds were pre-soaked in 15 mls of 0.05 M Sorenson's buffer, pH 6.1, under continued agitation for two hours. At the end of the pre-soak period, the buffer was removed from the plate.

A 10 mM concentration of MNNG in 0.05 M Sorenson's buffer, pH 6.1, was prepared prior to use. Fifteen ml of 10 m MNNG was added to the seeds in each plate. The seeds were incubated at 22° C.±3° C. in the dark under constant agitation for four (4) hours. At the end of the incubation period, the mutagen solution was removed.

The seeds were washed with three changes of distilled water at 10 minute intervals. The fourth wash was for thirty minutes. This treatment regime produced an LD60 population.

Treated seeds were planted in standard greenhouse potting soil and placed into an environmentally controlled greenhouse. The plants were grown under sixteen hours of light. At flowering, the racemes were bagged to produce selfed seed. At maturity, the M2 seed was harvested. Each M2 line was given an identifying number. The entire MNNG-treated seed population was designated as the Q series.

Harvested M2 seeds was planted in the greenhouse. The growth conditions were maintained as previously described. The racemes were bagged at flowering for selfing. At maturity, the selfed M3 seed was harvested and analyzed for fatty acid composition. For each M3 seed line, approximately 10-15 seeds were analyzed in bulk as described in Example 1.

High oleic-low linoleic M3 lines were selected from the M3 population using a cutoff of >82% oleic acid and <5.0% linoleic. From the first 1600 M3 lines screened for fatty acid composition, Q508 was identified. The Q508 M3 generation was advanced to the M4 generation in the greenhouse. Table 15 shows the fatty acid composition of Q508 and IMC 129. The M4 selfed seed maintained the selected high oleic-low linoleic acid phenotype (Table 16).

TABLE 15

Fatty Acid Composition of A129 and High Oleic Acid M3 Mutant 0508

| Line # | 16:0 | 18:0 | 18:1 | 18:2 | 18:3 |
|---|---|---|---|---|---|
| A129* | 4.0 | 2.4 | 77.7 | 7.8 | 4.2 |
| Q508 | 3.9 | 2.1 | 84.9 | 2.4 | 2.9 |

*Fatty acid composition of A129 is the average of 50 self-pollinated plants grown with the M3 population $M_4$ generation Q508 plants had poor agronomic qualities in the field compared to Westar. Typical plants were slow growing relative to Westar, lacked early vegetative vigor, were short in stature, tended to be chlorotic and had short pods. The yield of Q508 was very low compared to Westar.

The $M_4$ generation Q508 plants in the greenhouse tended to be reduced in vigor compared to Westar. However, Q508 yields in the greenhouse were greater than Q508 yields in the field.

TABLE 16

Fatty Acid Composition of Seed Oil from Greenhouse-Grown Q508, IMC 129 and Westar.

| Line | 16:0 | 18:0 | 18:1 | 18:2 | 18:3 | FDA Sats |
|---|---|---|---|---|---|---|
| IMC 129[a] | 4.0 | 2.4 | 77.7 | 7.8 | 4.2 | 6.4 |
| Westar[b] | 3.9 | 1.9 | 67.5 | 17.6 | 7.4 | >5.8 |
| Q508[c] | 3.9 | 2.1 | 84.9 | 2.4 | 2.9 | 6.0 |

[a]Average of 50 self-pollinated plants
[b]Data from Example 1
[c]Average of 50 self-pollinated plants Nine other M4 high-oleic low-linoleic lines were also identified: Q3603, Q3733, Q4249, Q6284, Q6601, Q6761, Q7415, Q4275, and Q6676. Some of these lines had good agronomic characteristics and an elevated oleic acid level in seeds of about 80% to about 84%.

Q4275 was crossed to the variety Cyclone. After selfing for seven generations, mature seed was harvested from 93GS34-179, a progeny line of the Q4275 Cyclone cross. Referring to Table 17, fatty acid composition of a bulk seed sample shows that 93GS34 retained the seed fatty acid composition of Q4275. 93GS34-179 also maintained agronomically desirable characteristics.

After more than seven generations of selfing of Q4275, plants of Q4275, IMC 129 and 93GS34 were field grown during the summer season. The selections were tested in 4 replicated plots (5 feet×20 feet) in a randomized block design. Plants were open pollinated. No-selfed seed was produced. Each plot was harvested at maturity, and a sample of the bulk harvested seed from each line was analyzed for fatty acid composition as described above. The fatty acid compositions of the selected lines are shown in Table 17.

TABLE 17

Fatty Acid Composition of Field Grown IMC 129, Q4275 and 93GS34 Seeds

| | Fatty Acid Composition (%) | | | | | |
|---|---|---|---|---|---|---|
| Line | $C_{16:0}$ | $C_{18:0}$ | $C_{18:1}$ | $C_{18:2}$ | $C_{18:3}$ | FDA Sats |
| IMC 129 | 3.3 | 2.4 | 76.7 | 8.7 | 5.2 | 5.7 |
| Q4275 | 3.7 | 3.1 | 82.1 | 4.0 | 3.5 | 6.8 |
| 93GS34-179 | 2.6 | 2.7 | 85.0 | 2.8 | 3.3 | 5.3 |

The results shown in Table 17 show that Q4275 maintained the selected high oleic-low linoleic acid phenotype under field conditions. The agronomic characteristics of Q4275 plants were superior to those of Q508.

$M_4$ generation Q508 plants were crossed to a dihaploid selection of Westar, with Westar serving as the female parent. The resulting F1 seed was termed the 92EF population. About 126 F1 individuals that appeared to have better agronomic characteristics than the Q508 parent were selected for selfing. A portion of the $F_2$ seed from such individuals was replanted in the field. Each F2 plant was selfed and a portion of the resulting F3 seed was analyzed for fatty acid composition. The content of oleic acid in $F_3$ seed ranged from 59 to 79%. No high oleic (>80%) individuals were recovered with good agronomic type.

A portion of the $F_2$ seed of the 92EF population was planted in the greenhouse to analyze the genetics of the Q508 line. $F_3$ seed was analyzed from 380 F2 individuals. The $C_{18:1}$ levels of $F_3$ seed from the greenhouse experiment is depicted in FIG. 1. The data were tested against the hypothesis that Q508 contains two mutant genes that are semi-dominant and additive: the original IMC 129 mutation as well as one additional mutation. The hypothesis also assumes that homozygous Q508 has greater than 85% oleic acid and homozygous Westar has 62-67% oleic acid. The possible genotypes at each gene in a cross of Q508 by Westar may be designated as:

AA=Westar Fad2[a]

BB=Westar Fad2[b]

aa=Q508Fad2[a−]

=Q508Fad2[b−]

Assuming independent segregation, a 1:4:6:4:1 ratio of phenotypes is expected. The phenotypes of heterozygous plants are assumed to be indistinguishable and, thus, the data were tested for fit to a 1:14:1 ratio of homozygous Westar: heterozygous plants: homozygous Q508.

| Phenotypic Ratio | # of Westar Alleles | Genotype |
|---|---|---|
| 1 | 4 | AABB (Westar) |
| 4 | 3 | AABb, AaBB, AABb, AaBB |
| 6 | 2 | AaBb, AAbb, AaBb, AaBb, aaBB, AaBb |
| 4 | 1 | Aabb, aaBb, Aabb, aaBb |
| 1 | 0 | aabb (Q508) |

Using Chi-square analysis, the oleic acid data fit a 1:14:1 ratio. It was concluded that Q508 differs from Westar by two major genes that are semi-dominant and additive and that segregate independently. By comparison, the genotype of IMC 129 is aaBB.

The fatty acid composition of representative F3 individuals having greater than 85% oleic acid in seed oil is shown in Table 18. The levels of saturated fatty acids are seen to be decreased in such plants, compared to Westar.

TABLE 18

92EF F3 Individuals with > 85% $C_{18:1}$ in Seed Oil

| F3 Plant Identifier | Fatty Acid Composition (%) | | | | | |
|---|---|---|---|---|---|---|
| | C16:0 | C18:0 | C18:1 | C18:2 | C18:3 | FDASA |
| +38068 | 3.401 | 1.582 | 85.452 | 2.134 | 3.615 | 4.983 |
| +38156 | 3.388 | 1.379 | 85.434 | 2.143 | 3.701 | 4.767 |
| +38171 | 3.588 | 1.511 | 85.289 | 2.367 | 3.425 | 5.099 |
| +38181 | 3.75 | 1.16 | 85.312 | 2.968 | 3.819 | 4.977 |
| +38182 | 3.529 | 0.985 | 85.905 | 2.614 | 3.926 | 4.56 |
| +38191 | 3.364 | 1.039 | 85.737 | 2.869 | 4.039 | 4.459 |
| +38196 | 3.557 | 1.182 | 85.054 | 2.962 | 4.252 | 4.739 |
| +38202 | 3.554 | 1.105 | 86.091 | 2.651 | 3.721 | 4.713 |
| +38220 | 3.093 | 1.16 | 86.421 | 1.931 | 3.514 | 4.314 |
| +38236 | 3.308 | 1.349 | 85.425 | 2.37 | 3.605 | 4.718 |
| +38408 | 3.617 | 1.607 | 85.34 | 2.33 | 3.562 | 5.224 |
| +38427 | 3.494 | 1.454 | 85.924 | 2.206 | 3.289 | 4.948 |
| +38533 | 3.64 | 1.319 | 85.962 | 2.715 | 3.516 | 4.959 |

EXAMPLE 6

Leaf and Root Fatty Acid Profiles of Canola Lines IMC-129, Q508, and Westar

Plants of Q508, IMC 129 and Westar were grown in the greenhouse. Mature leaves, primary expanding leaves, petioles and roots were harvested at the 6-8 leaf stage, frozen in liquid nitrogen and stored at −70° C. Lipid extracts were analyzed by GLC as described in Example 1. The fatty acid profile data are shown in Table 19.

The data in Table 19 indicate that total leaf lipids in Q508 are higher in $C_{18:1}$ content than the $C_{18:2}$ plus $C_{18:3}$ content. The reverse is true for Westar and IMC 129. The difference in total leaf lipids between Q508 and IMC 129 is consistent with the hypothesis that a second Fad2 gene is mutated in Q508.

The $C_{16:3}$ content in the total lipid fraction was about the same for all three lines, suggesting that the plastid FadC gene product was not affected by the Q508 mutations. To confirm that the FadC gene was not mutated, chloroplast lipids were separated and analyzed. No changes in chloroplast $C_{16:1}$, $C_{16:2}$ or $C_{16:3}$ fatty acids were detected in the three lines. The similarity in plastid leaf lipids among Q508, Westar and IMC 129 is consistent with the hypothesis that the second mutation in Q508 affects a microsomal Fad2 gene and not a plastid FadC gene.

EXAMPLE 7

Sequences of Mutant and Wild-Type Delta-12 Fatty Acid Desaturases from *B. napus*

Primers specific for the FAD2 structural gene were used to clone the entire open reading frame (ORF) of the D and F delta-12 desaturase genes by reverse transcriptase polymerase chain reaction (RT-PCR). RNA from seeds of IMC 129, Q508 and Westar plants was isolated by standard methods and was used as template. The RT-amplified fragments were used for nucleotide sequence determination. The DNA sequence of each gene from each line was determined from both strands by standard dideoxy sequencing methods.

Sequence analysis revealed a G to A transversion at nucleotide 316 (from the translation initiation codon) of the D gene in both IMC 129 and Q508, compared to the sequence of Westar. The transversion changes the codon at this position from GAG to AAG and results in a non-conservative substitution of glutamic acid, an acidic residue, for lysine a basic residue. The presence of the same mutation in both lines was expected since the Q508 line was derived from IMC 129. The same base change was also detected in Q508 and IMC 129 when RNA from leaf tissue was used as template.

The G to A mutation at nucleotide 316 was confirmed by sequencing several independent clones containing fragments amplified directly from genomic DNA of IMC 129 and Westar. These results eliminated the possibility of a rare mutation introduced during reverse transcription and PCR in the RT-PCR protocol. It was concluded that the IMC 129 mutant is due to a single base transversion at nucleotide 316 in the coding region of the D gene of rapeseed microsomal delta 12-desaturase.

A single base transition from T to A at nucleotide 515 of the F gene was detected in Q508 compared to the Westar sequence. The mutation changes the codon at this position from CTC to CAC, resulting in the non-conservative substitution of a polar residue, histidine, for a non-polar residue, leucine, in the resulting gene product. No mutations were found in the F gene sequence of IMC 129 compared to the F gene sequence of Westar.

These data support the conclusion that a mutation in a delta-12 desaturase gene sequence results in alterations in the fatty acid profile of plants containing such a mutated gene. Moreover, the data show that when a plant line or species contains two delta-12 desaturase loci, the fatty acid profile of an individual having two mutated loci differs from the fatty acid profile of an individual having one mutated locus.

The mutation in the D gene of IMC 129 and Q508 mapped to a region having a conserved amino acid motif (His-Xaa-

TABLE 19

| | MATURE LEAF | | | EXPANDING LEAF | | | PETIOLE | | | ROOT | | |
|---|---|---|---|---|---|---|---|---|---|---|---|---|
| | West. | 129 | 3Q508 | West. | 129 | 3Q508 | West. | 129 | 3Q508 | West. | 129 | 3Q508 |
| 16:0 | 12.1 | 11.9 | 10.1 | 16.4 | 16.1 | 11.3 | 21.7 | 23.5 | 11.9 | 21.1 | 21.9 | 12.0 |
| 16:1 | 0.8 | 0.6 | 1.1 | 0.7 | 0.6 | 1.1 | 1.0 | 1.3 | 1.4 | — | — | — |
| 16:2 | 2.3 | 2.2 | 2.0 | 2.8 | 3.1 | 2.8 | 1.8 | 2.2 | 1.8 | — | — | — |
| 16:3 | 14.7 | 15.0 | 14.0 | 6.3 | 5.4 | 6.9 | 5.7 | 4.6 | 5.7 | — | — | — |
| 18:0 | 2.2 | 1.6 | 1.2 | 2.5 | 2.8 | 1.5 | 3.7 | 4.0 | 1.6 | 3.6 | 2.9 | 2.5 |
| 18:1 | 2.8 | 4.9 | 16.7 | 3.8 | 8.3 | 38.0 | 4.9 | 12.9 | 46.9 | 3.5 | 6.1 | 68.8 |
| 18:2 | 12.6 | 11.5 | 6.8 | 13.3 | 13.8 | 4.9 | 20.7 | 18.3 | 5.2 | 28.0 | 30.4 | 4.4 |
| 18:3 | 50.6 | 50.3 | 46.0 | 54.2 | 50.0 | 33.5 | 40.4 | 33.2 | 25.3 | 43.8 | 38.7 | 12.3 |

Xaa-Xaa-His) found in cloned delta-12 and delta-15 membrane bound-desaturases (Table 20).

TABLE 20

Alignment of Amino Acid Sequences
of Cloned Canola Membrane Bound-Desaturases

| Desaturase Gene | Sequence[a] | Position |
|---|---|---|
| Canola-fad2-D (mutant) | AHKCGH (SEQ ID NO:68) | 109-114 SEQ ID NO:12 |
| Canola-Fad2-D | AHECGH (SEQ ID NO:69) | 109-114 SEQ ID NO:10 |
| Canola-Fad2-F | AHECGH (SEQ ID NO:69) | 109-114 SEQ ID NO:14 |
| Canola-FadC | GHDCAH (SEQ ID NO:55) | 170-175 |
| Canola-fad3 (mutant) | GHKCGH (SEQ ID NO:56) | 94-99 |
| Canola-Fad3 | GHDCGH (SEQ ID NO:57) | 94-99 |
| Canola-FadD | GHDCGH (SEQ ID NO:57) | 125-130 |

(FadD = Plastid delta 15, Fad3 = Microsomal delta-15), (FadC = Plastid delta-12, Fad2 = Microsomal delta-12)
[a]One letter amino acid code; conservative substitutions are underlined; non-conservative substitutions are in bold.

EXAMPLE 8

Transcription and Translation of Microsomal Delta-12 Fatty Acid Desaturases

Transcription in vivo was analyzed by RT-PCR analysis of stage II and stage III developing seeds and leaf tissue. The primers used to specifically amplify delta-12 desaturase F gene RNA from the indicated tissues were sense primer 5'-GGATATGATGATGGTGAAAGA-3' (SEQ ID NO:19) and antisense primer 5'-TCTTTCACCATCATCATATCC-3' (SEQ ID NO:20).The primers used to specifically amplify delta-12 desaturase D gene RNA from the indicated tissues were sense primer 5'-GTTATGAAGCAAAGAAGAAAC-3' (SEQ ID NO:21) and antisense primer 5'-GTTTCT-TCTTTGCTTCATAAC-3' (SEQ ID NO:22). The results indicated that mRNA of both the D and F gene was expressed in seed and leaf tissues of IMC 129, Q508 and wild type Westar plants.

In vitro transcription and translation analysis showed that a peptide of about 46 kD was made. This is the expected size of both the D gene product and the F gene product, based on sum of the deduced amino acid sequence of each gene and the cotranslational addition of a microsomal membrane peptide.

These results rule out the possibility that non-sense or frameshift mutations, resulting in a truncated polypeptide gene product, are present in either the mutant D gene or the mutant F gene. The data, in conjunction with the data of Example 7, support the conclusion that the mutations in Q508 and IMC 129 are in delta-12 fatty acid desaturase structural genes encoding desaturase enzymes, rather than in regulatory genes.

EXAMPLE 9

Development of Gene-Specific PCR Markers

Based on the single base change in the mutant D gene of IMC 129 described in above, two 5' PCR primers were designed. The nucleotide sequence of the primers differed only in the base (G for Westar and A for IMC 129) at the 3' end. The primers allow one to distinguish between mutant fad2-D and wild-type Fad2-D alleles in a DNA-based PCR assay. Since there is only a single base difference in the 5' PCR primers, the PCR assay is very sensitive to the PCR conditions such as annealing temperature, cycle number, amount, and purity of DNA templates used. Assay conditions have been established that distinguish between the mutant gene and the wild type gene using genomic DNA from IMC 129 and wild type plants as templates. Conditions may be further optimized by varying PCR parameters, particularly with variable crude DNA samples. A PCR assay distinguishing the single base mutation in IMC 129 from the wild type gene along with fatty acid composition analysis provides a means to simplify segregation and selection analysis of genetic crosses involving plants having a delta-12 fatty acid desaturase mutation.

EXAMPLE 10

Transformation with Mutant and Wild Type Fad3 Genes

B. napus cultivar Westar was transformed with mutant and wild type Fad3 genes to demonstrate that the mutant Fad3 gene for canola cytoplasmic linoleic desaturase delta-15 desaturase is nonfunctional. Transformation and regeneration were performed using disarmed Agrobacterium tumefaciens essentially following the procedure described in WO 94/11516.

Two disarmed Agrobacterium strains were engineered, each containing a Ti plasmid having the appropriate gene linked to a seed-specific promoter and a corresponding termination sequence. The first plasmid, pIMC110, was prepared by inserting into a disarmed Ti vector the full length wild type Fad3 gene in sense orientation (nucleotides 208 to 1336 of SEQ ID 6 in WO 93/11245), flanked by a napin promoter sequence positioned 5' to the Fad3 gene and a napin termination sequence positioned 3' to the Fad3 gene. The rapeseed napin promoter is described in EP 0255378.

The second plasmid, pIMC205, was prepared by inserting a mutated Fad3 gene in sense orientation into a disarmed Ti vector. The mutant sequence contained mutations at nucleotides 411 and 413 of the microsomal Fad3 gene described in WO93/11245, thus changing the sequence for codon 96 from GAC to AAG. The amino acid at codon 96 of the gene product was thereby changed from aspartic acid to lysine. See Table 20. A bean (Phaseolus vulgaris) phaseolin (7S seed storage protein) promoter fragment of 495 base pairs, starting with 5'-TGGTCTTTTGGT-3' (SEQ ID NO:59), was placed 5' to the mutant Fad3 gene and a phaseolin termination sequence was placed 3' to the mutant Fad3 gene. The phaseolin sequence is described in Doyle et al., (1986) J. Biol. Chem. 261:9228-9238) and Slightom et al., (1983) Proc. Natl. Acad. Sci. USA 80:1897-1901.

The appropriate plasmids were engineered and transferred separately to *Agrobacterium* strain LBA4404. Each engineered strain was used to infect 5 mm segments of hypocotyl explants from Westar seeds by cocultivation. Infected hypocotyls were transferred to callus medium and, subsequently, to regeneration medium. Once discernable stems formed from the callus, shoots were excised and transferred to elongation medium. The elongated shoots were cut, dipped in Rootone™, rooted on an agar medium and transplanted to potting soil to obtain fertile T1 plants. T2 seeds were obtained by selfing the resulting T1 plants.

Fatty acid analysis of T2 seeds was carried out as described above. The results are summarized in Table 21. Of the 40 transformants obtained using the pIMC110 plasmid, 17 plants demonstrated wild type fatty acid profiles and 16 demonstrated overexpression. A proportion of the transformants are expected to display an overexpression phenotype when a functioning gene is transformed in sense orientation into plants.

Of the 307 transformed plants having the pIMC205 gene, none exhibited a fatty acid composition indicative of overexpression. This result indicates that the mutant fad3 gene product is non-functional, since some of the transformants would have exhibited an overexpression phenotype if the gene product were functional.

TABLE 21

Overexpression and Co-suppression Events in Westar Populations Transformed with pIMC205 or pIMC110.

| Construct | Number of Transfomants | α-Linolenic Acid Range (%) | Overexpression Events (>10% linolenic) | Co-Suppression Events (<4.0% linolenic) | Wild Type Events |
|---|---|---|---|---|---|
| pIMC110 | 40 | 2.4-20.6 | 16 | 7 | 17 |
| pIMC205 | 307 | 4.6-10.4 | 0 | 0 | 307 |

Fatty acid compositions of representative transformed plants are presented in Table 22. Lines 652-09 and 663-40 are representative of plants containing pIMC110 and exhibiting an overexpression and a co-suppression phenotype, respectively. Line 205-284 is representative of plants containing PIMC205 and having the mutant fad3 gene.

TABLE 22

Fatty Acid Composition of T2 Seed From Westar Transformed With pIMC205 or pIMC110.

| | Fatty Acid Composition (%) | | | | |
|---|---|---|---|---|---|
| Line | C16:0 | C18:0 | C18:1 | C18:2 | C18:3 |
| 652-09 pIMC110 overexpression | 4.7 | 3.3 | 65.6 | 8.1 | 14.8 |
| 663-40 pIMC110 co-suppression | 4.9 | 2.1 | 62.5 | 23.2 | 3.6 |
| 205-284 pIMC205 | 3.7 | 1.8 | 68.8 | 15.9 | 6.7 |

EXAMPLE 11

Sequences of Wild Type and Mutant Fad2-D and Fad2-F

High molecular weight genomic DNA was isolated from leaves of Q4275 plants (Example 5). This DNA was used as template for amplification of Fad2-D and Fad2-F genes by polymerase chain reaction (PCR). PCR amplifications were carried out in a total volume of 100 µl and contained 0.3 µg genomic DNA, 200 µM deoxyribonucleoside triphosphates, 3 mM $MgSO_4$, 1-2 Units DNA polymerase and 1× Buffer (supplied by the DNA polymerase manufacturer). Cycle conditions were: 1 cycle for 1 min at 95° C., followed by 30 cycles of 1 min at 94° C., 2 min at 55° C. and 3 min at 73° C.

The Fad2-D gene was amplified once using Elongase® (Gibco-BRL). PCR primers were:

(SEQ ID NO:23)
5'-CAUCAUCAUCAUCUUCUUCGUAGGGUUCAUCG-3' and (SEQ ID NO:24)
5'-CUACUACUACUAUCAUAGAAGAGAAAGGUUCAG-3' for the 5' and 3' ends of the gene, respectively.

The Fad2-F gene was independently amplified 4 times, twice with Elongase® and twice with Taq polymerase (Boehringer Mannheim). The PCR primers used were:

(SEQ ID NO:25)
5'CAUCAUCAUCAUCAUGGGUGCACGUGGAAGAA3' and (SEQ ID NO:26)
5'CUACUACUACUAUCUUUCACCAUCAUCAUAUCC3' for the 5' and 3' ends of the gene, respectively.

Amplified DNA products were resolved on an agarose gel, purified by JetSorb® and then annealed into pAMP1 (Gibco-BRL) via the $(CAU)_4$ and $(CUA)_4$ sequences at the ends of the primers, and transformed into *E. coli* DH5α.

The Fad2-D and Fad2-F inserts were sequenced on both strands with an ABI PRISM 310 automated sequencer (Perkin-Elmer) following the manufacturer's directions, using synthetic primers, AmpliTaq® DNA polymerase and dye terminator.

The Fad2-D gene was found to have an intron upstream of the ATG start codon. As expected, the coding sequence of the gene contained a G to A mutation at nucleotide 316, derived from IMC 129 (FIG. 2).

Figure 2A:
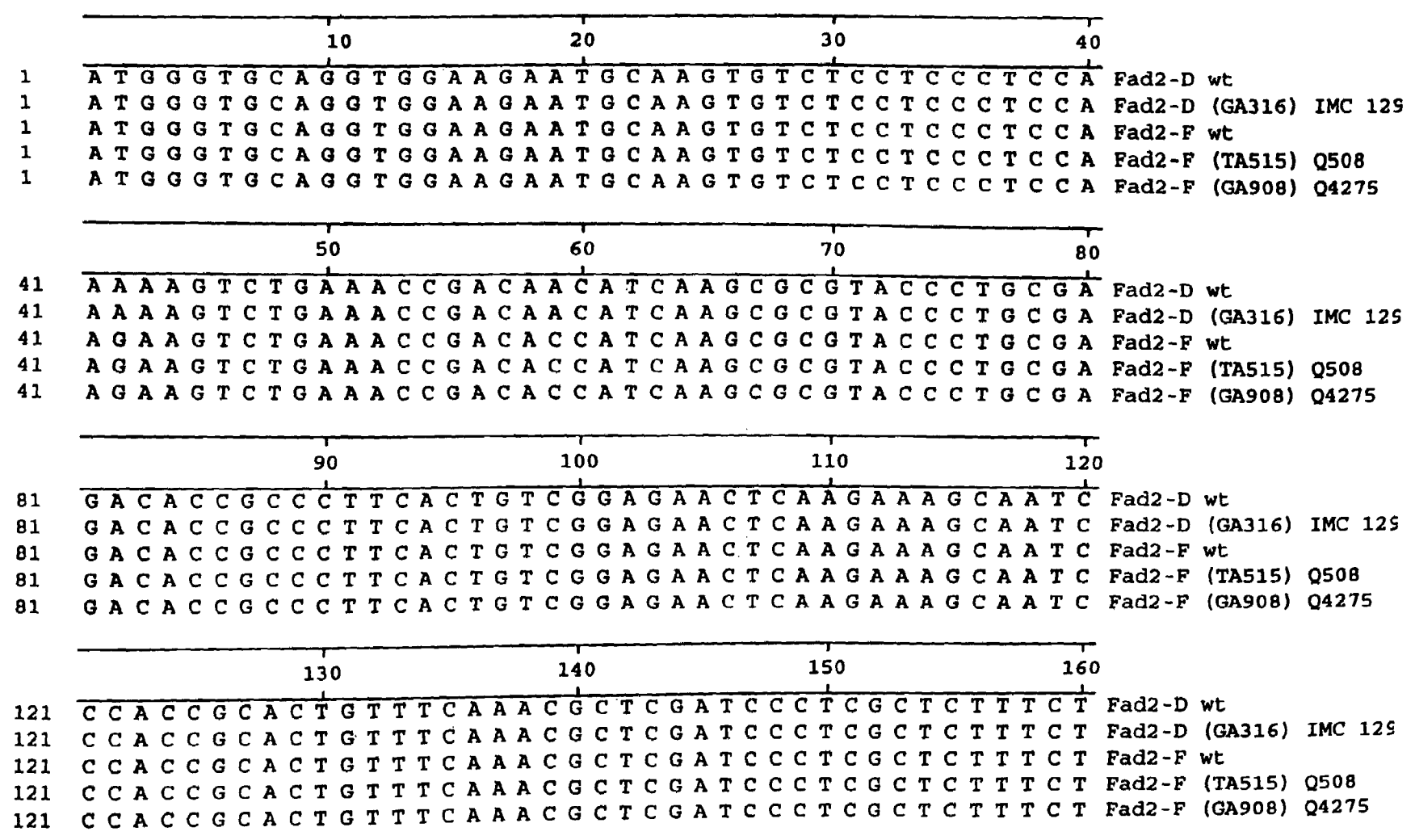
Figure 2D:
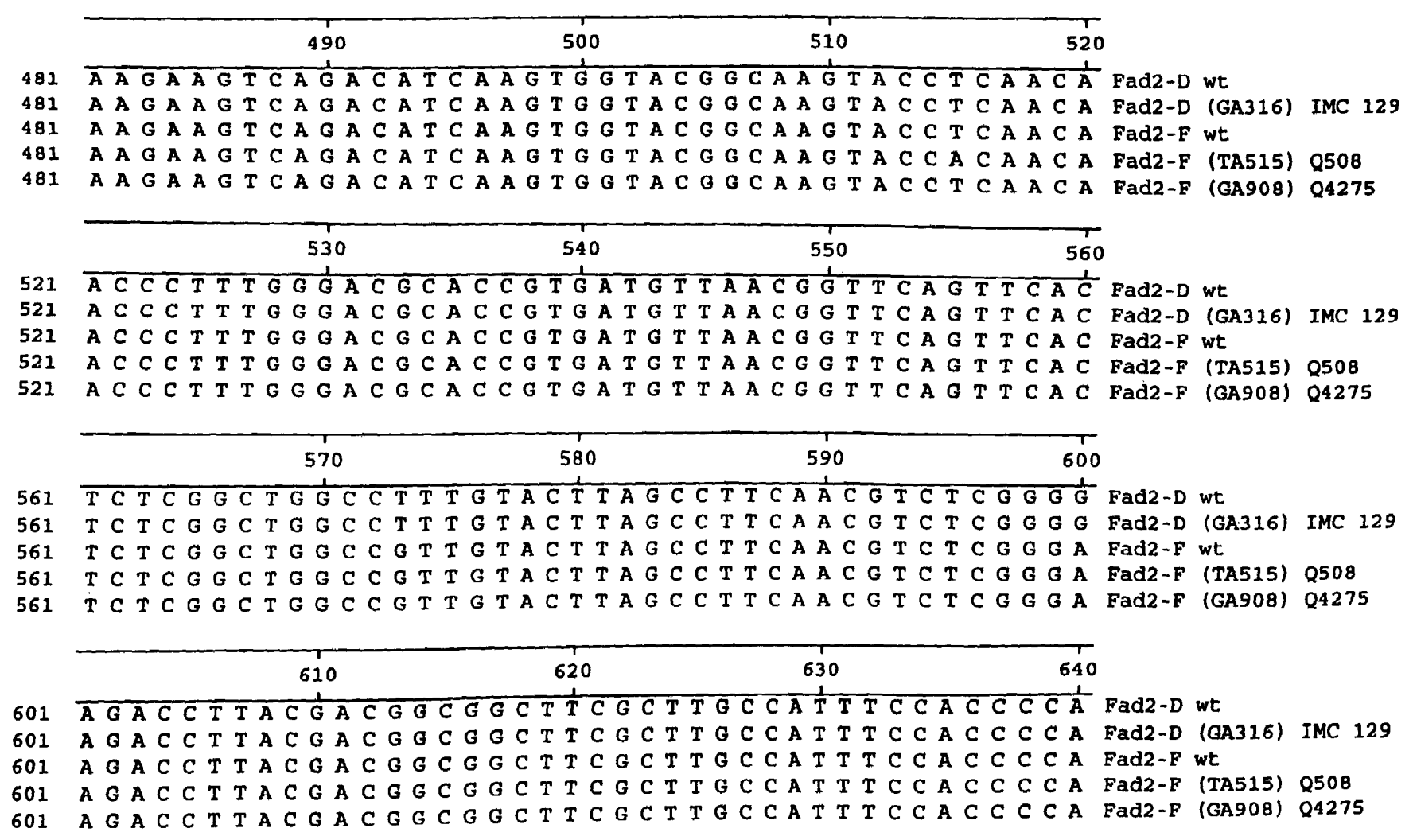

A single base transversion from G to A at nucleotide 908 was detected in the F gene sequence of the Q4275 amplified products, compared to the wild type F gene sequence (FIG. 2). This mutation changes the codon at amino acid 303 from GGA to GAA, resulting in the non-conservative substitution of a glutamic acid residue for a glycine residue (Table 3 and FIG. 3). Expression of the mutant Q4275 Fad2-F delta-12 desaturase gene in plants alters the fatty acid composition, as described hereinabove.

To the extent not already indicated, it will be understood by those of ordinary skill in the art that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. Progeny of a canola seed designated Q4275 and having ATCC accession no. 97569, wherein said progeny produces seeds yielding an oil having 80% to 90% oleic acid, and wherein said progeny comprises a first mutant delta-12 fatty acid desaturase and a second mutant delta-12 fatty acid desaturase, said first mutant delta-12 fatty acid desaturase comprising a substitution of a glutamic acid residue for a glycine at position 303 of SEQ ID NO:14, said second mutant delta-12 desaturase comprising a substitution of a lysine for a glutamic acid at position 106 of SEQ ID NO:10.

2. The progeny of claim 1, wherein said progeny produces seeds yielding an oil having about 2% to about 5% saturated fatty acids.

3. The progeny of claim 1, wherein said progeny produces seeds yielding an oil having about 0.5% to about 10% α-linolenic acid.

4. The progeny of claim 1, wherein said progeny produces seeds yielding an oil having about 1% to about 14% linoleic acid.

* * * * *